(12) United States Patent
Muller et al.

(10) Patent No.: US 7,893,101 B2
(45) Date of Patent: Feb. 22, 2011

(54) SOLID FORMS COMPRISING (+)-2-[1-(3-ETHOXY-4-METHOXYPHENYL)-2-METHYLSULFONYLETHYL]-4-ACETYLAMINOISOINDOLINE-1,3-DIONE, COMPOSITIONS THEREOF, AND USES THEREOF

(75) Inventors: George W. Muller, Bridgewater, NJ (US); Peter H. Schafer, Somerset, NJ (US); Hon-Wah Man, Princeton, NJ (US); Chuansheng Ge, Belle Mead, NJ (US); Jean Xu, Warren, NJ (US)

(73) Assignee: Celgene Corporation, Summit, NJ (US)

( * ) Notice: Subject to any disclaimer, the term of this patent is extended or adjusted under 35 U.S.C. 154(b) by 265 days.

(21) Appl. No.: 12/079,615

(22) Filed: Mar. 27, 2008

(65) Prior Publication Data

US 2008/0234359 A1    Sep. 25, 2008

Related U.S. Application Data

(60) Continuation-in-part of application No. 11/106,142, filed on Apr. 13, 2005, now Pat. No. 7,427,638, which is a division of application No. 10/392,195, filed on Mar. 19, 2003, now Pat. No. 6,962,940.

(60) Provisional application No. 60/366,515, filed on Mar. 20, 2002, provisional application No. 60/438,450, filed on Jan. 7, 2003.

(51) Int. Cl.
*A61K 31/40* (2006.01)
*C07D 209/56* (2006.01)

(52) U.S. Cl. .................. 514/411; 548/451
(58) Field of Classification Search ........... 514/411; 548/451
See application file for complete search history.

(56) References Cited

U.S. PATENT DOCUMENTS

| | | | |
|---|---|---|---|
| 3,031,450 A | 4/1962 | Fischer et al. |
| 3,322,755 A | 5/1967 | Roch et al. |
| 3,920,636 A | 11/1975 | Takahashi et al. |
| 4,001,237 A | 1/1977 | Partyka et al. |
| 4,001,238 A | 1/1977 | Partyka et al. |
| 4,047,404 A | 9/1977 | Hayashi |
| 4,060,615 A | 11/1977 | Matier et al. |
| 4,101,548 A | 7/1978 | Crenshaw et al. |
| 4,162,316 A | 7/1979 | Nishimura et al. |
| 4,209,623 A | 6/1980 | Juby |
| 4,880,810 A | 11/1989 | Lowe, III |
| 4,885,301 A | 12/1989 | Coates |
| 5,147,875 A | 9/1992 | Coates et al. |
| 5,354,571 A | 10/1994 | Morikawa et al. |
| 5,401,774 A | 3/1995 | Pamukcu et al. |
| 5,439,895 A | 8/1995 | Lee et al. |
| 5,488,055 A | 1/1996 | Kumar et al. |
| 5,608,914 A | 3/1997 | Keesler |
| 5,614,530 A | 3/1997 | Kumar et al. |
| 5,614,627 A | 3/1997 | Takase et al. |
| 5,658,940 A | 8/1997 | Muller et al. |
| 5,698,579 A | 12/1997 | Muller |
| 5,703,098 A | 12/1997 | Muller et al. |
| 5,710,170 A | 1/1998 | Guay et al. |
| 5,728,844 A | 3/1998 | Muller et al. |
| 5,728,845 A | 3/1998 | Muller et al. |
| 5,736,570 A | 4/1998 | Muller et al. |
| 5,798,373 A | 8/1998 | Warrellow |
| 5,801,195 A | 9/1998 | Muller et al. |
| 5,849,770 A | 12/1998 | Head et al. |
| 5,877,200 A | 3/1999 | Muller |
| 5,891,896 A | 4/1999 | Warrellow et al. |
| 6,011,050 A | 1/2000 | Muller et al. |
| 6,020,339 A | 2/2000 | Perrier et al. |
| 6,020,358 A * | 2/2000 | Muller et al. ............... 514/411 |
| 6,034,089 A | 3/2000 | Han et al. |
| 6,046,221 A | 4/2000 | Muller et al. |
| 6,069,156 A | 5/2000 | Oku et al. |
| 6,162,830 A | 12/2000 | Connor et al. |
| 6,166,041 A | 12/2000 | Cavalla et al. |
| 6,177,471 B1 | 1/2001 | Menander et al. |
| 6,204,275 B1 | 3/2001 | Friesen et al. |
| 6,218,400 B1 | 4/2001 | Daugan et al. |
| 6,300,335 B1 | 10/2001 | Campbell et al. |
| 6,316,472 B1 | 11/2001 | Frenette et al. |
| 6,333,354 B1 | 12/2001 | Schudt |

(Continued)

FOREIGN PATENT DOCUMENTS

EP    0 347 146    6/1989

(Continued)

OTHER PUBLICATIONS

Brittain's, polymorphism in Pharmaceutical Solids, Drugs and the Pharmaceutical Science; 1999, V. 95, pp. 348-361.*

(Continued)

*Primary Examiner*—Rei-tsang Shiao
(74) *Attorney, Agent, or Firm*—Jones Day

(57) ABSTRACT

Solid forms comprising (+)-2-[1-(3-Ethoxy-4-methoxyphenyl)-2-methylsulfonylethyl]-4-acetylaminoisoindoline-1,3-dione, compositions comprising the solid forms, methods of making the solid forms and methods of their use are disclosed. The methods include methods of treating and/or preventing disorders ameliorated by the reduction of levels of TNF-α or the inhibition of PDE4.

15 Claims, 33 Drawing Sheets

U.S. PATENT DOCUMENTS

| | | | |
|---|---|---|---|
| 7,427,638 B2 * | 9/2008 | Muller et al. ............... | 514/411 |
| 2008/0027123 A1 | 1/2008 | Muller et al. | |

FOREIGN PATENT DOCUMENTS

| | | |
|---|---|---|
| EP | 0 349 239 A2 | 6/1989 |
| EP | 0 351 058 | 6/1989 |
| EP | 0 352 960 A2 | 7/1989 |
| EP | 0 395 328 | 4/1990 |
| EP | 0 428 268 A2 | 10/1990 |
| EP | 0 463 756 A1 | 6/1991 |
| EP | 0 526 004 A1 | 7/1992 |
| EP | 0 607 439 A1 | 9/1992 |
| EP | 0 722 937 A1 | 1/1996 |
| EP | 0 722 943 A1 | 1/1996 |
| EP | 0 722 944 A1 | 1/1996 |
| GB | 2 063 249 A | 9/1980 |
| WO | WO 93/07149 | 4/1993 |
| WO | WO 93/12095 | 6/1993 |
| WO | WO 94/01728 | 1/1994 |
| WO | WO 94/05661 | 3/1994 |
| WO | WO 94/29277 | 12/1994 |
| WO | WO 95/19978 | 7/1995 |
| WO | WO 96/32379 | 10/1996 |
| WO | WO 97/03070 | 1/1997 |
| WO | WO 97/03675 | 2/1997 |
| WO | WO 97/03985 | 2/1997 |
| WO | WO 97/24334 | 7/1997 |
| WO | WO 98/06722 | 2/1998 |
| WO | WO 98/08848 | 3/1998 |
| WO | WO 98/14448 | 4/1998 |
| WO | WO 98/16521 | 4/1998 |
| WO | WO 98/17668 | 4/1998 |
| WO | WO 98/23597 | 6/1998 |
| WO | WO 98/38168 | 9/1998 |
| WO | WO 99/06041 | 2/1999 |
| WO | WO 03/080049 | 10/2003 |

OTHER PUBLICATIONS

Grant, D. J. W., "Theory and Origin of Polymorphism," *Polymorphism in Pharmaceutical Solids*, Jan. 1999:1-10.
International Search Report in corresponding application No. PCT/US2008/004021 dated Jan. 14, 2009.
U.S. Appl. No. 60/454,155, filed Mar. 12, 2003, Muller, G. et al.
U.S. Appl. No. 60/454,149, filed Mar. 12, 2003, Muller, G. et al.
U.S. Appl. No. 60/438,448, filed Jan. 7, 2003, Muller, G. et al.
U.S. Appl. No. 60/436,975, filed Dec. 30, 2002, Muller, G. et al.
U.S. Appl. No. 60/366,515, filed Mar. 20, 2002, Muller, G. et al.
Akazome, M. et al., 1997, "Asymmetric recognition of 1-arylethylamines by (R)-phenylglycyl-(R)-phenylglycine and its mechanism," Tetrahedron: Asymmetry, Elsevier Scince Publishers, Amsterdam, NL, 8(14):2331-2336.
Au et al., 1998, *Brit. J. Pharm.* 123:1260-1266.
Baehr et al., 1979, *J. Biol. Chem.* 254:11669.
Baughman et al., 1990,*J. Lab. Clin. Med.* 115:36-42.
Beavo and Reifsnyder, *Trends in Pharm.*, 11, 150-55, 1990.
Bissonnette et al., 1989, *Inflammation* 13:329-339.
Bloom and Beavo 1996, *Proc. Natl. Acad. Sci. USA* 93:14188-14192.
Brackeen, M.F. et al., 1995, "Design and synthesis of conformationally constrained analogues of 4-(3-butoxy-4-methoxybenzyl) imidazolidin-2-one (Ro 20/1724) as potent inhibitors of cAMP-specific phosphodiesterase", *J. Med. Chem.* 38:4848-54.
Carstensen, Jens T., 1995, *Drug Stability: Principles & Practice*, 2nd ed., Marcel Dekker, New York, NY pp. 379-380.
Casini et al., 1964, Farmaco Ed. Sci. 19:563.
Clouse et al, 1989, *J. Immunol.* 142:431-438.
Derian et al., 1995, *J. Immunol.* 154:308-317.
Duh et al., 1989, *Proc. Nat. Acad. Sci.* 86:5974-5978.
Featherstone, R.L., et al., 2000, "Comparison of phosphodiesterase inhibitors of differing isoenzyme selectivity added to St. Thomas' hospital cardioplegic solution used for hypothermic preservation of rat lungs", Am. J. Respir. Crit. Care Med. 162:850-6.
Gillespie et al., 1989, *Mol. Pharm*. 36:773.
Hidaka and Asano 1976, *Biochem. Biophys. Acta* 429:485.
Hinshaw et al. 1990, *Circ. Shock* 30:2797-292.
Holler et al., 1990, *Blood* 75:1011-1016.
Johnson et al., 1989, *Endocrinology* 124:1424-1427.
List et al., 1990, *J. Clin. Oncol.* 8:1424.MDS.
Luke, G.P. et al., 1999, "Synthesis of (S)-5-(1-aminoethyl)-2-(cyclohexylmethoxy) benzamide," Tetrahedron: Asymmetry, Elsevier Science Publishers, Amsterdam, NL, 10(22):4393-4403.
Merck Manual (1999) 17$^{th}$ ed., 953.
Monté et al., 1990, *Blood* 79:2670.
Muller, George, et al., 1999, *Bioorganic & Medicinal Chemistry Letters* 9; pp. 1625-1630.
Muller et al., 1998, *Bioorg. & Med Chem Lett.* 8:2669-2674.
Muller, et al., 1996, *J. Med. Chem.* 39:3238.
Nicholson et al., 1991, *Trends Pharmaco. Sci.* 12:19.
Shealy et al., 1965, "D- and L-thalidomide." *Chem. Indus.* 12;24:1030-1.
Tierney, et al., ed., 1998, Current Medical Diagnosis & Treatment, 37$^{th}$ ed., Appleton & Lange, pp. 499.
Verghese, et al., *Journal of Pharmacology and Experimental Therapeutics*, 272(3), 1313-1320, 1995.
Van Dullemen et al., 1995, *Gastroenterology*, 109:129-135.
Wilen, S.H., et al., 1977, *Tetrahedron* 33:2725.
Wilen, S.H., 1972, *Tables of Resolving Agents and Optical Resolutions* (E.L. Eliel, Ed., Univ. of Notre Dame Press, Notre Dame, IN) p. 268.
Wolff, Manfred E., ed., *Burger's Medicinal Chemistry and Drug Discovery*, 5$^{th}$ ed. 1995 172-178, 949-982.
Dredge et al., 2003, "Angiogenesis inhibitors in cancer therapy," Curr. Opin. Investig. Drugs 4(6):667-674.
Dredge et al., 2002, "Recent developments in antiangiogenic therapy," Expert Opin. Biol. Ther. 2(8):953-966.
Gee et al., 2003, "Selective cytokine inhibitory drugs with enhanced antiangiogenic activity control tumor growth through vascular inhibition," Cancer Res. 63(23):8073-8078.
Marriott et al., 2001, "Immunotherapeutic and antitumour potential of thalidomide analogues," Expert Opin. Biol. Ther. 1(4):1-8.
Marriott et al., 2002, "Thalidomide and its analogues have distinct and opposing effects on TNF-alpha and TNFR2 during co-stimulation of both CD4(+) and CD8(+) T cells," Clin. Exp. Immunol. 130(1):75-84.
Molostvov et al., 2004, "The effects of selective cytokine inhibitory drugs (CC-10004 and CC-1088) on VEGF and IL-6 expression and apoptosis in myeloma and endothelial cell co-cultures," Br. J. Haematol.124(3):366-375.
Notice of References Cited from Office Action dated Dec. 3, 2007 in U.S. Appl. No. 11/106,142.
Craven, B.M. et al., 1969, "Crystal structures of two polymorphs of 5-ethyl-5-isoamylbarbituric acid (amobarbital)," Acta Crystallographica, Section B: Structural Crystal Chemistry, B25 (PL. 10).
Berge et al., 1977, "Pharmaceutical Salts," Journal of Pharmaceutical Sciences, 66(1):1-19.
Bundgaard, Hans, 1985, "Design of prodrugs: Bioreversible derivatives for various functional groups and chemical entities," Design of Prodrugs, Chapter 1:1-4.
U.S. Department of Health and Human Services, Food and Drug Administration, 2000, "Guidance for Industry—Impurities: Residual Solvents in New Veterinary Medicinal Products, Active Substances and Excipients," pp. 1-20.
Craven et al., 1969, CAS: 71:117431.
Berge et al., Journal of pharmaceutical Science, 1977, vol. 66, pp. 1-19.
Bundgaard et al. publication, 1985, Design of prodrug, pp. 1-4.
FDA's guidance for industry, 2000, pp. 1-20.
Jones et al., "Pharmaceutical Cocrystals: An Emerging Approach to Physical Property Enhancement," *Mater. Res. Bull.*, 31:875-79 (2006).

Andrew D. Bond & William Jones, Controlling Crystal Architecture in Molecular Solids: The Supramolecular Approach, in Supramolecular Organization and Materials Design, 391, 436 (W. Jones & C. N. R. Rao, eds., 2001).

Trask et al., "Selective polymorph transformation via solvent-drop grinding," *Chem. Commun.*, 880-882 (2005).

* cited by examiner

SOLID FORMS COMPRISING (+)-2-[1-(3-ETHOXY-4-METHOXYPHENYL)-2-METHYLSULFONYLETHYL]-4-ACETYLAMINOISOINDOLINE-1,3-DIONE, COMPOSITIONS THEREOF, AND USES THEREOF

This application is a continuation-in-part of U.S. patent application Ser. No. 11/106,142, filed Apr. 13, 2005 now U.S. Pat. No. 7,427,638, which is a divisional of U.S. patent application Ser. No. 10/392,195, filed on Mar. 19, 2003, issued as U.S. Pat. No. 6,962,940, which claims the benefit of U.S. Provisional Patent Application No. 60/366,515, filed on Mar. 20, 2002, and U.S. Provisional Patent Application No. 60/438,450, filed on Jan. 7, 2003, the entireties of which are incorporated herein by reference.

1. FIELD OF INVENTION

Provided herein are solid forms comprising (+)-2-[1-(3-ethoxy-4-methoxyphenyl)-2-methylsulfonylethyl]-4-acetylaminoisoindoline-1,3-dione, compositions comprising the solid forms, methods of making the solid forms and methods of their use for the treatment of various diseases and/or disorders.

2. BACKGROUND OF THE INVENTION

Tumor necrosis factor alpha (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. However, TNF-α also has a role in many diseases. When administered to a patient, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-borne tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as, but not limited to, asthma and inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

It is believed that the primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150-155, 1990). There are eleven known PDE families. It is recognized, for example, that the inhibition of PDE type IV is particularly effective in both the inhibition of inflammatory mediator release and the relaxation of airway smooth muscle (Verghese, et al., *J. Pharm. Exper. Therapeut.*, 272(3), 1313-1320, 1995). Thus, compounds that inhibit PDE4 (PDE IV) specifically, may inhibit inflammation and aid the relaxation of airway smooth muscle with a minimum of unwanted side effects, such as cardiovascular or anti-platelet effects. Currently used PDE4 inhibitors lack the selective action at acceptable therapeutic doses.

Cancer is a particularly devastating disease, and increases in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. However, increased levels of cytokines have been shown to substantially increase the adhesion of cancer cells to endothelium in vitro. One explanation is that cytokines, such as TNF-α, stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response, ELAM-1 on endothelial cells functions as a "homing receptor" for leukocytes. Recently, ELAM-1 on endothelial cells was shown to mediate the increased adhesion of colon cancer cells to endothelium treated with cytokines (Rice et al., 1989, *Science* 246:1303-1306).

Inflammatory diseases such as arthritis, related arthritic conditions (e.g., osteoarthritis and rheumatoid arthritis), inflammatory bowel disease (e.g., Crohn's disease and ulcerative colitis), sepsis, psoriasis, atopic dermatitis, contact dermatitis, chronic obstructive pulmonary disease, and chronic inflammatory pulmonary diseases are also prevalent and problematic ailments. TNF-α plays a central role in the inflammatory response and the administration of their antagonists block chronic and acute responses in animal models of inflammatory disease.

Enhanced or unregulated TNF-α production has been implicated in viral, genetic, inflammatory, allergic, and autoimmune diseases. Examples of such diseases include but are not limited to: HIV; hepatitis; adult respiratory distress syndrome; bone-resorption diseases; chronic obstructive pulmonary diseases; chronic pulmonary inflammatory diseases; asthma; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; ENL in leprosy; radiation damage; asthma; and hyperoxic alveolar injury. Tracey et al., 1987, *Nature* 330:662-664 and Hinshaw et al., 1990, *Circ. Shock* 30:279-292 (endotoxic shock); Dezube et al., 1990, *Lancet*, 335:662 (cachexia); Millar et al., 1989, *Lancet* 2:712-714 and Ferrai-Baliviera et al., 1989, *Arch. Surg.* 124:1400-1405 (adult respiratory distress syndrome); Bertolini et al., 1986, *Nature* 319:516-518, Johnson et al., 1989, *Endocrinology* 124:1424-1427, Holler et al., 1990, *Blood* 75:1011-1016, and Grau et al., 1989, *N. Engl. J. Med.* 320:1586-1591 (bone resorption diseases); Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109:129-135 (Crohn's disease); Duh et al., 1989, *Proc. Nat. Acad. Sci.* 86:5974-5978, Poll et al., 1990, *Proc. Nat. Acad. Sci.* 87:782-785, Monto et al., 1990, *Blood* 79:2670, Clouse et al., 1989, *J. Immunol.* 142, 431-438, Poll et al., 1992, *AIDS Res. Hum. Retrovirus*, 191-197, Poli et al. 1990, *Proc. Natl. Acad. Sci.* 87:782-784, Folks et al., 1989, PNAS 86:2365-2368 (HIV and opportunistic infections resulting from HIV).

Pharmaceutical compounds that can block the activity or inhibit the production of certain cytokines, including TNF-α, may be beneficial therapeutics. Many small-molecule inhibitors have demonstrated an ability to treat or prevent inflammatory diseases implicated by TNF-α (for a review, see Lowe, 1998 *Exp. Opin. Ther. Patents* 8:1309-1332). One such class of molecules are the substituted phenethylsulfones described in U.S. Pat. No. 6,020,358.

The preparation and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise, e.g., from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of studying polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise, e.g., from the possibility of multiple-component solids. Crystalline solids comprising two or more ionic species may be termed salts (see, e.g., *Handbook of Pharmaceutical Salts Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The preparation of solid forms is of great importance in the development of a safe, effective, stable and marketable pharmaceutical compound.

Provided herein are embodiments addressing a need for solid forms of the compound chemically named (+)-2-[1-(3-ethoxy-4-methoxyphenyl)-2-methylsulfonylethyl]-4-acetylaminoisoindoline-1,3-dione ("Compound A"), which was disclosed in U.S. application Ser. No. 10/392,195, filed Mar. 19, 2003 (issued as U.S. Pat. No. 6,962,940), as well as U.S. Provisional Application Ser. Nos. 60/366,515, filed Mar. 20, 2002 and 60/438,450, filed Jan. 7, 2003.

3. SUMMARY OF THE INVENTION

This invention relates to methods of treating diseases and disorders utilizing an enantiomer of a substituted phenethylsulfone compound and pharmaceutically acceptable solvates, hydrates, co-crystals, clathrates, prodrugs and polymorphs thereof and methods for reducing the level of cytokines and their precursors in mammals. The invention also relates to pharmaceutical compositions comprising the (+) enantiomer of 2-[1-(3-Ethoxy-4-methoxyphenyl)-2-methylsulfonylethyl]-4-acetylaminoisoindoline-1,3-dione and a pharmaceutically acceptable carrier. The invention further relates to the (+) enantiomer of 2-[1-(3-Ethoxy-4-methoxyphenyl)-2-methylsulfonylethyl]-4-acetylaminoisoindoline-1,3-dione substantially free of its (−) enantiomer.

This invention particularly relates to the (+) enantiomer of 2-[1-(3-Ethoxy-4-methoxyphenyl)-2-methylsulfonylethyl]-4-acetylaminoisoindoline-1,3-dione. This compound is believed to have increased potency and other benefits as compared to its racemate, 2-[1-(3-Ethoxy-4-methoxyphenyl)-2-methylsulfonylethyl]-4-acetylaminoisoindoline-1,3-dione.

The invention encompasses the use of the (+) enantiomer of 2-[1-(3-Ethoxy-4-methoxyphenyl)-2-methylsulfonylethyl]-4-acetylaminoisoindoline-1,3-dione for treating or preventing diseases or disorders ameliorated by the inhibition of TNF-α production in mammals. In certain embodiments, this treatment includes the reduction or avoidance of adverse effects. Such disorders include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors.

The invention also encompasses the use of the (+) enantiomer of 2-[1-(3-Ethoxy-4-methoxyphenyl)-2-methylsulfonylethyl]-4-acetylaminoisoindoline-1,3-dione in the treatment or prevention of heart disease, including, but not limited to congestive heart failure, cardiomyopathy, pulmonary edema, endotoxin-mediated septic shock, acute viral myocarditis, cardiac allograft rejection, and myocardial infarction.

The invention also encompasses the use of the (+) enantiomer of 2-[1-(3-Ethoxy-4-methoxyphenyl)-2-methylsulfonylethyl]-4-acetylaminoisoindoline-1,3-dione to treat diseases or disorders ameliorated by the inhibition of PDE4. For example, the compounds and compositions of the invention may be useful to treat or prevent viral, genetic, inflammatory, allergic, and autoimmune diseases. Examples of such diseases include, but are not limited to: HIV; hepatitis; adult respiratory distress syndrome; bone-resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic reperfusion injury; meningitis; psoriasis; fibrotic disease; cachexia; graft rejection including graft versus host disease; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; erythema nodosum leprosum (ENL) in leprosy; radiation damage; asthma; and hyperoxic alveolar injury.

In yet another embodiment, the stereomerically pure (+) enantiomer of 2-[1-(3-Ethoxy-4-methoxyphenyl)-2-methylsulfonylethyl]-4-acetylaminoisoindoline-1,3-dione is also useful in the treatment or prevention of microbial infections or the symptoms of microbial infections including, but not limited to, bacterial infections, fungal infections, malaria, mycobacterial infection, and opportunistic infections resulting from HIV.

The invention further encompasses pharmaceutical compositions and single unit dosage forms comprising the (+) enantiomer of 2-[1-(3-Ethoxy-4-methoxyphenyl)-2-methylsulfonylethyl]-4-acetylaminoisoindoline-1,3-dione and pharmaceutically acceptable polymorphs, prodrugs, hydrates, clathrates, and solvates thereof.

In a separate embodiment, the invention encompasses the (+) enantiomer of 2-[1-(3-Ethoxy-4-methoxyphenyl)-2-methylsulfonylethyl]-4-acetylaminoisoindoline-1,3-dione.

In a further embodiment, the invention encompasses a method of producing the stereomerically pure (+) enantiomer of 2-[1-(3-Ethoxy-4-methoxyphenyl)-2-methylsulfonylethyl]-4-acetylaminoisoindoline-1,3-dione which comprises contacting 1-(3-Ethoxy-4-methoxy-phenyl)-2-methanesulfonyl-ethylamine with a chiral amino acid and contacting the product of the first step with N-(1,3-Dioxo-1,3-dihydroisobenzofuran-4-yl)-acetamide. In a related embodiment the invention encompasses a chiral salt of 1-(3-Ethoxy-4-methoxy-phenyl)-2-methanesulfonyl-ethylamine.

Embodiments herein provide solid forms comprising the compound chemically named (+)-2-[1-(3-ethoxy-4-methoxyphenyl)-2-methylsulfonylethyl]-4-acetylaminoisoindoline-1,3-dione ("Compound A"). Compound A can be synthesized or obtained according to any method apparent to those of skill in the art based upon the teachings herein, including the methods described in the Examples below. Compound A can also be prepared according to the methods described in U.S. Pat. No. 6,962,940, issued Nov. 8, 2005, the entirety of which is incorporated by reference herein.

In certain embodiments, the solid forms are single-component crystal forms of Compound A. In certain embodiments, the solid forms are multiple-component crystal forms, including, but not limited to, co-crystals and/or solvates (including hydrates) comprising Compound A. In other embodiments, the solid forms are single-component amorphous forms of Compound A. In other embodiments, the solid forms are multiple-component amorphous forms. Without intending to be limited by any particular theory, certain novel solid forms provided herein have particular advantageous physical and/or chemical properties making them useful, e.g., for manufacturing, processing, formulation and/or storage, while also possessing particularly advantageous biological properties, such as, e.g., bioavailability and/or biological activity.

In particular embodiments, solid forms provided herein include solid forms comprising Compound A, including, but not limited to, single-component and multiple-component solid forms comprising Compound A. In certain embodiments, solid forms provided herein include polymorphs, solvates (including hydrates) and co-crystals comprising Compound A. Certain embodiments herein provide methods of making, isolating and/or characterizing the solid forms provided herein.

The solid forms provided herein are useful as active pharmaceutical ingredients for the preparation of formulations for use in patients. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising Compound A and a pharmaceutically acceptable diluent, excipient or carrier. The solid forms and the final drug products provided herein are useful, for example, for the treatment, prevention or management of diseases and disorders provided herein.

Certain embodiments herein provide methods using the solid forms provided herein for treating, preventing or managing diseases or disorders ameliorated by the inhibition of TNF-α production in mammals, such as HIV; hepatitis; adult respiratory distress syndrome; bone resorption diseases; chronic obstructive pulmonary diseases; chronic pulmonary inflammatory diseases; asthma; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto immune disease; rheumatoid spondylitis; arthritic conditions, such as psoriatic arthritis, rheumatoid arthritis and osteoarthritis; osteoporosis; Crohn's disease; ulcerative colitis; inflammatory bowel disease; multiple sclerosis; systemic lupus erythematosus; cutaneous lupus erythematosus; pulmonary sarcoidosis; ENL in leprosy; radiation damage; asthma; and hyperoxic alveolar injury. Such disorders further include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors. In certain embodiments, methods using the solid forms provided herein include the reduction or avoidance of certain adverse effects.

Certain embodiments herein provide methods of using the solid forms provided herein in the treatment or prevention of heart disease, including, but not limited to congestive heart failure, cardiomyopathy, pulmonary edema, endotoxin-mediated septic shock, acute viral myocarditis, cardiac allograft rejection, and myocardial infarction.

Certain embodiments herein provide methods of using the solid forms provided herein to treat diseases or disorders ameliorated by the inhibition of PDE4. For example, the solid forms provided herein may be useful to treat or prevent viral, genetic, inflammatory, allergic, and autoimmune diseases. Examples of such diseases include, but are not limited to: HIV; hepatitis; adult respiratory distress syndrome; bone-resorption diseases; chronic obstructive pulmonary diseases; chronic pulmonary inflammatory diseases; dermatitis; inflammatory skin disease; atopic dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection including graft versus host disease; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; erythema nodosum leprosum (ENL) in leprosy; radiation damage; asthma; and hyperoxic alveolar injury.

Certain embodiments herein provide methods of using the solid forms provided herein in the treatment or prevention of microbial infections or the symptoms of microbial infections including, but not limited to, bacterial infections, fungal infections, malaria, mycobacterial infection, and opportunistic infections resulting from HIV.

Particular embodiments herein provide methods of using the solid forms provided herein in the treatment or prevention of diseases including: psoriasis; psoriatic arthritis; rheumatoid arthritis; chronic cutaneous sarcoid; giant cell arteritis; Parkinson's; prurigo nodularis; lichen planus; complex apthosis; Behcet's disease; lupus; hepatitis; uveitis; Sjogren's disease; depression (including major depression); interstitial cystitis; vulvodynia; prostatitis; osteoarthritis; diffuse large B cell lymphoma; polymysoitis; dermatomyositis; inclusion body myositis; erosive osteoarthritis; interstitial cystitis; hepatitis; endometriosis; radiculopathy; and pyoderma gangrenosum.

Certain embodiments herein provide pharmaceutical compositions and single unit dosage forms comprising one or more solid forms provided herein.

3.1. BRIEF DESCRIPTION OF THE FIGURES

FIG. 1 provides a representative X-ray Powder Diffraction ("XRPD") pattern of Form A of Compound A.

FIG. 2 provides a representative Differential Scanning Calorimetry ("DSC") plot of Form A of Compound A.

FIG. 3 provides a representative Thermal Gravimetric Analysis ("TGA") plot of Form A of Compound A.

FIG. 4 provides a representative Dynamic Vapor Sorption ("DVS") plot of Form A of Compound A.

FIG. 5 provides a representative XRPD pattern of Form B of Compound A.

FIG. 6 provides a representative DSC plot of Form B of Compound A.

FIG. 7 provides a representative TGA plot of Form B of Compound A.

FIG. 8 provides a representative DVS plot of Form B of Compound A.

FIG. 9 provides a representative XRPD pattern of Form C of Compound A.

FIG. 10 provides a representative DSC plot of Form C of Compound A.

FIG. 11 provides a representative TGA plot of Form C of Compound A.

FIG. 12 provides a representative DVS plot of Form C of Compound A.

FIG. 13 provides a representative XRPD pattern of Form D of Compound A.

FIG. 14 provides a representative DSC plot of Form D of Compound A.

FIG. 15 provides a representative TGA plot of Form D of Compound A.

FIG. 16 provides a representative DVS plot of Form D of Compound A.

FIG. 17 provides a representative XRPD pattern of Form E of Compound A.

FIG. 18 provides a representative DSC plot of Form E of Compound A.

FIG. 19 provides a representative TGA plot of Form E of Compound A.

FIG. 20 provides a representative DVS plot of Form E of Compound A.

FIG. 21 provides a representative XRPD pattern of Form F of Compound A.

FIG. 22 provides a representative DSC plot of Form F of Compound A.

FIG. 23 provides a representative TGA plot of Form F of Compound A.

FIG. 24 provides a representative DVS plot of Form F of Compound A.

FIG. 25 provides a representative XRPD of Form G of Compound A.

FIG. 26 provides a representative DSC plot of Form G of Compound A.

FIG. 27 provides a representative TGA plot of Form G of Compound A.

FIG. 28 provides a representative DVS plot of Form G of Compound A.

3.2. DEFINITIONS

Figure 1:
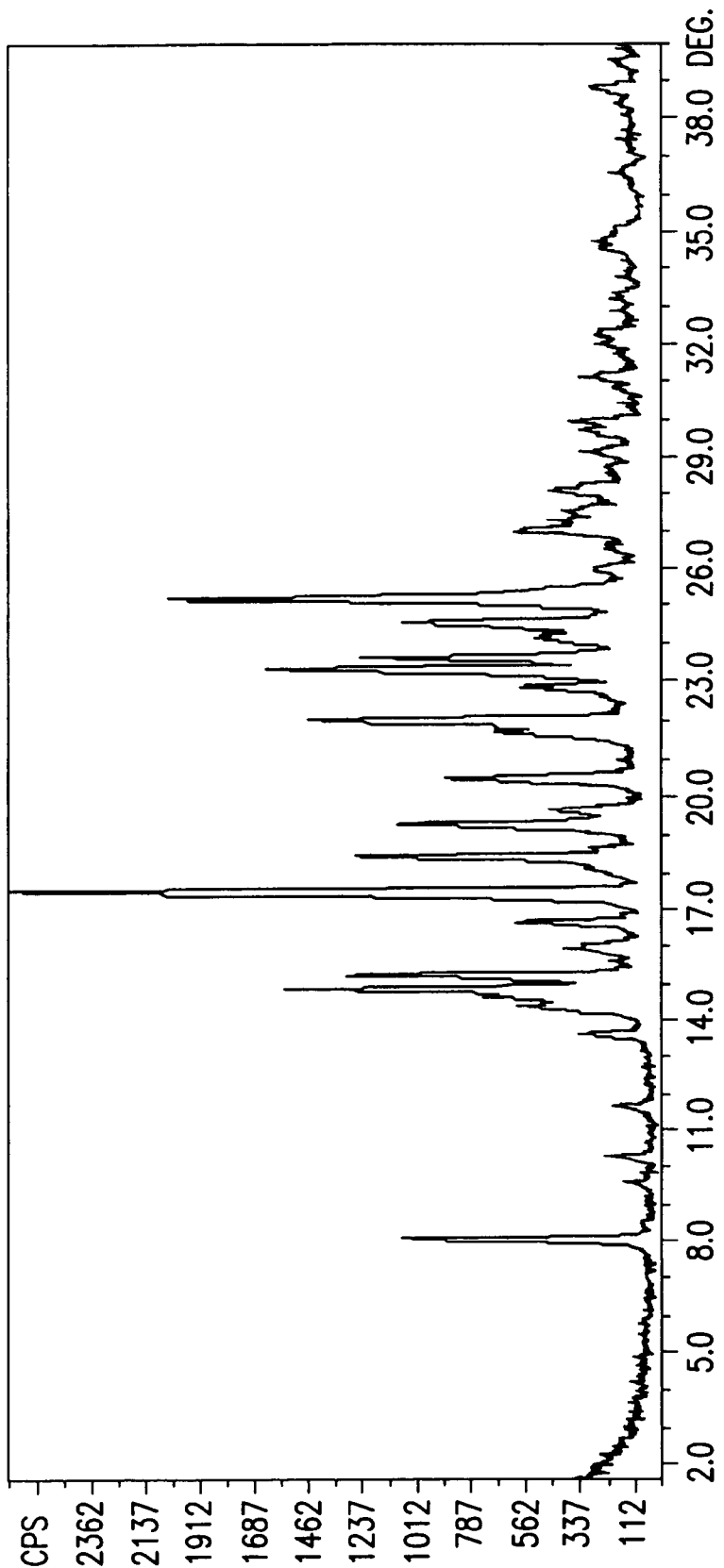

As used herein, term "Compound A" refers to enantiomerically pure (+)-2-[1-(3-ethoxy-4-methoxyphenyl)-2-methylsulfonylethyl]-4-acetylaminoisoindoline-1,3-dione which comes off of an HPLC column at about 25.4 minutes when that column is a 150 mm×4.6 mm Ultron Chiral ES-OVS chiral HPLC column (Agilent Technology), the eluent is 15:85 ethanol: 20 mM $KH_2PO_4$ at pH 3.5, and the observation wavelength is 240 nm. The $^1H$ NMR spectrum of Compound A is substantially as follows: δ($CDCl_3$); 1.47 (t, 3H); 2.26 (s, 3H); 2.87 (s, 3H); 3.68-3.75 (dd, 1H); 3.85 (s, 3H); 4.07-4.15 (q, 2H); 4.51-4.61 (dd, 1H); 5.84-5.90 (dd, 1H); 6.82-8.77 (m, 6H); 9.46 (s, 1H). The $^{13}C$ NMR spectrum of Compound A is substantially as follows: δ(DMSO-$d_6$); 14.66; 24.92; 41.61; 48.53; 54.46; 55.91; 64.51; 111.44; 112.40; 115.10; 118.20; 120.28; 124.94; 129.22; 131.02; 136.09; 137.60; 148.62; 149.74; 167.46; 169.14; 169.48. Compound A dissolved in methanol rotates plane polarized light in the (+) direction.

Without being limited by theory, Compound A is believed to be S-{2-[1-(3-ethoxy-4-methoxyphenyl)-2-methylsulfonylethyl]-4-acetylaminoisoindoline-1,3-dione}, which has the following structure:

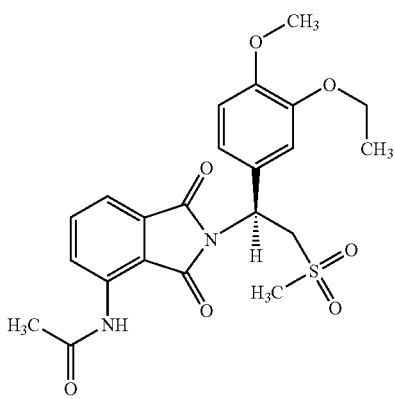

As used herein, the term "patient" refers to a mammal, particularly a human.

As used herein, the term "pharmaceutically acceptable salts" refer to salts prepared from pharmaceutically acceptable non-toxic acids or bases including inorganic acids and bases and organic acids and bases.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of Compound A that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein and unless otherwise specified, the terms "solid form" and related terms refer to a physical form which is not predominantly in a liquid or a gaseous state. As used herein and unless otherwise specified, the term "solid form" and related terms, when used herein to refer to Compound A, refer to a physical form comprising Compound A which is not predominantly in a liquid or a gaseous state. Solid forms may be crystalline, amorphous or mixtures thereof. In particular embodiments, solid forms may be liquid crystals. A "single-component" solid form comprising Compound A consists essentially of Compound A. A "multiple-component" solid form comprising Compound A comprises a significant quantity of one or more additional species, such as ions and/or molecules, within the solid form. For example, in particular embodiments, a crystalline multiple-component solid form comprising Compound A further comprises one or more species non-covalently bonded at regular positions in the crystal lattice. Multiple-component solid forms comprising Compound A include co-crystals, solvates (e.g., hydrates), and clathrates of Compound A. In particular embodiments, the term "solid form comprising Compound A" and related terms include single-component and multiple-component solid forms comprising Compound A. In particular embodiments, "solid forms comprising Compound A" and related terms include crystal forms comprising Compound A, amorphous forms comprising Compound A, and mixtures thereof.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules, and/or ions. Like different crystal forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein and unless otherwise specified, the terms "solvate" and "solvated," refer to a crystal form of a substance which contains solvent. The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance be about 99%, 98%, 97%, 96%, 95%, 94%, 93%, 92%, 91% or 90% physically and/or chemically pure.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

4. DETAILED DESCRIPTION OF THE INVENTION

This invention relates to stereomerically pure Compound A, which is the (+) enantiomer of 2-[1-(3-Ethoxy-4-methoxyphenyl)-2-methylsulfonylethyl]-4-acetylaminoisoindoline-1,3-dione, substantially free of its (−) enantiomer, as well as novel methods of using, and compositions comprising, stereomerically pure Compound A and/or solid forms comprising Compound A. For example, the present invention encompasses the in vitro and in vivo use of Compound A, and the incorporation of Compound A into pharmaceutical compositions and single unit dosage forms useful in the treatment and prevention of a variety of diseases and disorders. Diseases and disorders which are ameliorated by the reduction of levels of TNF-α or inhibition of PDE4 are well known in the art and are described herein. Specific methods of the invention reduce or avoid the adverse effects associated with compounds used as TNF-α inhibitor. Other specific methods of the invention reduce or avoid the adverse effects associated with use of racemic 2-[1-(3-Ethoxy-4-methoxyphenyl)-2-methylsulfonylethyl]-4-acetylaminoisoindoline-1,3-dione.

Specific methods of the invention include methods of treating or preventing diseases and disorders including, but not limited to, solid tumors, blood-borne tumors and inflammatory diseases.

Pharmaceutical and dosage forms of the invention, which comprise Compound A or a pharmaceutically acceptable polymorph, prodrug, clathrate, solvate or hydrate thereof (wherein particular embodiments encompass solid forms comprising Compound A as described herein) can be used in the methods of the invention.

Without being limited by theory, it is believed that Compound A, including solid forms comprising Compound A, can inhibit TNF-α production. Consequently, a first embodiment of the invention relates to a method of inhibiting TNF-α production which comprises contacting a cell exhibiting abnormal TNF-α production with an effective amount of stereomerically pure Compound A or a pharmaceutically acceptable prodrug, metabolite, polymorph, solvate, hydrate, or clathrate thereof (wherein particular embodiments encompass solid forms comprising Compound A as described herein). In a particular embodiment, the invention relates to a method of inhibiting TNF-α production which comprises contacting a mammalian cell exhibiting abnormal TNF-α production with an effective amount of stereomerically pure Compound A or a pharmaceutically acceptable prodrug, metabolite, polymorph, solvate, hydrate, or clathrate thereof (wherein particular embodiments encompass solid forms comprising Compound A as described herein).

The invention also relates to a method of treating, preventing or managing disorders ameliorated by the reduction of levels of TNF-α in a patient which comprises administering to a patient in need of such treatment or prevention a therapeutically or prophylactically effective amount of stereomerically pure Compound A or a pharmaceutically acceptable prodrug, metabolite, polymorph, solvate, hydrate, or clathrate thereof (wherein particular embodiments encompass solid forms comprising Compound A as described herein). In particular embodiments, diseases or disorders ameliorated by the inhibition of TNF-α production in mammals include, but are not limited to: HIV; hepatitis; adult respiratory distress syndrome; bone resorption diseases; chronic obstructive pulmonary diseases; chronic pulmonary inflammatory diseases; asthma; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto immune disease; rheumatoid spondylitis; arthritic conditions, such as psoriatic arthritis, rheumatoid arthritis and osteoarthritis; osteoporosis; Crohn's disease; ulcerative colitis; inflammatory bowel disease; multiple sclerosis; systemic lupus erythematosus; cutaneous lupus erythematosus; pulmonary sarcoidosis; erythema nodosum leprosum (ENL) in leprosy; radiation damage; asthma; and hyperoxic alveolar injury. Such disorders further include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors.

A further embodiment of the invention relates to a method of treating or preventing cancer, including but not limited to, solid tumor, blood-borne tumor, leukemias, and in particular, multiple myeloma in a patient which comprises administering to a patient in need of such treatment or prevention a therapeutically effective amount of stereomerically pure Compound A or a pharmaceutically acceptable prodrug, metabolite, polymorph, solvate, hydrate, or clathrate thereof (wherein particular embodiments encompass solid forms comprising Compound A as described herein); in particular wherein the patient is a mammal.

In another embodiment, the invention relates to a method of inhibiting PDE4 which comprises contacting PDE4 in a cell (e.g. a mammalian cell) with an effective amount of stereomerically pure Compound A or a pharmaceutically acceptable prodrug, metabolite, polymorph, solvate, hydrate, or clathrate thereof (wherein particular embodiments encompass solid forms comprising Compound A as described herein).

A further embodiment of the invention relates to a method of treating or preventing diseases or disorders ameliorated by the inhibition of PDE4 in a patient which comprises administering to a patient in need of such treatment or prevention a therapeutically or prophylactically effective amount of stereomerically pure Compound A or a pharmaceutically acceptable prodrug, metabolite, polymorph, solvate, hydrate, or clathrate thereof (wherein particular embodiments encompass solid forms comprising Compound A as described herein). Disorders ameliorated by the inhibition of PDE4 include, but are not limited to, asthma, inflammation (e.g., inflammation due to reperfusion), chronic or acute obstructive pulmonary diseases, chronic or acute pulmonary inflammatory diseases, inflammatory bowel disease, Crohn's Disease, Behcet's Disease, or colitis.

In another embodiment, the invention relates to a method of controlling cAMP levels in a cell which comprises contacting a cell with an effective amount of stereomerically pure Compound A or a pharmaceutically acceptable prodrug, metabolite, polymorph, solvate, hydrate, or clathrate thereof (wherein particular embodiments encompass solid forms comprising Compound A as described herein). As used herein the term "controlling cAMP levels" includes preventing or reducing the rate of the breakdown of Adenosine 3',5'-cyclic monophosphate (cAMP) in a cell or increasing the amount of Adenosine 3',5'-cyclic monophosphate present in a cell, preferably a mammalian cell, more preferably a human cell. In a particular method, the rate of cAMP breakdown is reduced by about 10, 25, 50, 100, 200, or 500 percent as compared to the rate in comparable cells which have not been contacted with a compound of the invention.

A further embodiment of the invention relates to a method of treating or preventing depression, asthma, inflammation (e.g., contact dermatitis, atopic dermatitis, psoriasis, rheumatoid arthritis, osteoarthritis, inflammatory skin disease, inflammation due to reperfusion), chronic or acute obstructive pulmonary diseases, chronic or pulmonary inflammatory diseases, inflammatory bowel disease, Crohn's Disease, Behcet's Disease or colitis in a patient which comprises administering to a patient in need of such treatment or prevention a therapeutically or prophylactically effective amount of stereomerically pure Compound A or a pharmaceutically acceptable prodrug, metabolite, polymorph, solvate, hydrate, or clathrate thereof (wherein particular embodiments encompass solid forms comprising Compound A as described herein); in particular wherein the patient is a mammal.

A separate embodiment of the invention encompasses methods of treating or preventing myelodysplastic syndrome (MDS) which comprises administering to a patient in need of such treatment or prevention a therapeutically or prophylactically effective amount of stereomerically pure Compound A or a pharmaceutically acceptable solvate, hydrate, stereoisomer, clathrate, or prodrug thereof (wherein particular embodiments encompass solid forms comprising Compound A as described herein). MDS refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. See *The Merck Manual* 953 (17th ed. 1999) and List et al., 1990, *J. Clin. Oncol.* 8:1424.

A separate embodiment of the invention encompasses methods of treating or preventing myeloproliferative disease (MPD) which comprises administering to a patient in need of such treatment or prevention a therapeutically or prophylactically effective amount of stereomerically pure Compound A or a pharmaceutically acceptable solvate, hydrate, stereoisomer, clathrate, or prodrug thereof (wherein particular embodiments encompass solid forms comprising Compound A as described herein). Myeloproliferative disease (MPD) refers to a group of disorders characterized by clonal abnormalities of the hematopoietic stem cell. See e.g., *Current Medical Diagnosis & Treatment*, pp. 499 (37th ed., Tierney et al., ed., Appleton & Lange, 1998).

The invention also encompasses a method of treating, preventing or managing pain, including, but not limited to, complex regional pain syndrome, which comprises administering to a patient in need of such treatment, prevention or management a therapeutically or prophylactically effective amount of a stereomerically pure Compound A or a pharmaceutically acceptable solvate, hydrate, stereoisomer, clathrate, or prodrug thereof (wherein particular embodiments encompass solid forms comprising Compound A as described herein). In a specific embodiment, the administration is before, during or after surgery or physical therapy directed at reducing or avoiding a symptom of complex regional pain syndrome in the patient.

In particular methods of the invention, stereomerically pure Compound A or a pharmaceutically acceptable polymorph, prodrug, solvate, hydrate, or clathrate thereof (wherein particular embodiments encompass solid forms comprising Compound A as described herein), is adjunctively administered with at least one additional therapeutic agent. Examples of additional therapeutic agents include, but are not limited to, anti-cancer drugs, anti-inflammatories, antihistamines and decongestants.

4.1. SOLID FORMS COMPRISING COMPOUND A

Certain embodiments herein provide solid forms comprising Compound A, which has the chemical structure shown above. Racemic 2-[1-(3-Ethoxy-4-methoxyphenyl)-2-methylsulfonylethyl]-4-acetylaminoisoindoline-1,3-dione is readily prepared using the methods in U.S. Pat. No. 6,020,358, which is incorporated herein by reference. Compound A, which is the (+) enantiomer of 2-[1-(3-Ethoxy-4-methoxyphenyl)-2-methylsulfonylethyl]-4-acetylaminoisoindoline-1,3-dione, can be prepared according to any method apparent to those of skill in the art, including the methods described in U.S. Pat. No. 6,962,940, which is incorporated herein by reference.

Solid forms comprising Compound A include single-component and multiple-component forms, including crystal forms and amorphous forms, and including, but not limited to, polymorphs, solvates, hydrates, co-crystals and clathrates. Particular embodiments herein provide single-component amorphous solid forms of Compound A. Particular embodiments herein provide single-component crystalline solid forms of Compound A. Particular embodiments herein provide multiple-component amorphous forms comprising Compound A. Particular embodiments herein provide multiple-component crystalline solid forms comprising Compound A. Multiple-component solid forms provided herein include solid forms which may be described by the terms salt, co-crystal, hydrate, solvate, clathrate and/or polymorph, and include solid forms which may be described by one or more of these terms.

Solid forms comprising Compound A can be prepared by the methods described herein, including the methods described in the Examples below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal countermolecules, desolvation, dehydration, rapid cooling, slow cooling, exposure to solvent and/or water, drying, including, e.g., vacuum drying, vapor diffusion, sublimation, grinding (including, e.g., cryo-grinding, solvent-drop grinding or liquid assisted grinding), microwave-induced precipitation, sonication-induced precipitation, laser-induced precipitation and precipitation from a supercritical fluid. The particle size of the resulting solid forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Certain embodiments herein provide compositions comprising one or more of the solid forms. Certain embodiments provide compositions of one or more solid forms in combination with other active ingredients. Certain embodiments provide methods of using these compositions in the treatment, prevention or management of diseases and disorders including, but not limited to, the diseases and disorders provided herein.

In addition to solid forms comprising Compound A, provided herein are solid forms comprising prodrugs of Compound A.

Solid forms provided herein may also comprise unnatural proportions of atomic isotopes at one or more of the atoms in Compound A. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of Compound A, whether radioactive or not, are intended to be encompassed within the scope of the embodiments provided herein.

4.1.1. Form A of Compound A

Certain embodiments herein provide the Form A crystal form of Compound A. In certain embodiments, Form A of Compound A can be obtained from various solvents, including, but not limited to, solvent systems comprising acetone, ethanol, and mixtures thereof. In certain embodiments, Form A can be obtained using a fast cooling crystallization process.

In certain embodiments, Form A of Compound A may be characterized by X-ray powder diffraction analysis. A representative XRPD pattern of Form A of Compound A is provided in FIG. 1. In certain embodiments, Form A of Compound A is characterized by XRPD peaks located at one, two, three, four, five, six, seven, eight, nine, ten, eleven or twelve of the following approximate positions: 8.1, 14.4, 15.2, 17.4, 18.4, 19.2, 20.5, 22.8, 23.2 23.6, 24.5, 25.1 degrees 2θ. In certain embodiments, Form A of Compound A is characterized by an XRPD pattern which matches the pattern exhibited in FIG. 1. In certain embodiments, Form A of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form A pattern provided herein.

Figure 2:
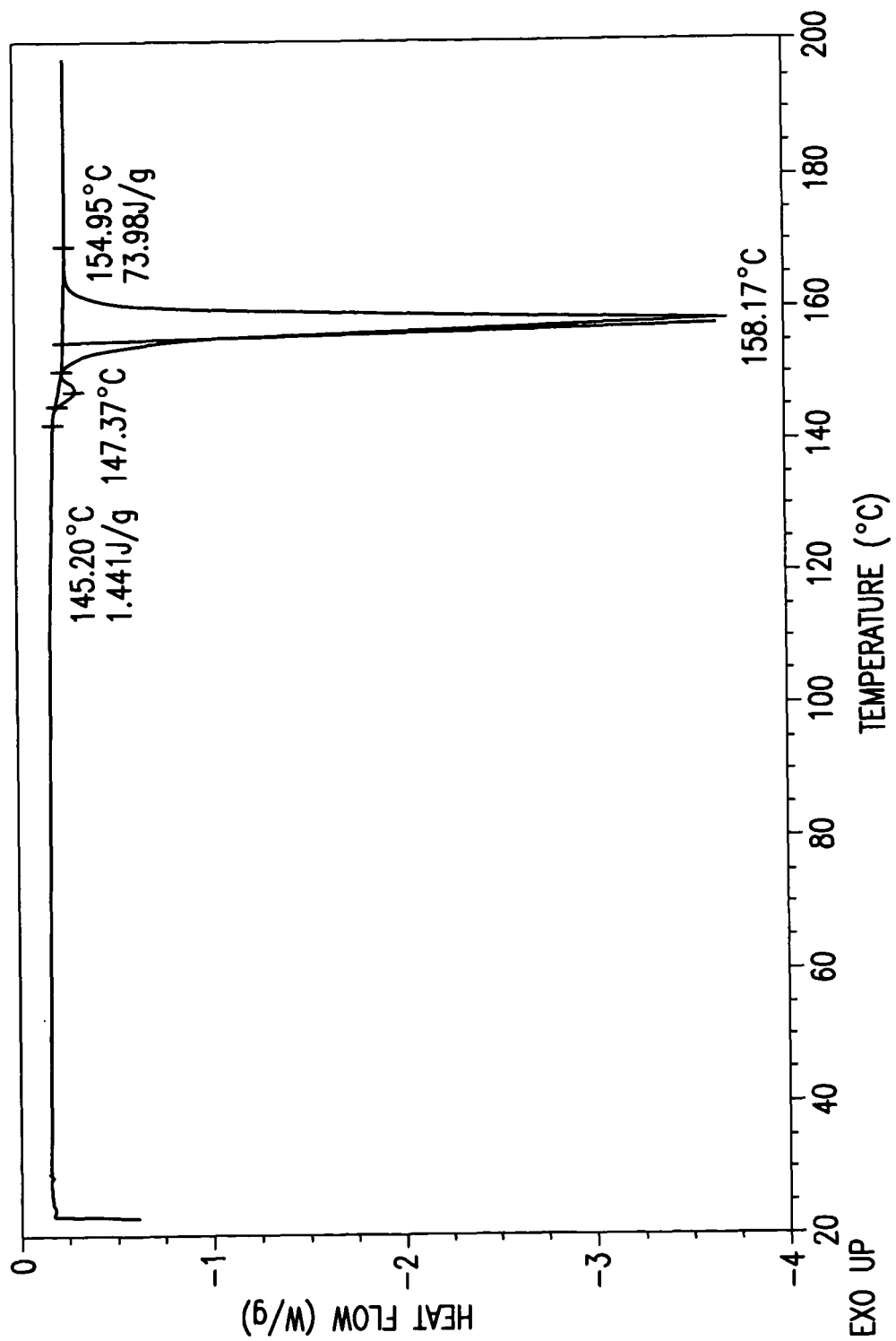
Figure 3:
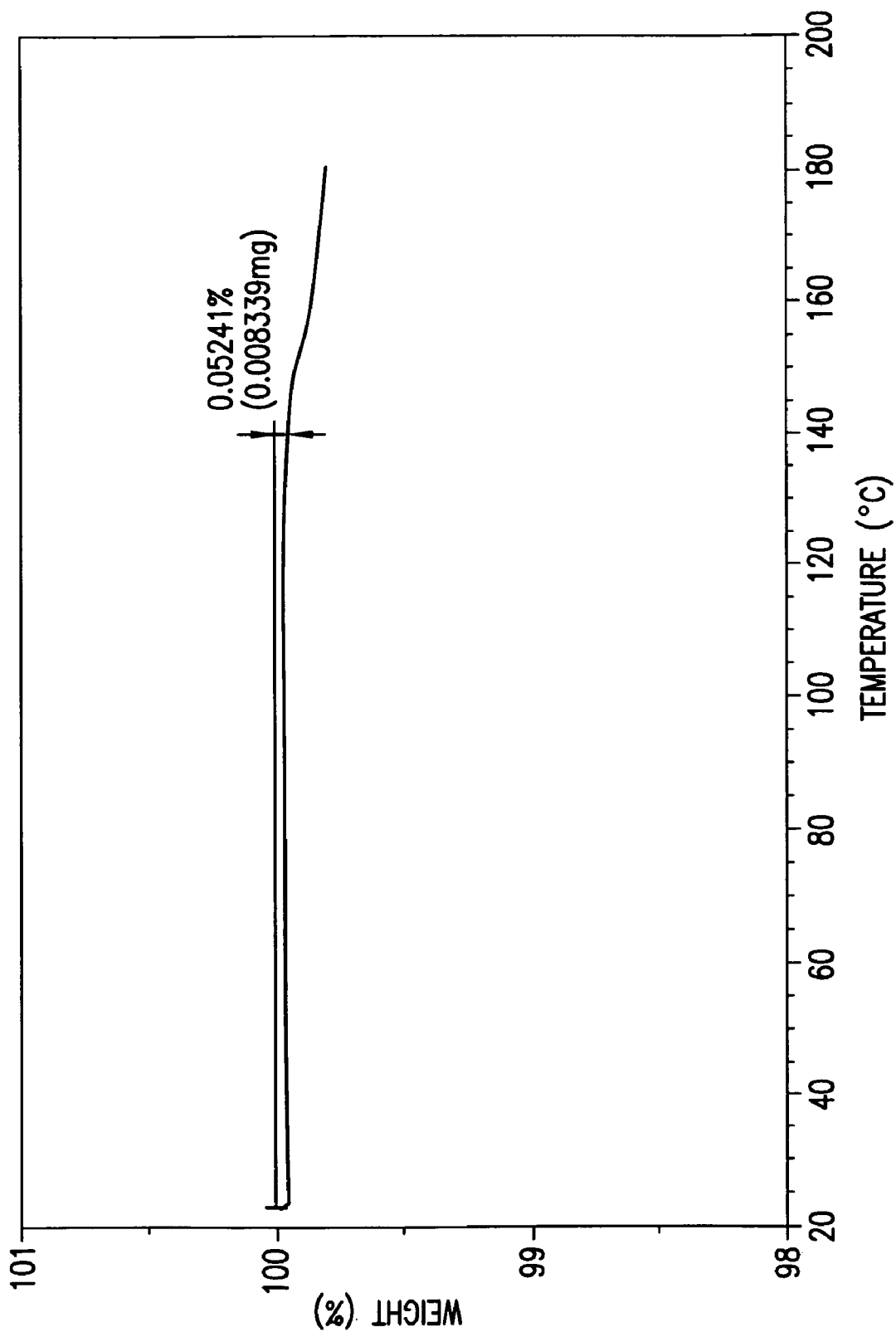

In certain embodiments, Form A of Compound A may be characterized by thermal analysis. A representative DSC plot for Form A of Compound A is shown in FIG. 2. In certain embodiments, Form A is characterized by a DSC plot comprising an endothermic event with an onset temperature of about 145° C. In certain embodiments, Form A is characterized by a DSC plot further comprising an endothermic event with an onset temperature of about 155° C. A representative TGA plot for Form A of Compound A is shown in FIG. 3. In certain embodiments, Form A is characterized by a TGA plot comprising a mass loss of less than about 1%, e.g., about 0.05%, of the total mass of the sample upon heating from about 25° C. to about 140° C. In certain embodiments, Form A of Compound A does not contain substantial amounts of either water or other solvent in the crystal lattice. In certain embodiments, Form A is unsolvated. In certain embodiments, Form A is anhydrous.

Figure 4:
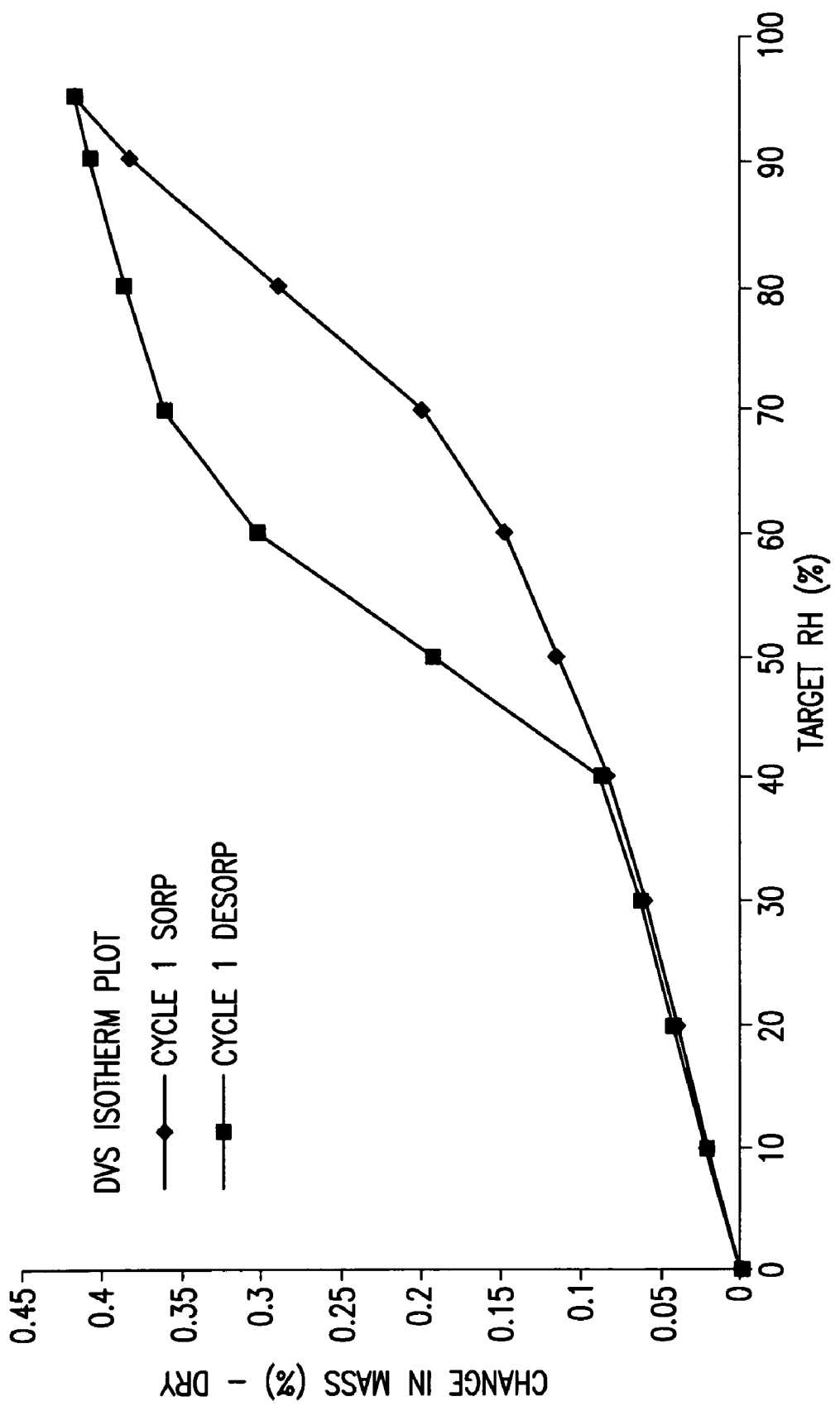

In certain embodiments, Form A of Compound A may be characterized by moisture sorption analysis. A representative moisture sorption isotherm plot is shown in FIG. 4. In certain embodiments, when the relative humidity ("RH") is increased from about 0% to about 95% RH, Form A exhibits a mass change of less than about 1%, e.g., about 0.4%, of the starting mass of the sample. In certain embodiments, mass gained upon adsorption is lost when the RH is decreased back to about 0% RH. Accordingly, in certain embodiments, Form A is substantially nonhygroscopic. In certain embodiments, the XRPD pattern of the Form A material is substantially unchanged following the adsorption/desorption analysis. In certain embodiments, Form A is stable with respect to humidity.

In certain embodiments, Form A of Compound A may be characterized by its stability profile. In certain embodiments, Form A material is stable, e.g., its XRPD pattern remains substantially unchanged, upon exposure to elevated temperature, upon exposure to elevated humidity, upon exposure to one or more solvents, and/or upon compression. In certain embodiments, for example, Form A is stable following exposure to an environment of about 40° C. and about 75% RH environment for about four weeks. In certain embodiments, Form A is stable following exposure to one or more solvent systems comprising, e.g., ethanol, water and/or heptane, at about 40° C. for at least about four weeks. In certain embodiments, Form A converts to Form C of Compound A upon exposure to a solvent including, but not limited to, toluene for four weeks. In certain embodiments, Form A is stable upon compression at about 2000 psi pressure for about one minute.

In certain embodiments, Form A of Compound A may be characterized by particle analysis. In certain embodiments, Form A is characterized as a white powder. In certain embodiments, a sample of Form A comprises particles having a plate-like morphology. In certain embodiments, a sample of Form A comprises particles with a $D_{90}$ of less than about 18 μm. (As used herein, the $D_{90}$ value represents the 90th percentile of the particle size distribution as measured by length; i.e., 90% of the particles have a length of this value or less).

Certain embodiments herein provide Form A of Compound A which is substantially pure. Certain embodiments herein provide Form A of Compound A which is substantially free of other solid forms comprising Compound A including, e.g., Forms B, C, D, E, F, G and/or an amorphous solid form comprising Compound A as provided herein. Certain embodiments herein provide Form A as a mixture of solid forms comprising Compound A, including, e.g., a mixture comprising one or more of the following: Forms B, C, D, E, F, G and an amorphous solid form comprising Compound A as provided herein.

4.1.2. Form B of Compound A

Certain embodiments herein provide the Form B crystal form of Compound A. In certain embodiments, Form B of Compound A can be obtained from various solvents, including, but not limited to, solvent systems comprising 2-propanol, acetone, acetonitrile, ethanol, ethyl acetate, heptane, methanol, methyl ethyl ketone, methyl t-butyl ether, methylene chloride, n-butanol, n-butyl acetate, tetrahydrofuran, toluene, water and mixtures comprising two or more thereof. For example, in certain embodiments, Form B can be obtained by crystallization from a solvent system comprising 1:1 ethanol:water, e.g., by a process comprising evaporation of the 1:1 ethanol:water solvent system at about 25° C., followed by isolation of Form B. For example, in certain embodiments, Form B can be obtained by crystallization from a solvent system comprising 1:1 acetone:ethanol, e.g., by a process comprising slurrying a solid form comprising Compound A in 1:1 acetone:ethanol at about 25° C. for about 2 days, followed by isolation of Form B.

Figure 5:
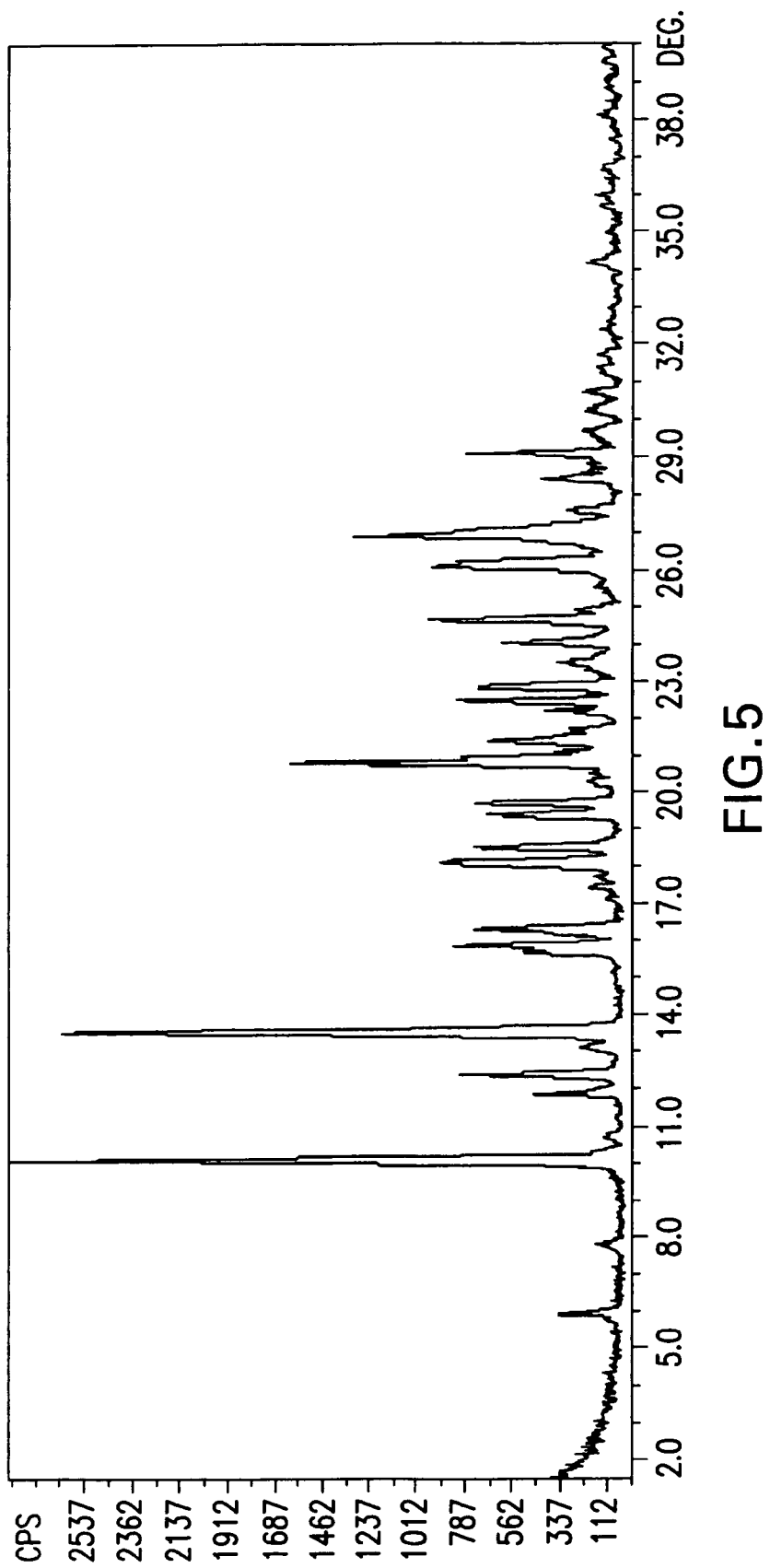

In certain embodiments, Form B of Compound A may be characterized by X-ray powder diffraction analysis. A representative XRPD pattern of Form B of Compound A is provided in FIG. 5. In certain embodiments, Form B of Compound A is characterized by XRPD peaks located at one, two, three, four, five, six, seven, eight, nine, ten, eleven or twelve of the following approximate positions: 10.1, 12.4, 13.5, 15.7, 16.3, 18.1, 20.7, 22.5, 24.7, 26.2, 26.9, 29.1 degrees 2θ. In certain embodiments, Form B of Compound A is characterized by an XRPD pattern which matches the pattern exhibited in FIG. 5. In certain embodiments, Form B of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form B pattern provided herein.

Figure 6:
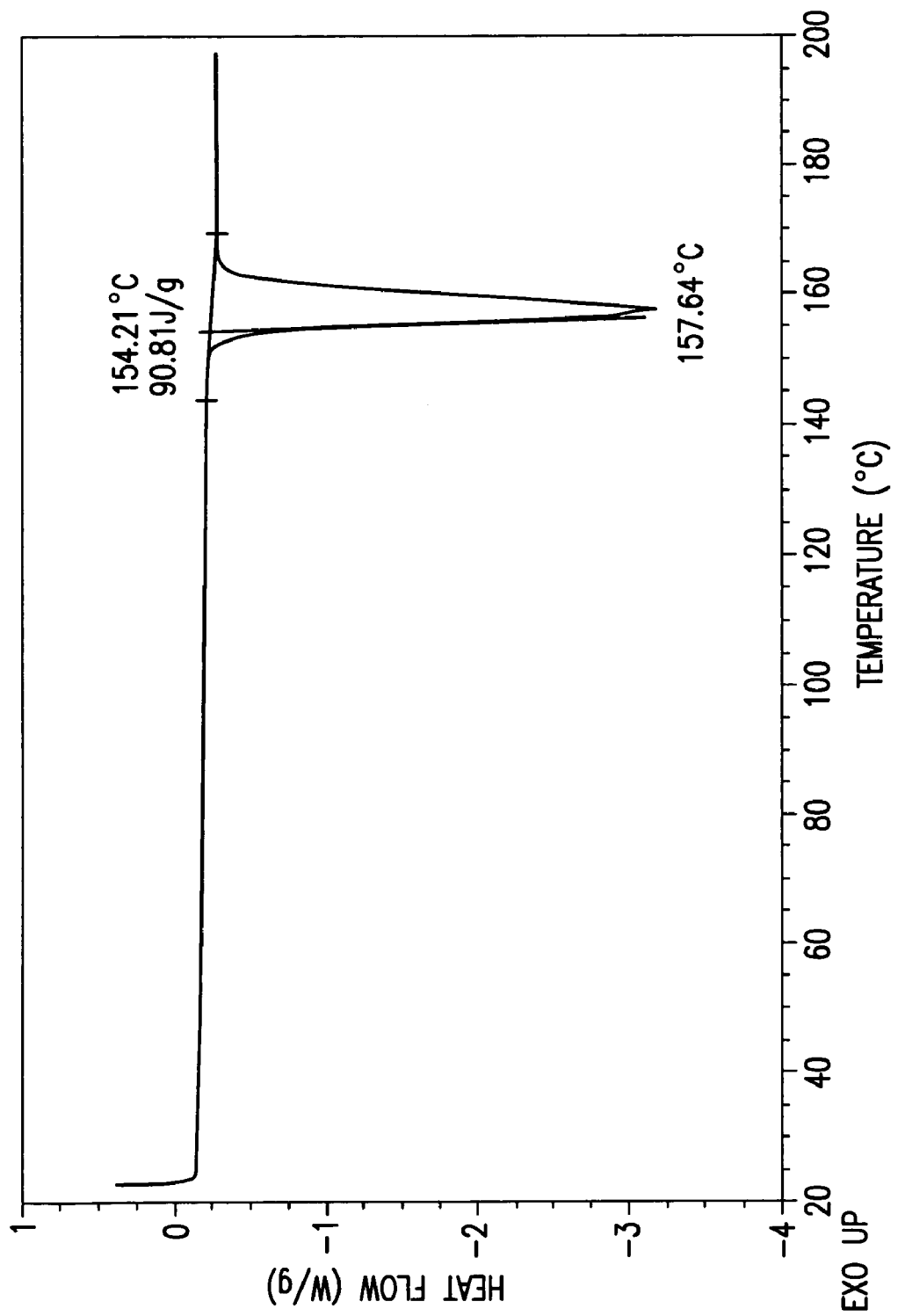
Figure 7:
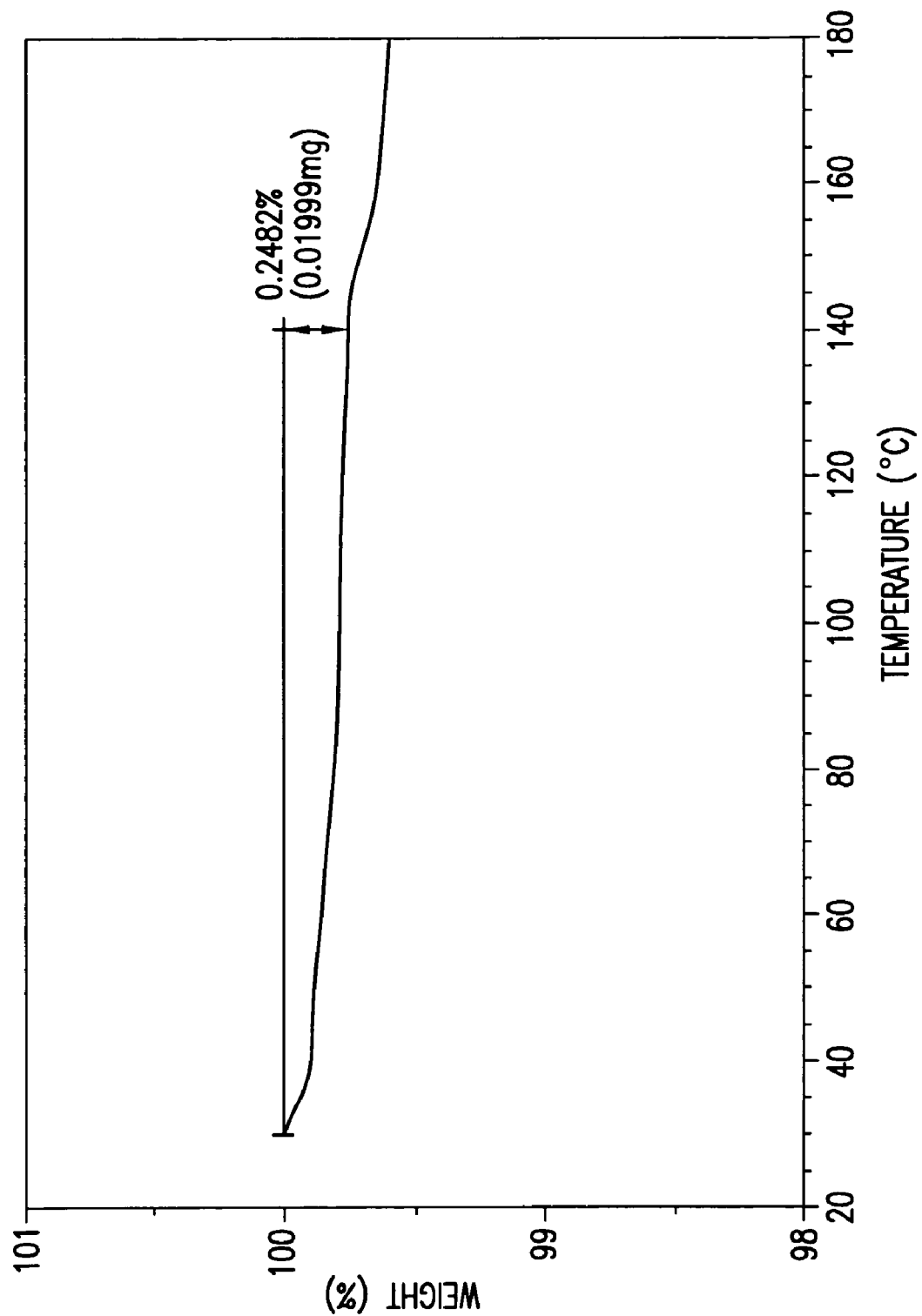

In certain embodiments, Form B of Compound A may be characterized by thermal analysis. A representative DSC plot for Form B of Compound A is shown in FIG. 6. In certain embodiments, Form B is characterized by a DSC plot comprising an endothermic event with an onset temperature of about 154° C. A representative TGA plot for Form B of Compound A is shown in FIG. 7. In certain embodiments, Form B is characterized by a TGA plot comprising a mass loss of less than about 1%, e.g., about 0.25%, of the total mass of the sample upon heating from about 25° C. to about 140° C. In certain embodiments, Form B of Compound A does not contain substantial amounts of either water or other solvent in the crystal lattice. In certain embodiments, Form B is anhydrous. In certain embodiments, Form B is unsolvated.

Figure 8:
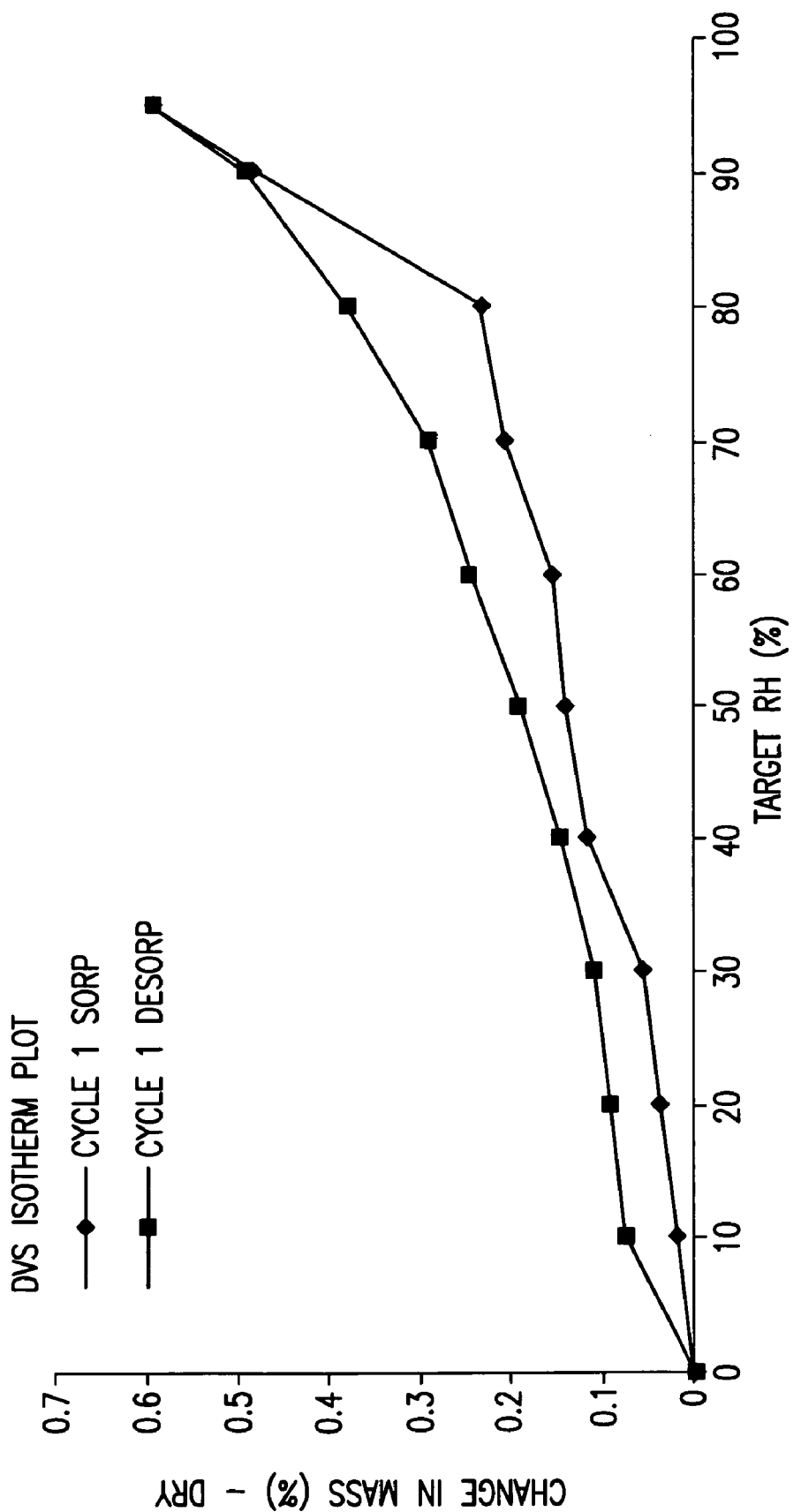

In certain embodiments, Form B of Compound A may be characterized by moisture sorption analysis. A representative moisture sorption isotherm plot is shown in FIG. 8. In certain embodiments, when the RH is increased from about 0% to about 95% RH, Form B exhibits a mass change of less than about 1%, e.g., about 0.6%, of the starting mass of the sample. In certain embodiments, mass gained upon adsorption is lost when the RH is decreased back to about 0% RH. In certain embodiments, Form B is substantially nonhygroscopic. In certain embodiments, the XRPD pattern of Form B material is substantially unchanged following the adsorption/desorption analysis. In certain embodiments, Form B is stable with respect to humidity.

In certain embodiments, Form B of Compound A may be characterized by its stability profile. In certain embodiments, Form B material is stable, e.g., its XRPD pattern remains substantially unchanged, upon exposure to elevated temperature, upon exposure to elevated humidity, upon exposure to one or more solvents, and/or upon compression. In certain embodiments, for example, Form B is stable following exposure to an environment of about 40° C. and about 75% RH environment for about four weeks. In certain embodiments, Form B is stable following exposure to a solvent system comprising, e.g., ethanol, water or heptane, at about 40° C. for at least about four weeks. In certain embodiments, Form B converts to Form C of Compound A upon exposure to a solvent system comprising, e.g., toluene for about four weeks. In certain embodiments, Form B is stable following compression at about 2000 psi pressure for about one minute.

In certain embodiments, Form B of Compound A may be characterized by particle analysis. In certain embodiments, Form B is characterized as a white powder. In certain embodiments, a sample of Form B comprises particles having a flake-like morphology. In certain embodiments, a sample of Form B comprises particles with a $D_{90}$ of less than about 12 µm.

Certain embodiments herein provide Form B of Compound A which is substantially pure. Certain embodiments herein provide Form B of Compound A which is substantially free of other solid forms comprising Compound A including, e.g., Forms A, C, D, E, F, G and/or an amorphous solid form comprising Compound A as provided herein. Certain embodiments herein provide Form B as a mixture of solid forms comprising Compound A, including, e.g., a mixture comprising one or more of the following: Forms A, C, D, E, F, G and an amorphous solid form comprising Compound A as provided herein.

4.1.3. Form C of Compound A

Certain embodiments herein provide the Form C crystal form of Compound A. In certain embodiments, Form C of Compound A can be obtained from various solvent systems, including, but not limited to, solvent systems comprising acetone, acetonitrile, ethanol, heptane, methanol, methyl ethyl ketone, tetrahydrofuran, toluene, water, and mixtures comprising two or more thereof. For example, in certain embodiments, Form C can be obtained by crystallization from a solvent system comprising toluene, e.g., by a process comprising the use of toluene as an anti-solvent, followed by isolation of Form C.

Figure 9:
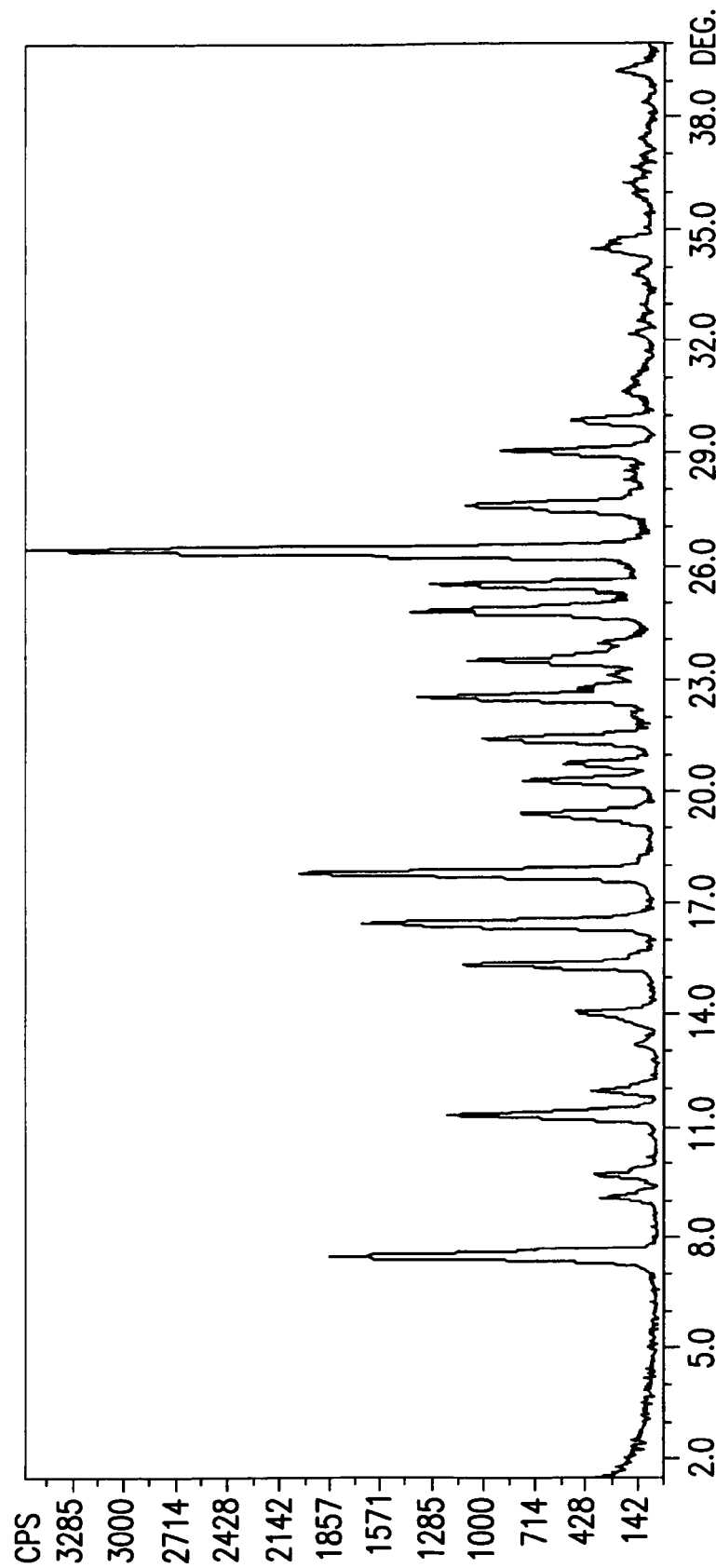

In certain embodiments, Form C of Compound A may be characterized by X-ray powder diffraction analysis. A representative XRPD pattern of Form C of Compound A is provided in FIG. 9. In certain embodiments, Form C of Compound A is characterized by XRPD peaks located at one, two, three, four, five, six, seven, eight, nine, ten, eleven or twelve of the following approximate positions: 7.5, 11.3, 15.3, 16.4, 17.8, 21.4, 22.6, 23.5, 24.8, 25.5, 26.4, 27.6 degrees 2θ. In certain embodiments, Form C of Compound A is characterized by an XRPD pattern which matches the pattern exhibited in FIG. 9. In certain embodiments, Form C of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form C pattern provided herein.

Figure 10:
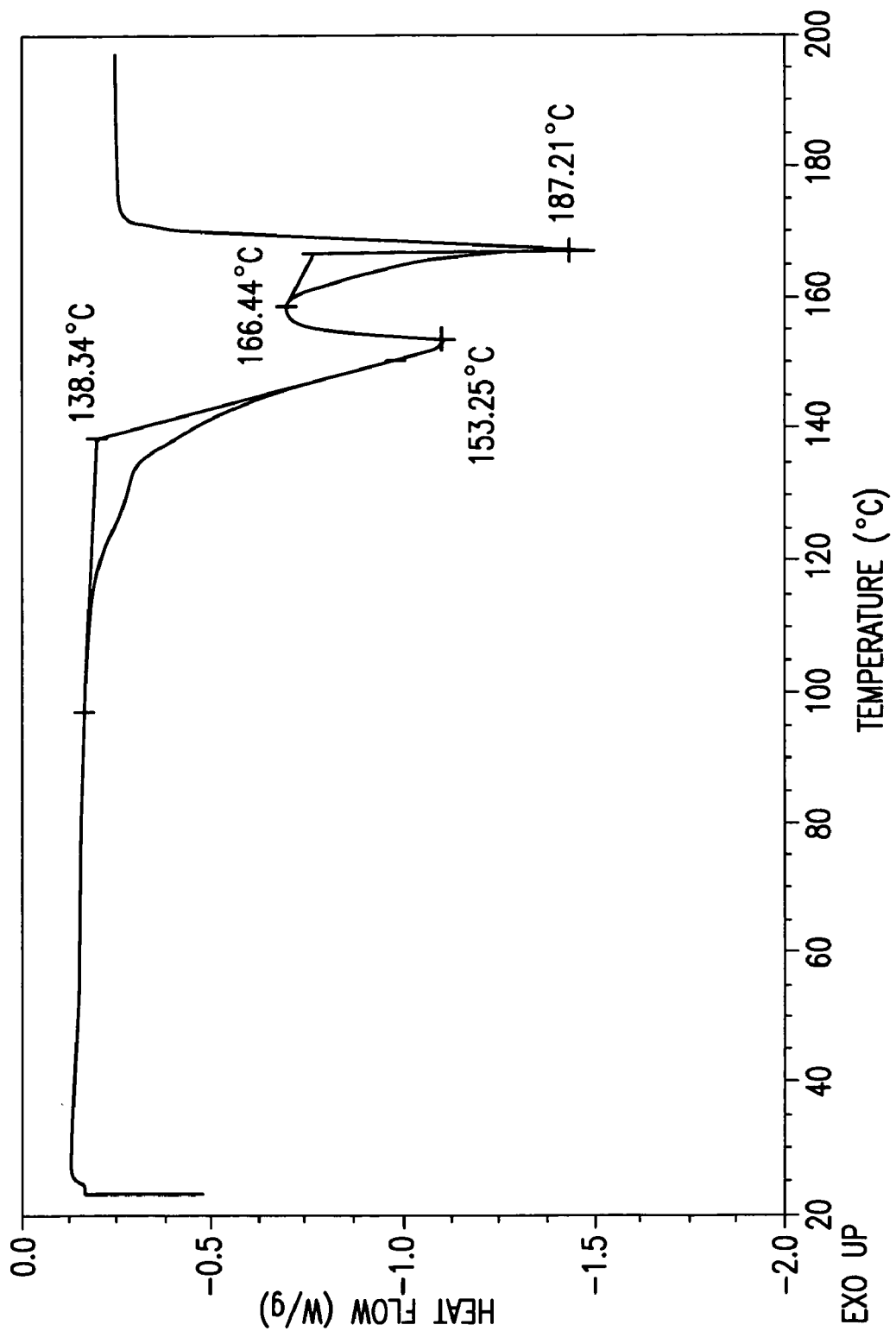
Figure 11:
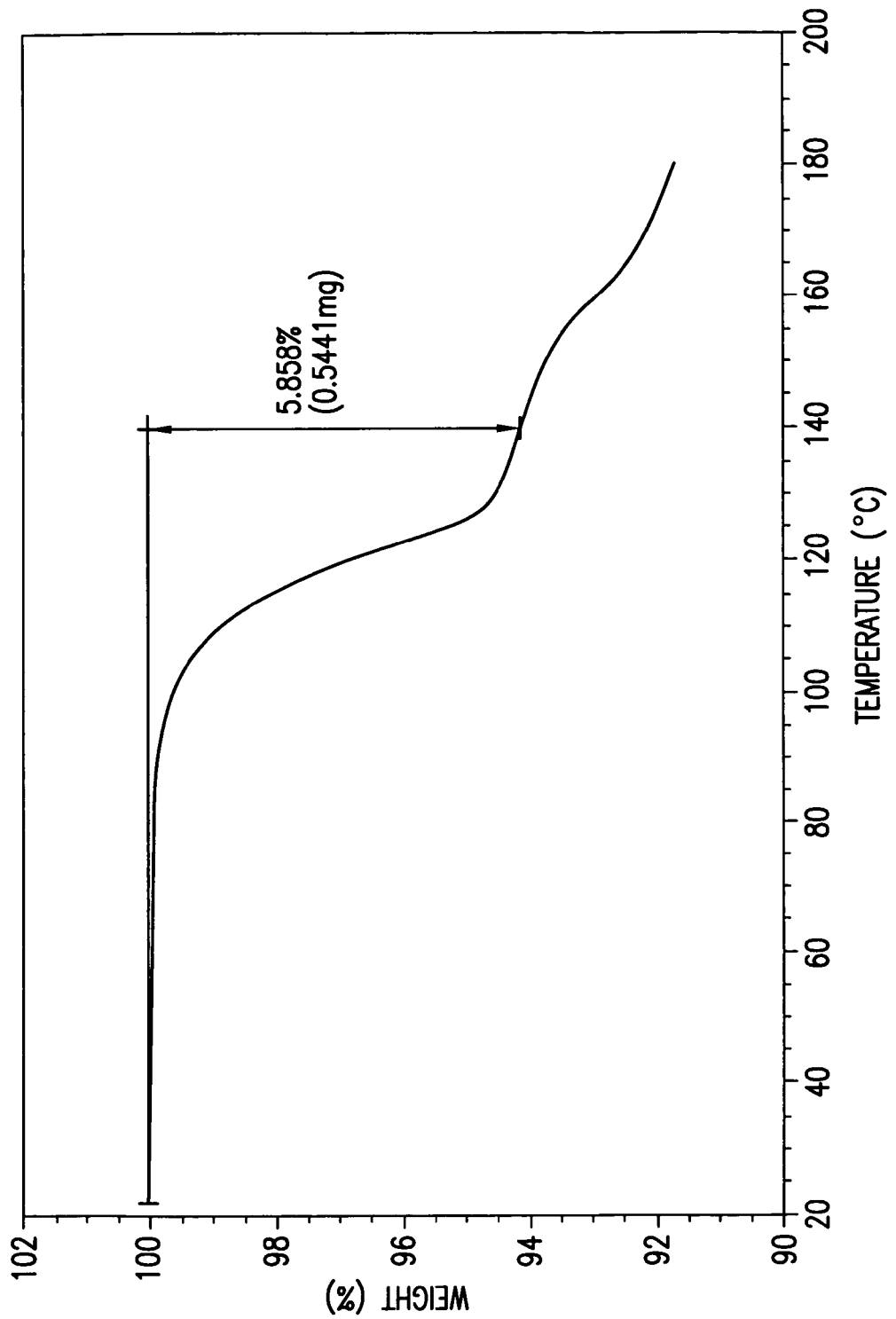

In certain embodiments, Form C of Compound A may be characterized by thermal analysis. A representative DSC plot for Form C of Compound A is shown in FIG. 10. In certain embodiments, Form C is characterized by a DSC plot comprising an endothermic event with an onset temperature of about 138° C. In certain embodiments, a characteristic Form C DSC plot further comprises one or more additional events, such as, e.g., an endothermic event with an onset temperature of about 166° C. A representative TGA plot for Form C of Compound A is shown in FIG. 11. In certain embodiments, Form C is characterized by a TGA plot comprising a mass loss of less than about 10%, e.g., about 5.9%, of the total mass of the sample upon heating from about 25° C. to about 140° C. In certain embodiments, the TGA mass loss event comprises the loss of the solvent toluene, as indicated, e.g., by TG-IR analysis. In certain embodiments, Form C of Compound A is solvated. In certain embodiments, Form C is a toluene solvate. In certain embodiments, the crystal lattice of Form C comprises about three molar equivalents of toluene per mole of Compound A.

Figure 12:
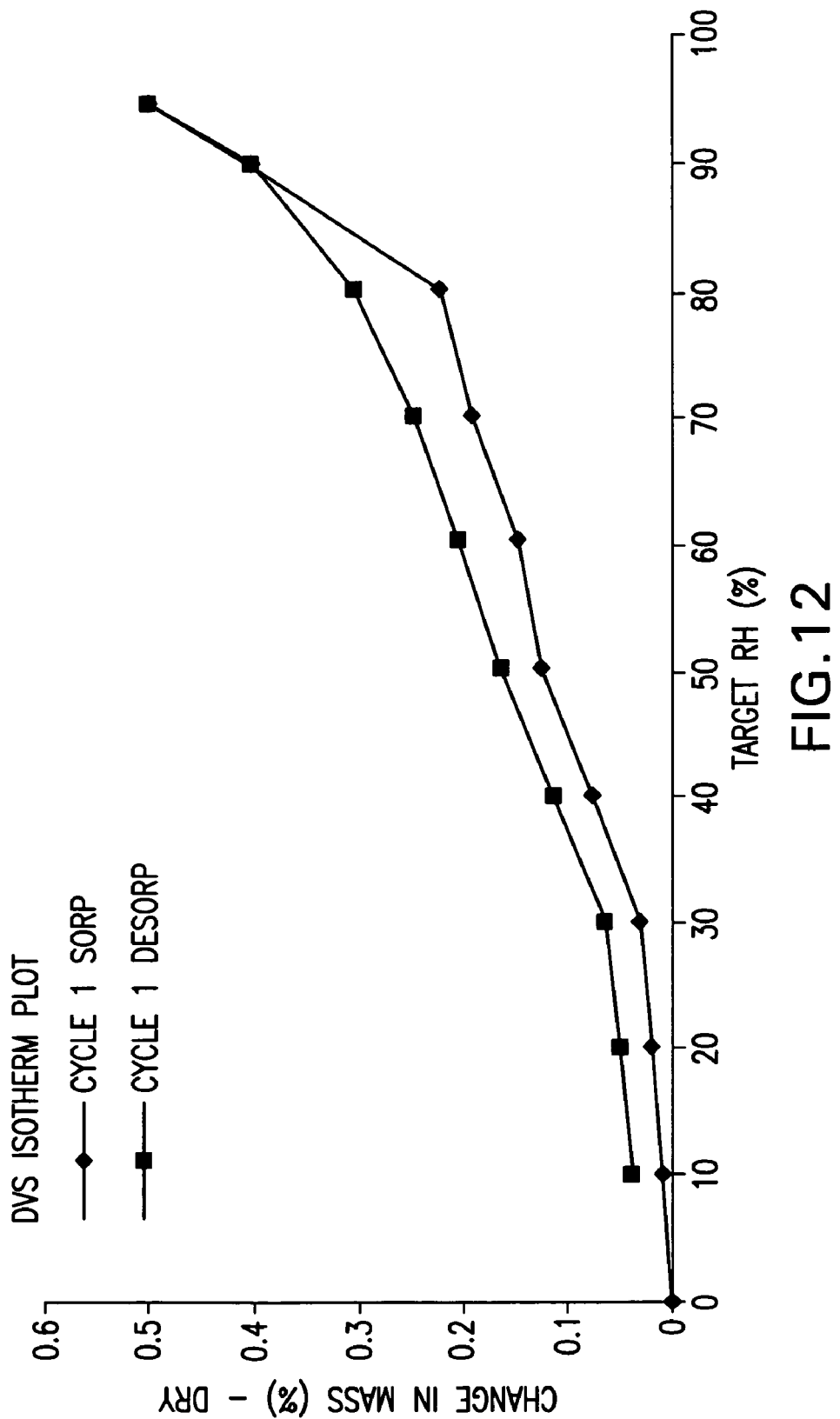

In certain embodiments, Form C of Compound A may be characterized by moisture sorption analysis. A representative moisture sorption isotherm plot is shown in FIG. 12. In certain embodiments, when the RH is increased from about 0% to about 95% RH, Form C exhibits a mass change of less than about 1%, e.g., about 0.5%, of the starting mass of the sample. In certain embodiments, mass gained upon adsorption is lost when the RH is decreased back to about 0% RH. In certain embodiments, Form C is substantially nonhygroscopic. In certain embodiments, the XRPD pattern of Form C material is substantially unchanged following the adsorption/desorption analysis. In certain embodiments, Form C is stable with respect to humidity.

In certain embodiments, Form C of Compound A may be characterized by its stability profile. In certain embodiments, Form C material is stable, e.g., its XRPD pattern remains substantially unchanged, upon exposure to elevated temperature, upon exposure to elevated humidity, upon exposure to one or more solvents, and/or upon compression. In certain embodiments, for example, Form C is stable following exposure to an environment of about 40° C. and about 75% RH environment for about four weeks. In certain embodiments, Form C is stable following exposure to a solvent system comprising, e.g., ethanol, water, heptane or toluene, at about 40° C. for at least about four weeks. In certain embodiments, Form C is stable following compression at about 2000 psi pressure for about one minute.

In certain embodiments, Form C of Compound A may be characterized by particle analysis. In certain embodiments, Form C is characterized as a white powder. In certain embodiments, a sample of Form C comprises particles having a plate-like morphology. In certain embodiments, a sample of Form C comprises particles with a $D_{90}$ of less than about 12 µm.

Certain embodiments herein provide Form C of Compound A which is substantially pure. Certain embodiments herein provide Form C of Compound A which is substantially free of other solid forms comprising Compound A including, e.g., Forms A, B, D, E, F, G and/or an amorphous solid form comprising Compound A as provided herein. Certain embodiments herein provide Form C as a mixture of solid forms comprising Compound A, including, e.g., a mixture comprising one or more of the following: Forms A, B, D, E, F, G and an amorphous solid form comprising Compound A as provided herein.

4.1.4. Form D of Compound A

Certain embodiments herein provide the Form D crystal form of Compound A. In certain embodiments, Form D of Compound A can be obtained from various solvents, including, but not limited to, solvent systems comprising methylene chloride. For example, in certain embodiments, Form D can be obtained by crystallization from a solvent system comprising methylene chloride, e.g., by a process comprising the evaporation of methylene chloride, followed by isolation of Form D.

Figure 13:
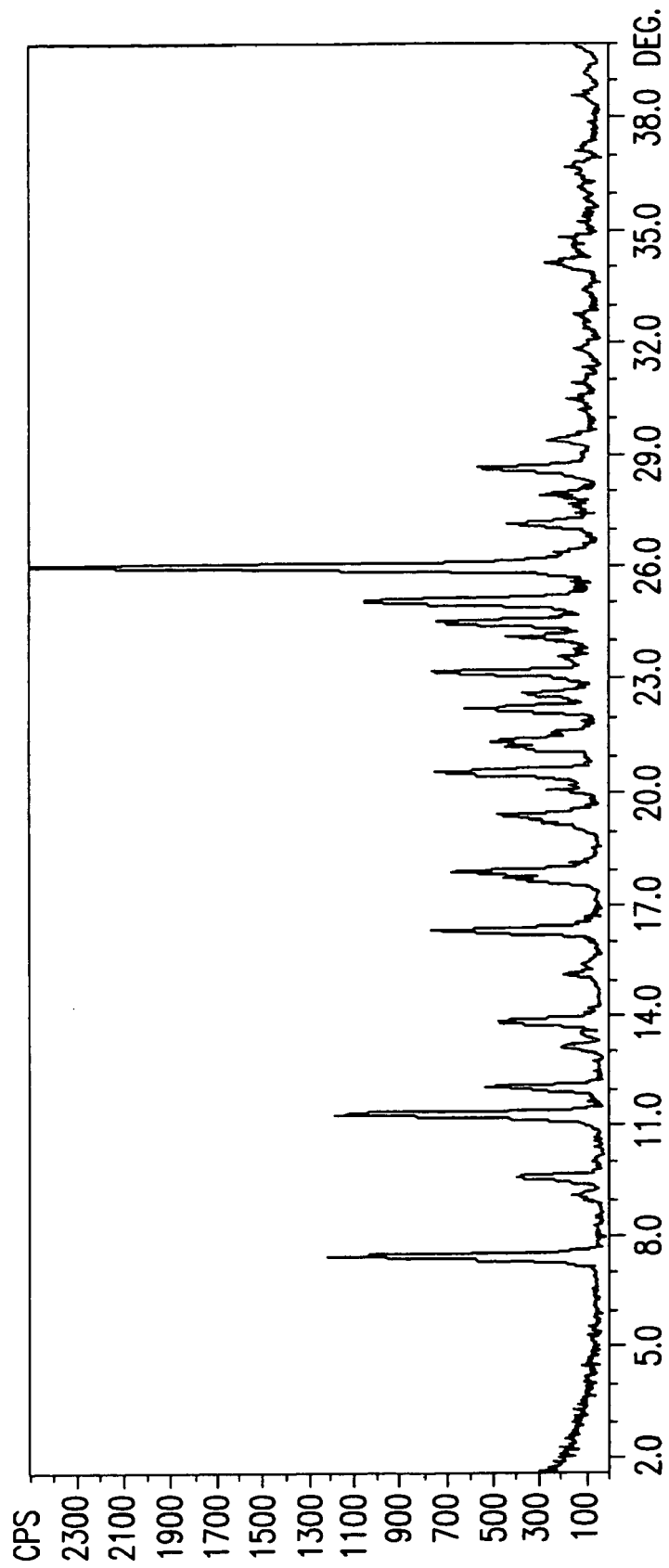

In certain embodiments, Form D of Compound A may be characterized by X-ray powder diffraction analysis. A representative XRPD pattern of Form D of Compound A is provided in FIG. 13. In certain embodiments, Form D of Compound A is characterized by XRPD peaks located at one, two, three, four, five, six, seven, eight, nine, ten, eleven or twelve of the following approximate positions: 7.5, 9.6, 11.3, 13.9, 16.3, 17.7, 20.5, 23.2, 24.6, 25.2, 26.0, 28.8 degrees 2θ. In certain embodiments, Form D of Compound A is characterized by an XRPD pattern which matches the pattern exhibited in FIG. 13. In certain embodiments, Form D of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form D pattern provided herein.

Figure 14:
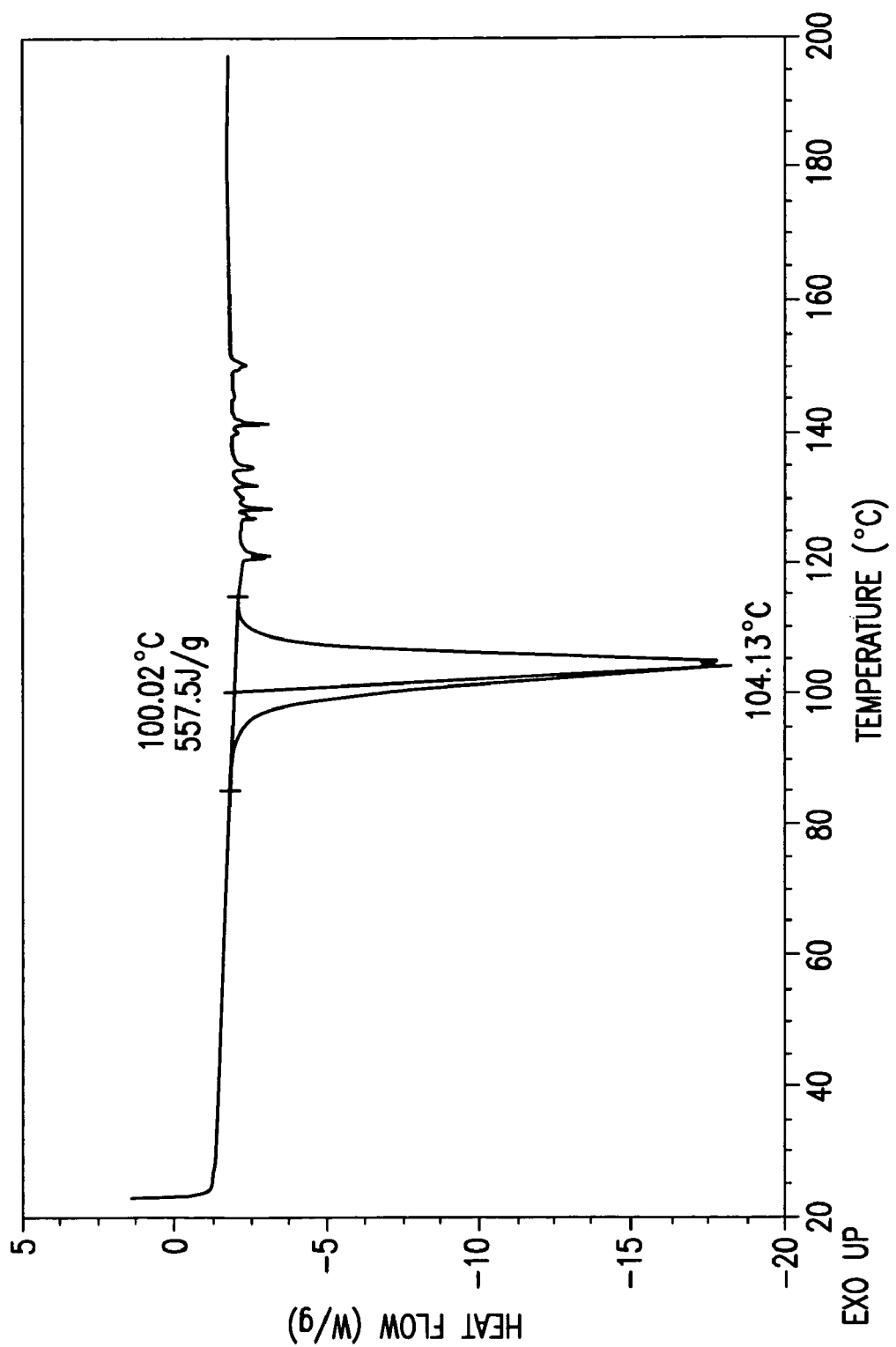
Figure 15:
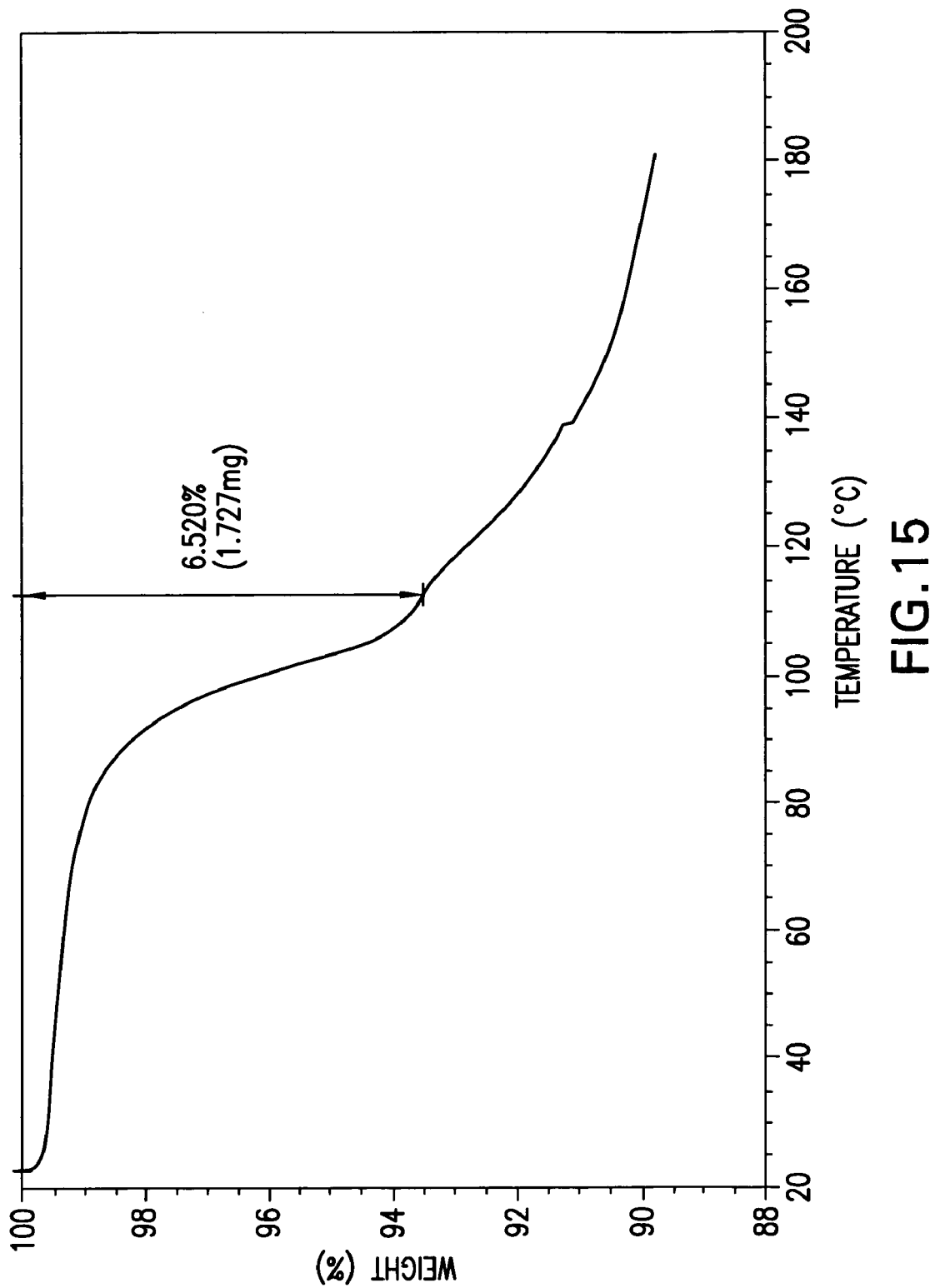

In certain embodiments, Form D of Compound A may be characterized by thermal analysis. A representative DSC plot for Form D of Compound A is shown in FIG. 14. In certain embodiments, Form D is characterized by a DSC plot comprising an endothermic event with an onset temperature of about 100° C. A representative TGA plot for Form D of Compound A is shown in FIG. 15. In certain embodiments, Form D is characterized by a TGA plot comprising a mass loss of less than about 10%, e.g., about 6.5%, of the total mass of the sample upon heating from about 25° C. to about 110° C. In certain embodiments, the TGA mass loss event comprises the loss of the solvent methylene chloride (i.e. dichloromethane), as indicated, e.g., by TG-IR analysis. In certain embodiments, Form D of Compound A is solvated. In certain embodiments, Form D is a methylene chloride solvate. In certain embodiments, the crystal lattice of Form D comprises about 2.5 molar equivalents of methylene chloride per mole of Compound A.

Figure 16:
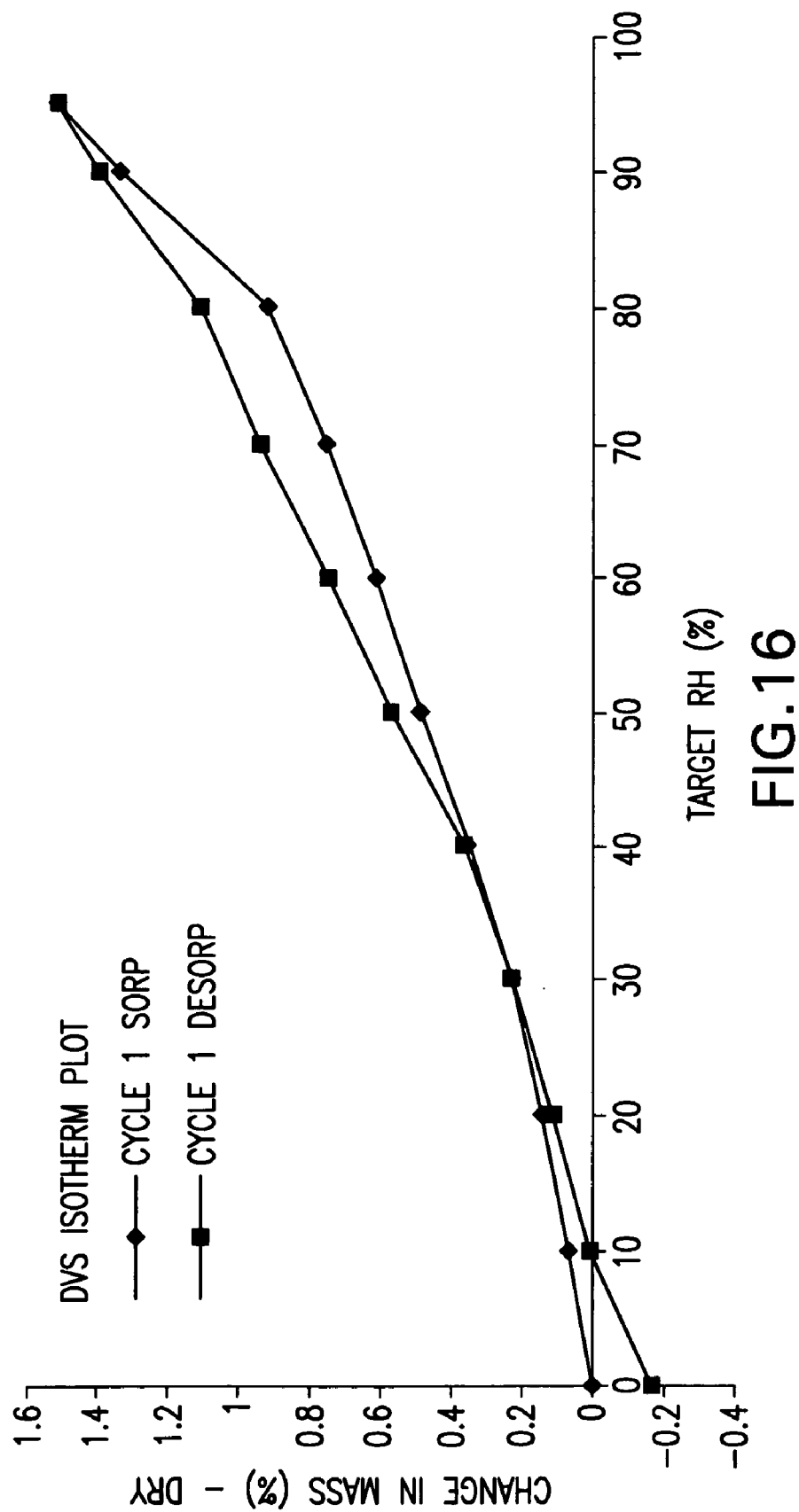

In certain embodiments, Form D of Compound A may be characterized by moisture sorption analysis. A representative moisture sorption isotherm plot is shown in FIG. 16. In certain embodiments, when the RH is increased from about 0% to about 95% RH, Form D exhibits a mass change of less than about 3%, e.g., about 1.5%, of the starting mass of the sample. In certain embodiments, mass gained upon adsorption is lost when the RH is decreased back to about 0% RH. Accordingly, in certain embodiments, Form D is slightly hygroscopic. In certain embodiments, the XRPD pattern of Form D material is substantially unchanged following the adsorption/desorption analysis. In certain embodiments, Form D is stable with respect to humidity.

In certain embodiments, Form D of Compound A may be characterized by its stability profile. In certain embodiments, Form D material is stable, e.g., its XRPD pattern remains substantially unchanged, upon compression. For example, in certain embodiments, Form D is stable following compression at about 2000 psi pressure for about one minute. In certain embodiments, Form D is stable following exposure to an environment of about 40° C. and about 75% RH environment for about four weeks, although, in certain embodiments, the resulting peak intensity of the Form D XRPD pattern is reduced. In certain embodiments, this reduction in XRPD peak intensity results from the formation of amorphous material comprising Compound A. In certain embodiments, Form D converts to Form B of Compound A upon exposure to a solvent system comprising, e.g., heptane, ethanol and/or water at about 40° C. for about four weeks. In certain embodiments, Form D converts to Form C of Compound A upon exposure to a solvent system comprising toluene at about 40° C. for about four weeks.

In certain embodiments, Form D of Compound A may be characterized by particle analysis. In certain embodiments, Form D is characterized as a white powder. In certain embodiments, a sample of Form D comprises particles having a flake-like morphology. In certain embodiments, a sample of Form D comprises particles with a $D_{90}$ of less than about 18 µm.

Certain embodiments herein provide Form D of Compound A which is substantially pure. Certain embodiments herein provide Form D of Compound A which is substantially free of other solid forms comprising Compound A including, e.g., Forms A, B, C, E, F, G and/or an amorphous solid form comprising Compound A as provided herein. Certain embodiments herein provide Form D as a mixture of solid forms comprising Compound A, including, e.g., a mixture comprising one or more of the following: Forms A, B, C, E, F, G and an amorphous solid form comprising Compound A as provided herein.

4.1.5. Form E of Compound A

Certain embodiments herein provide the Form E crystal form of Compound A. In certain embodiments, Form E of Compound A can be obtained from various solvents, including, but not limited to, solvent systems comprising acetone, acetonitrile, heptane, methylene chloride, and mixtures comprising two or more thereof. For example, in certain embodiments, Form E can be obtained by crystallization from a solvent system comprising acetonitrile, e.g., by a process comprising the evaporation of acetonitrile, followed by isolation of Form E.

Figure 17:
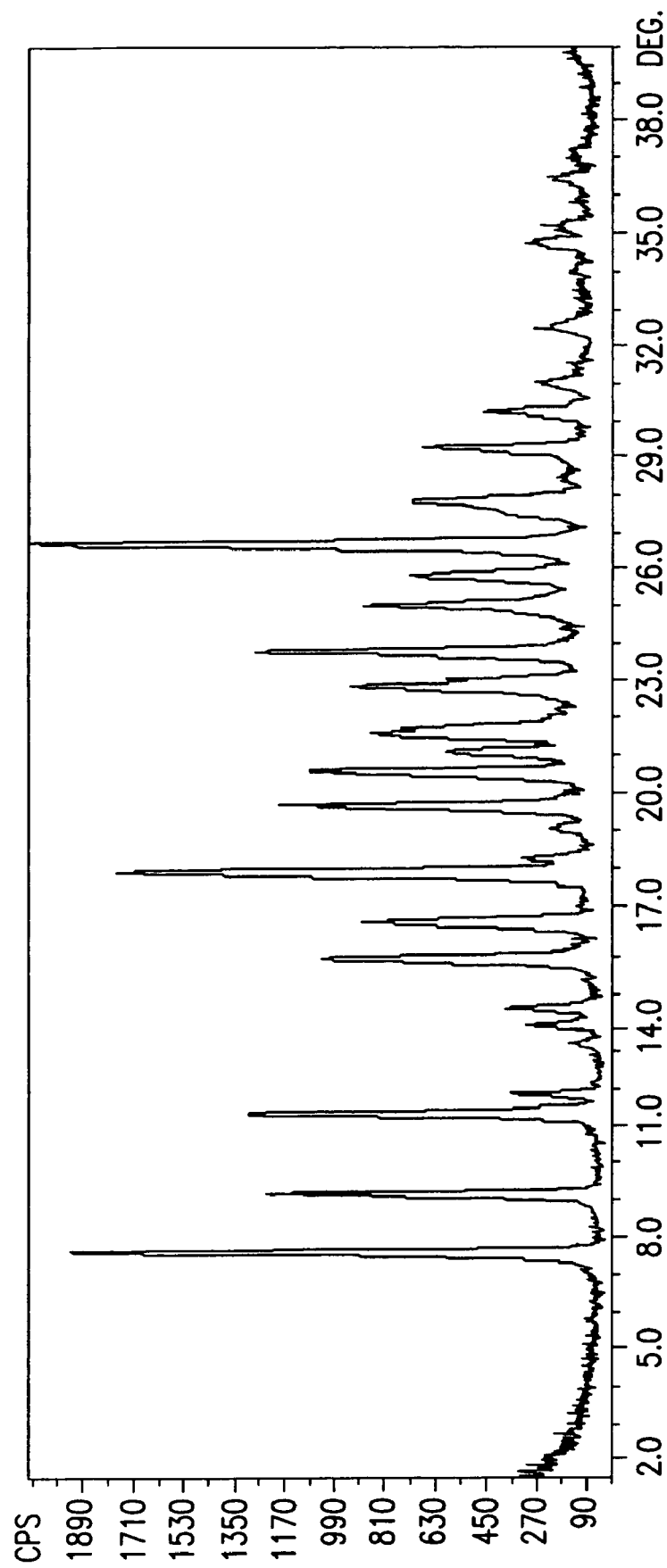

In certain embodiments, Form E of Compound A may be characterized by X-ray powder diffraction analysis. A representative XRPD pattern of Form E of Compound A is provided in FIG. 17. In certain embodiments, Form E of Compound A is characterized by XRPD peaks located at one, two, three, four, five, six, seven, eight, nine, ten, eleven or twelve of the following approximate positions: 7.6, 9.2, 11.4, 15.5, 16.5, 17.9, 19.6, 20.5, 21.6, 22.8, 23.8, 26.6 degrees 2θ. In certain embodiments, Form E of Compound A is characterized by an XRPD pattern which matches the pattern exhibited in FIG. 17. In certain embodiments, Form E of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form E pattern provided herein.

Figure 18:
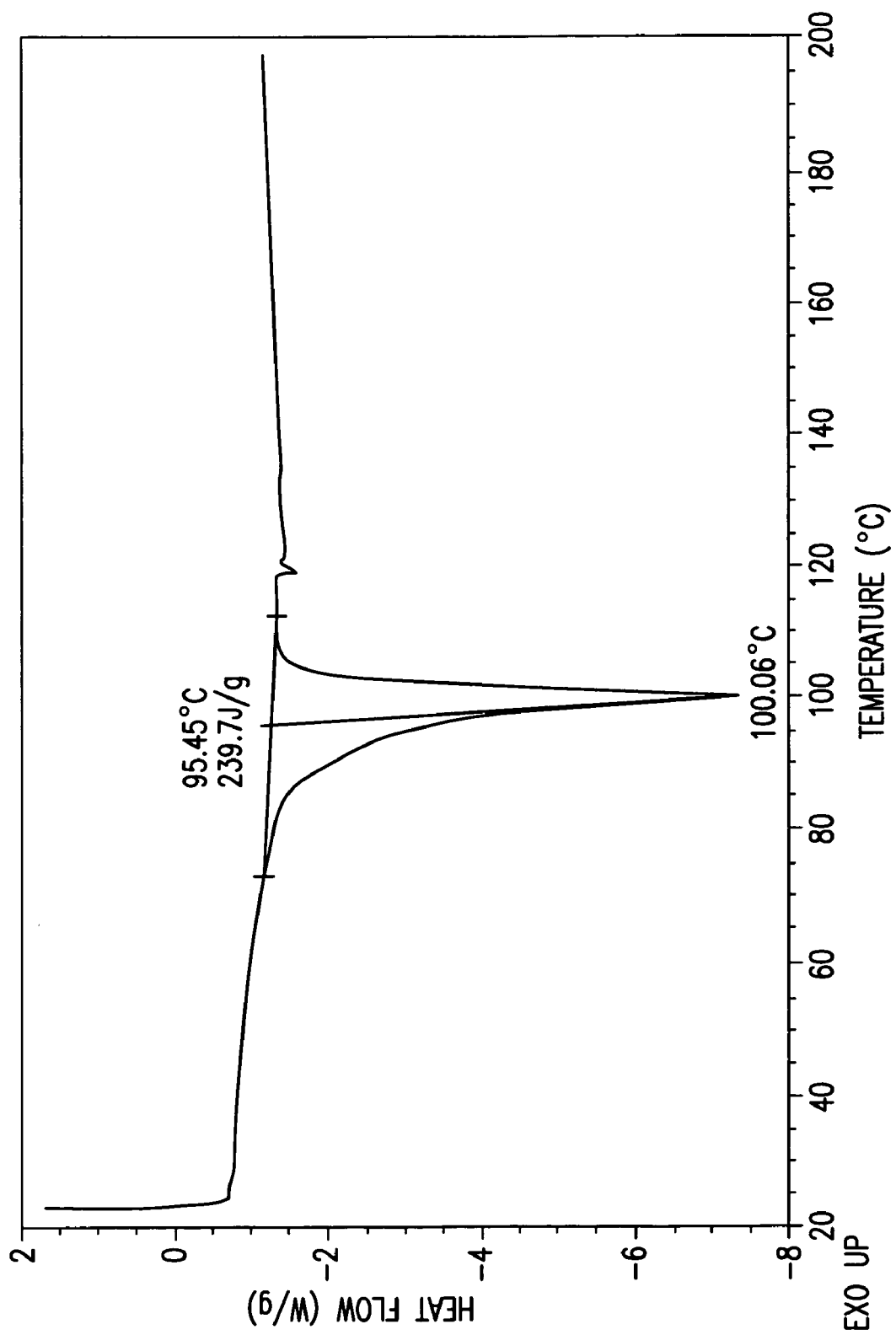
Figure 19:
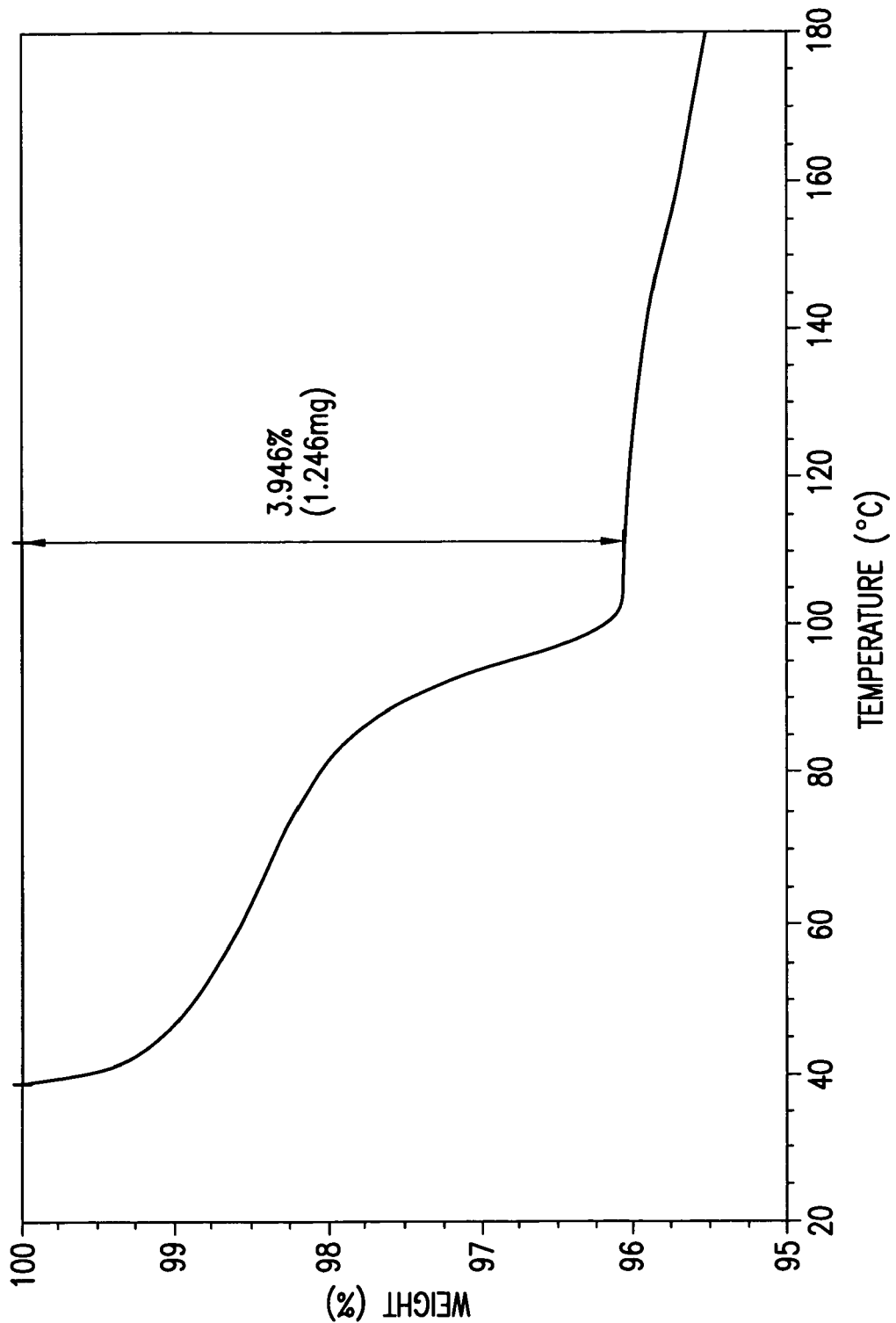

In certain embodiments, Form E of Compound A may be characterized by thermal analysis. A representative DSC plot for Form E of Compound A is shown in FIG. 18. In certain embodiments, Form E is characterized by a DSC plot comprising an endothermic event with an onset temperature of about 95° C. A representative TGA plot for Form E of Compound A is shown in FIG. 19. In certain embodiments, Form E is characterized by a TGA plot comprising a mass loss of less than about 8%, e.g., about 4.0%, of the total mass of the sample upon heating from about 25° C. to about 110° C. In certain embodiments, the TGA mass loss event comprises the loss of the solvent acetonitrile, as indicated, e.g., by TG-IR analysis. In certain embodiments, Form E of Compound A is solvated. In certain embodiments, Form E is an acetonitrile solvate. In certain embodiments, the crystal lattice of Form E comprises about 2.5 molar equivalents of acetonitrile per mole of Compound A.

Figure 20:
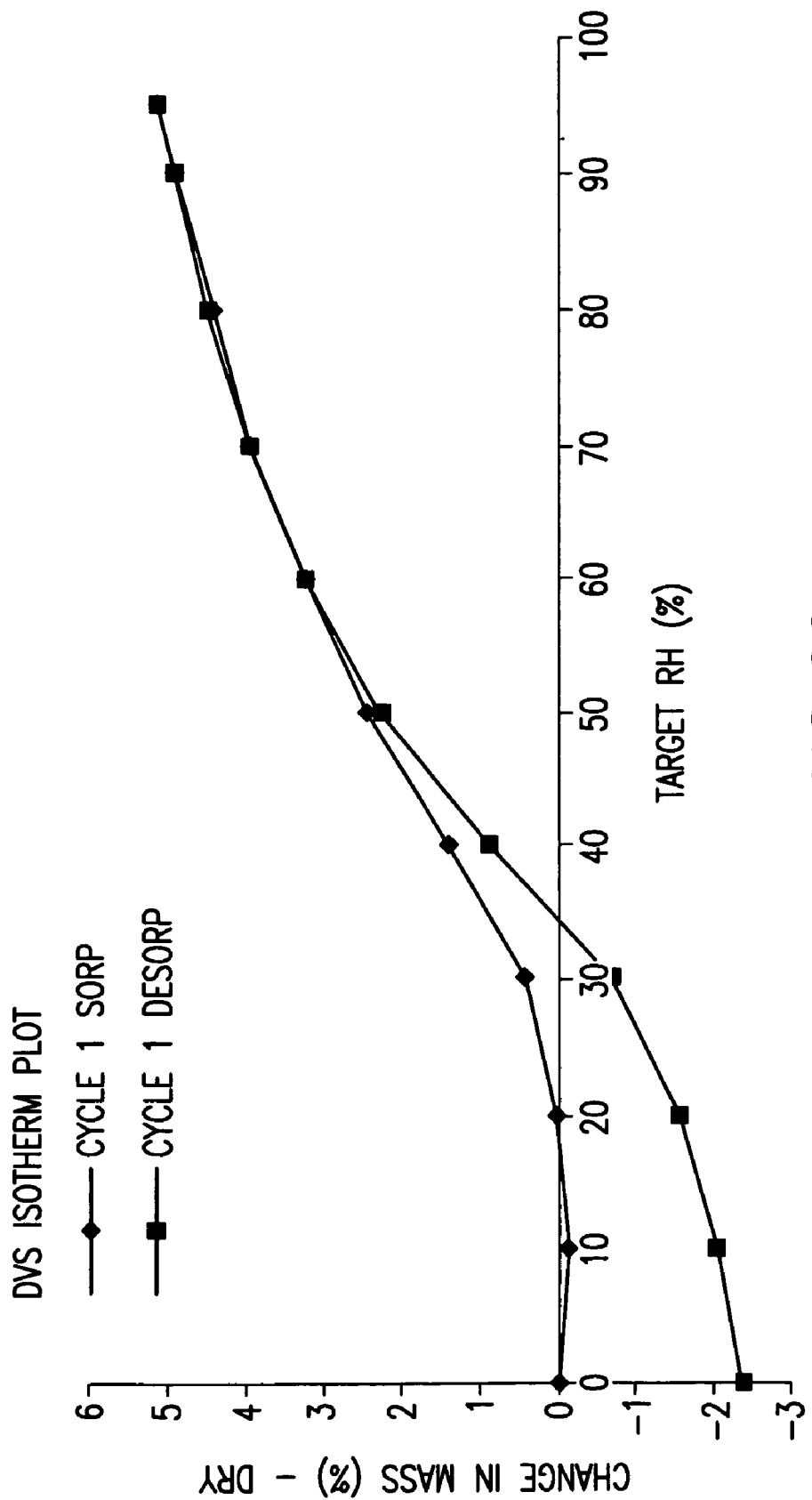

In certain embodiments, Form E of Compound A may be characterized by moisture sorption analysis. A representative moisture sorption isotherm plot is shown in FIG. 20. In certain embodiments, when the RH is increased from about 0% to about 95% RH, Form E exhibits a mass change of less than about 10%, e.g., about 5.1%, of the starting mass of the sample. In certain embodiments, mass gained upon adsorption is lost when the RH is decreased back to about 0% RH. In certain embodiments, Form E is hygroscopic. In certain embodiments, the XRPD pattern of Form E material is substantially unchanged following the adsorption/desorption analysis. In certain embodiments, Form E is stable with respect to humidity.

In certain embodiments, Form E of Compound A may be characterized by its stability profile. In certain embodiments, Form E material is stable, e.g., its XRPD pattern remains substantially unchanged, upon compression. For example, in certain embodiments, Form E is stable following compression at about 2000 psi pressure for about one minute.

In certain embodiments, Form E of Compound A may be characterized by particle analysis. In certain embodiments, Form E is characterized as a white powder. In certain embodiments, a sample of Form E comprises particles having a flake-like morphology. In certain embodiments, a sample of Form E comprises particles with a $D_{90}$ of less than about 18 µm.

Certain embodiments herein provide Form E of Compound A which is substantially pure. Certain embodiments herein provide Form E of Compound A which is substantially free of other solid forms comprising Compound A including, e.g., Forms A, B, C, D, F, G and/or an amorphous solid form comprising Compound A as provided herein. Certain embodiments herein provide Form E as a mixture of solid forms comprising Compound A, including, e.g., a mixture comprising one or more of the following: Forms A, B, C, D, F, G and an amorphous solid form comprising Compound A as provided herein.

4.1.6. Form F of Compound A

Certain embodiments herein provide the Form F crystal form of Compound A. In certain embodiments, Form F of Compound A can be obtained from various solvents, including, but not limited to, solvent systems comprising acetone, ethanol, water, and mixtures comprising two or more thereof. For example, in certain embodiments, Form F can be obtained by crystallization from a solvent system comprising ethanol and/or water, e.g., by a process comprising contacting a solid form comprising Compound A with a solvent system comprising ethanol and/or water, followed by isolation of Form F.

Figure 21:
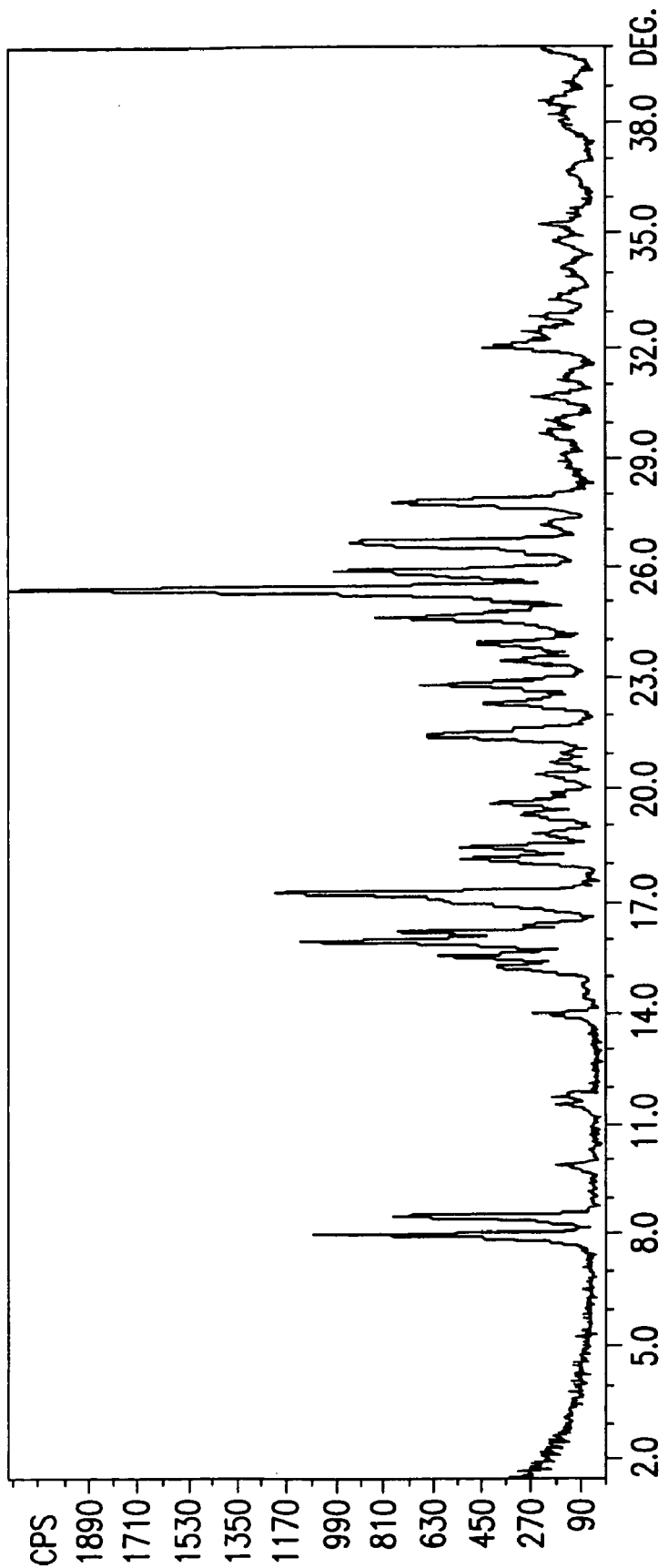

In certain embodiments, Form F of Compound A may be characterized by X-ray powder diffraction analysis. A representative XRPD pattern of Form F of Compound A is provided in FIG. 21. In certain embodiments, Form F of Compound A is characterized by XRPD peaks located at one, two, three, four, five, six, seven, eight, nine, ten, eleven or twelve of the following approximate positions: 8.1, 8.6, 15.6, 17.3, 19.3, 21.4, 22.8, 24.6, 25.4, 25.9, 26.6, 27.7 degrees 2θ. In certain embodiments, Form F of Compound A is characterized by an XRPD pattern which matches the pattern exhibited in FIG. 21. In certain embodiments, Form F of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form F pattern provided herein.

Figure 22:
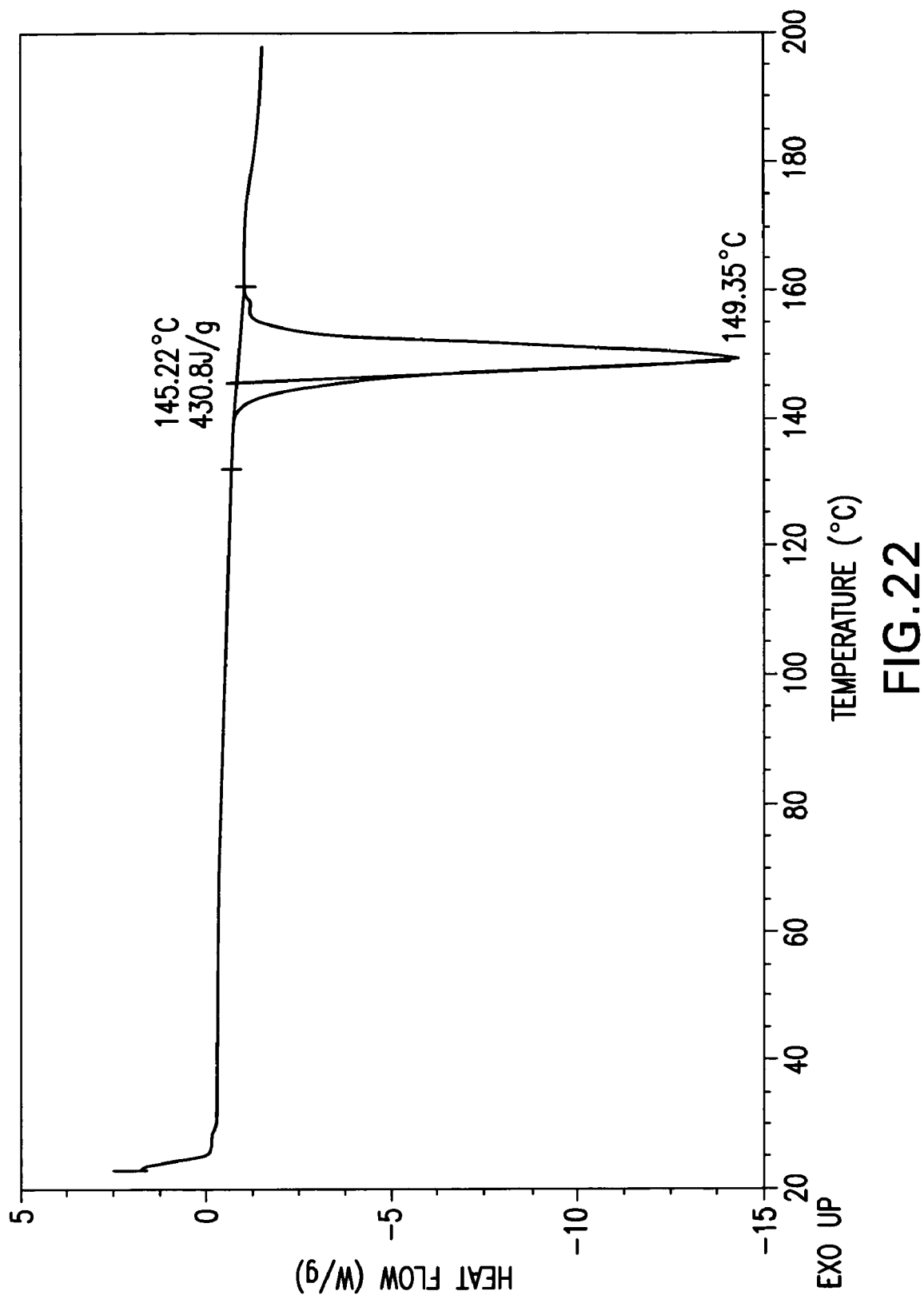
Figure 23:
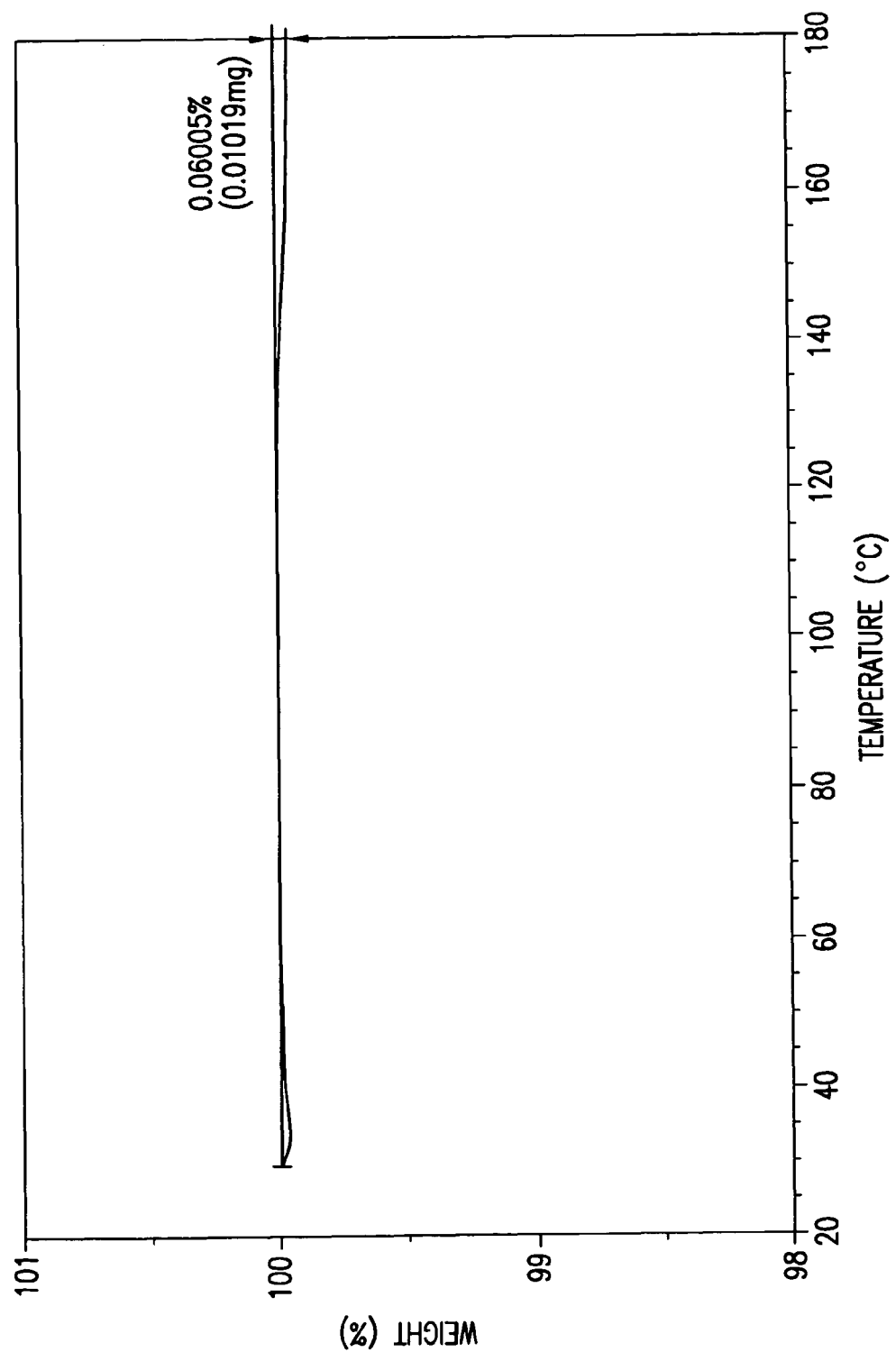

In certain embodiments, Form F of Compound A may be characterized by thermal analysis. A representative DSC plot for Form F of Compound A is shown in FIG. 22. In certain embodiments, Form F is characterized by a DSC plot comprising an endothermic event with an onset temperature of about 145° C. A representative TGA plot for Form F of Compound A is shown in FIG. 23. In certain embodiments, Form F is characterized by a TGA plot comprising a mass loss of less than about 1%, e.g., about 0.1%, of the total mass of the sample upon heating from about 25° C. to about 180° C. In certain embodiments, Form F of Compound A does not contain substantial amounts of either water or other solvent in the crystal lattice. In certain embodiments, Form F is unsolvated. In certain embodiments, Form F is anhydrous.

Figure 24:
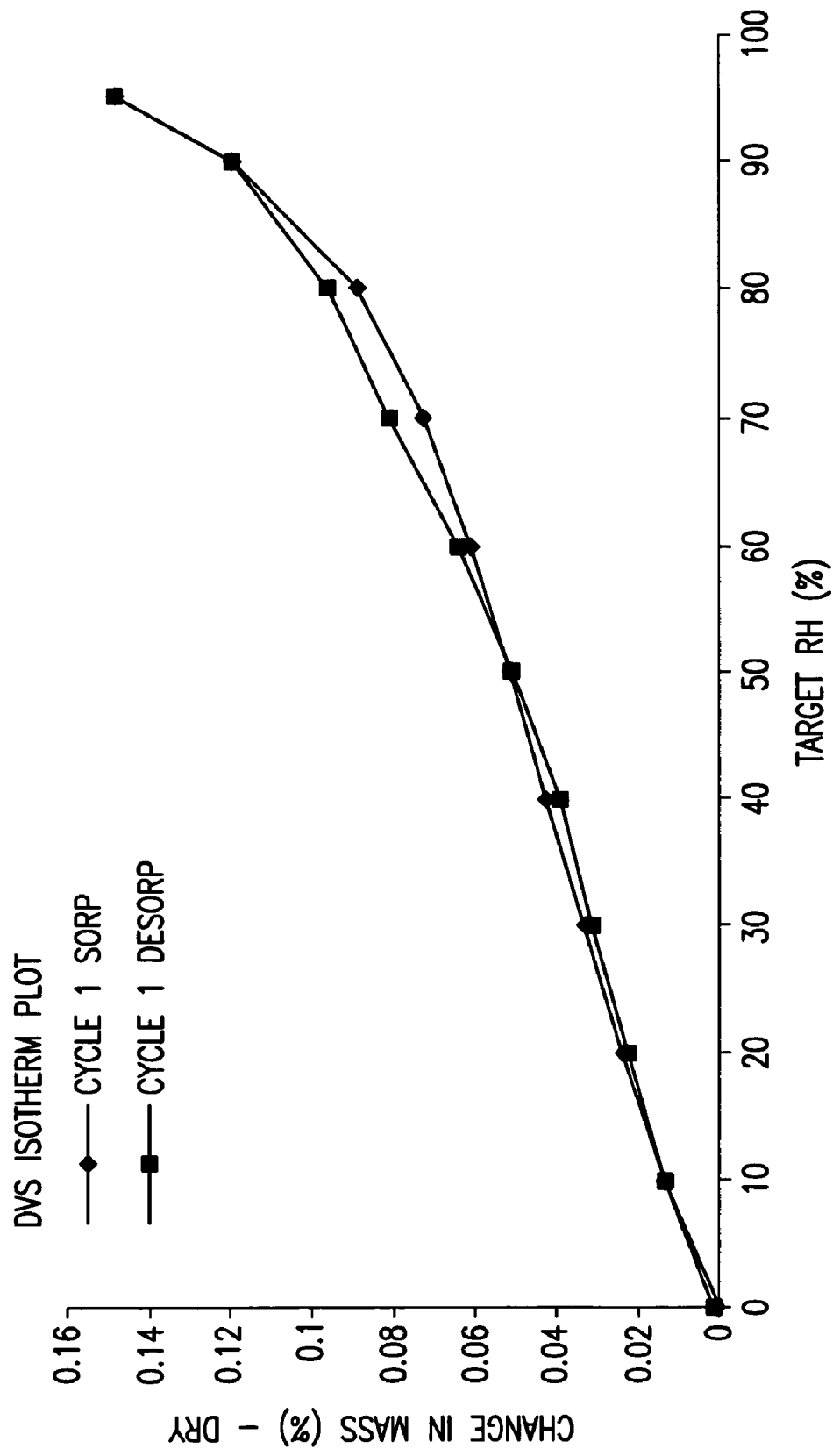

In certain embodiments, Form F of Compound A may be characterized by moisture sorption analysis. A representative moisture sorption isotherm plot is shown in FIG. 24. In certain embodiments, when the RH is increased from about 0% to about 95% RH, Form F exhibits a mass change of less than about 1%, e.g., about 0.2%, of the starting mass of the sample. In certain embodiments, mass gained upon adsorption is lost when the RH is decreased back to about 0% RH. In certain embodiments, Form F is substantially nonhygroscopic. In certain embodiments, the XRPD pattern of Form F material is substantially unchanged following the adsorption/desorption analysis. In certain embodiments, Form F is stable with respect to humidity.

In certain embodiments, Form F of Compound A may be characterized by its stability profile. In certain embodiments, Form F material is stable, e.g., its XRPD pattern remains substantially unchanged, upon compression. For example, in certain embodiments, Form F is stable following compression at about 2000 psi pressure for about one minute. In certain embodiments, Form F is stable following exposure to a solvent system comprising, e.g., ethanol, acetone or mixtures thereof, for about two days at about 25° C.

In certain embodiments, Form F of Compound A may be characterized by particle analysis. In certain embodiments, Form F is characterized as a white powder. In certain embodiments, a sample of Form F comprises particles having a flake-like morphology. In certain embodiments, a sample of Form F comprises particles with a $D_{90}$ of less than about 18 µm.

Certain embodiments herein provide Form F of Compound A which is substantially pure. Certain embodiments herein provide Form F of Compound A which is substantially free of other solid forms comprising Compound A including, e.g., Forms A, B, C, D, E, G and/or an amorphous solid form comprising Compound A as provided herein. Certain embodiments herein provide Form F as a mixture of solid forms comprising Compound A, including, e.g., a mixture comprising one or more of the following: Forms A, B, C, D, E, G and an amorphous solid form comprising Compound A as provided herein.

4.1.7. Form G of Compound A

Certain embodiments herein provide the Form G crystal form of Compound A. In certain embodiments, Form G of Compound A can be obtained from various solvents, including, but not limited to, solvent systems comprising ethyl acetate. For example, in certain embodiments, Form G can be obtained by crystallization from a solvent system comprising ethyl acetate, e.g., by a process comprising contacting a solid form comprising Compound A with a solvent system comprising ethyl acetate, followed by isolation of Form G.

Figure 25:
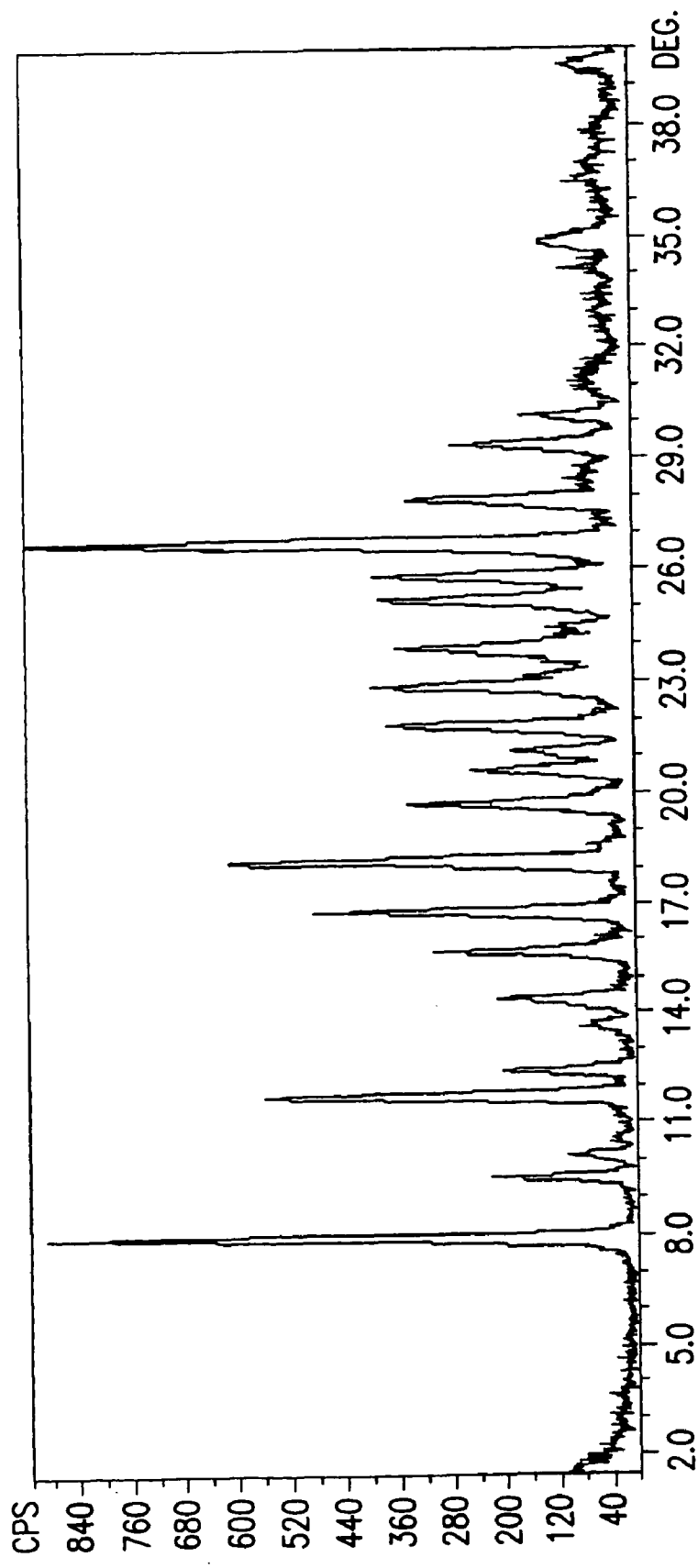

In certain embodiments, Form G of Compound A may be characterized by X-ray powder diffraction analysis. A representative XRPD pattern of Form G of Compound A is provided in FIG. 25. In certain embodiments, Form G of Compound A is characterized by XRPD peaks located at one, two, three, four, five, six, seven, eight, nine, ten, eleven or twelve of the following approximate positions: 7.9, 9.5, 11.7, 15.7, 16.8, 18.1, 19.7, 21.8, 22.8, 25.1, 25.8, 26.7 degrees 2θ. In certain embodiments, Form G of Compound A is characterized by an XRPD pattern which matches the pattern exhibited in FIG. 25. In certain embodiments, Form G of Compound A is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in the representative Form G pattern provided herein.

Figure 26:
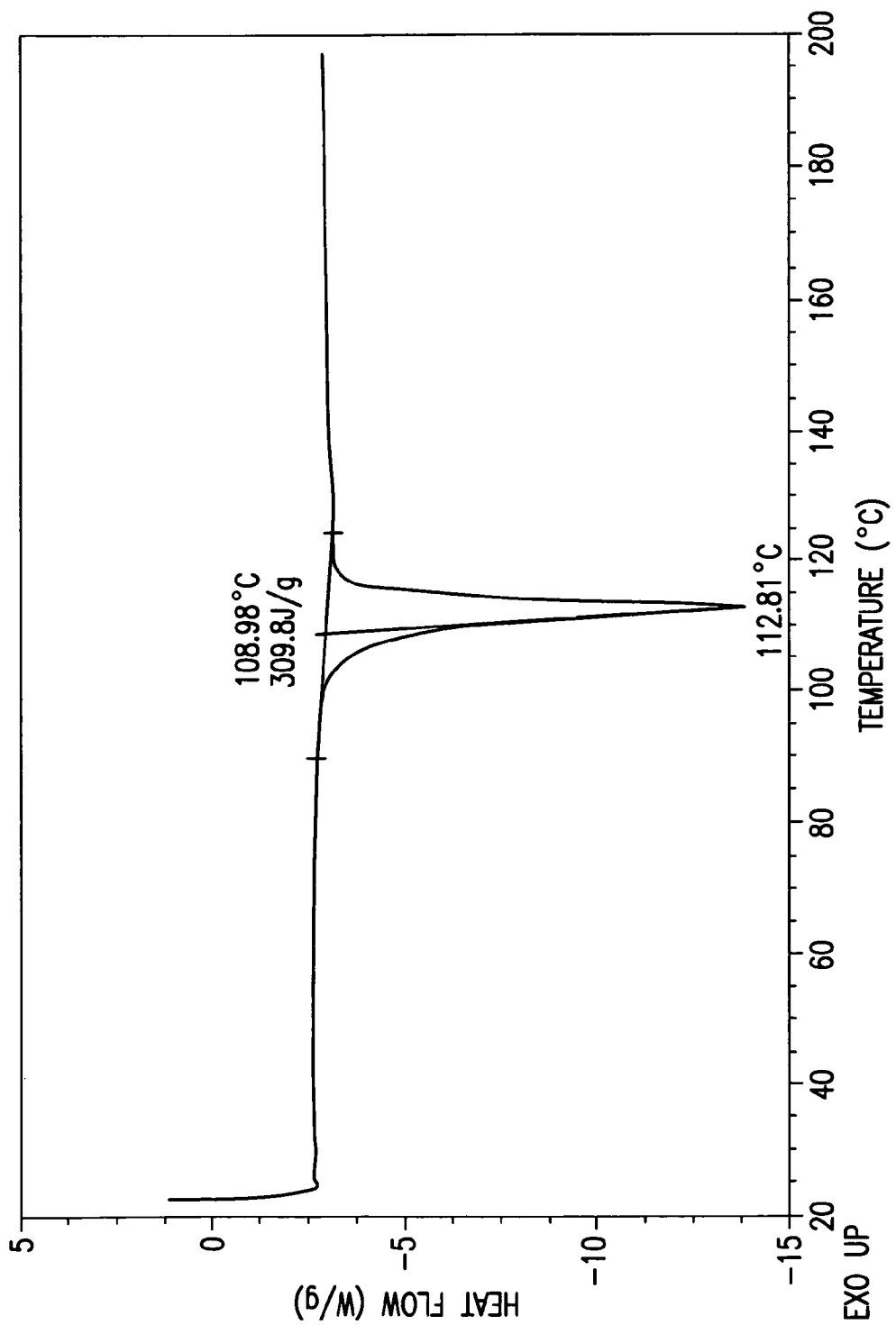
Figure 27:
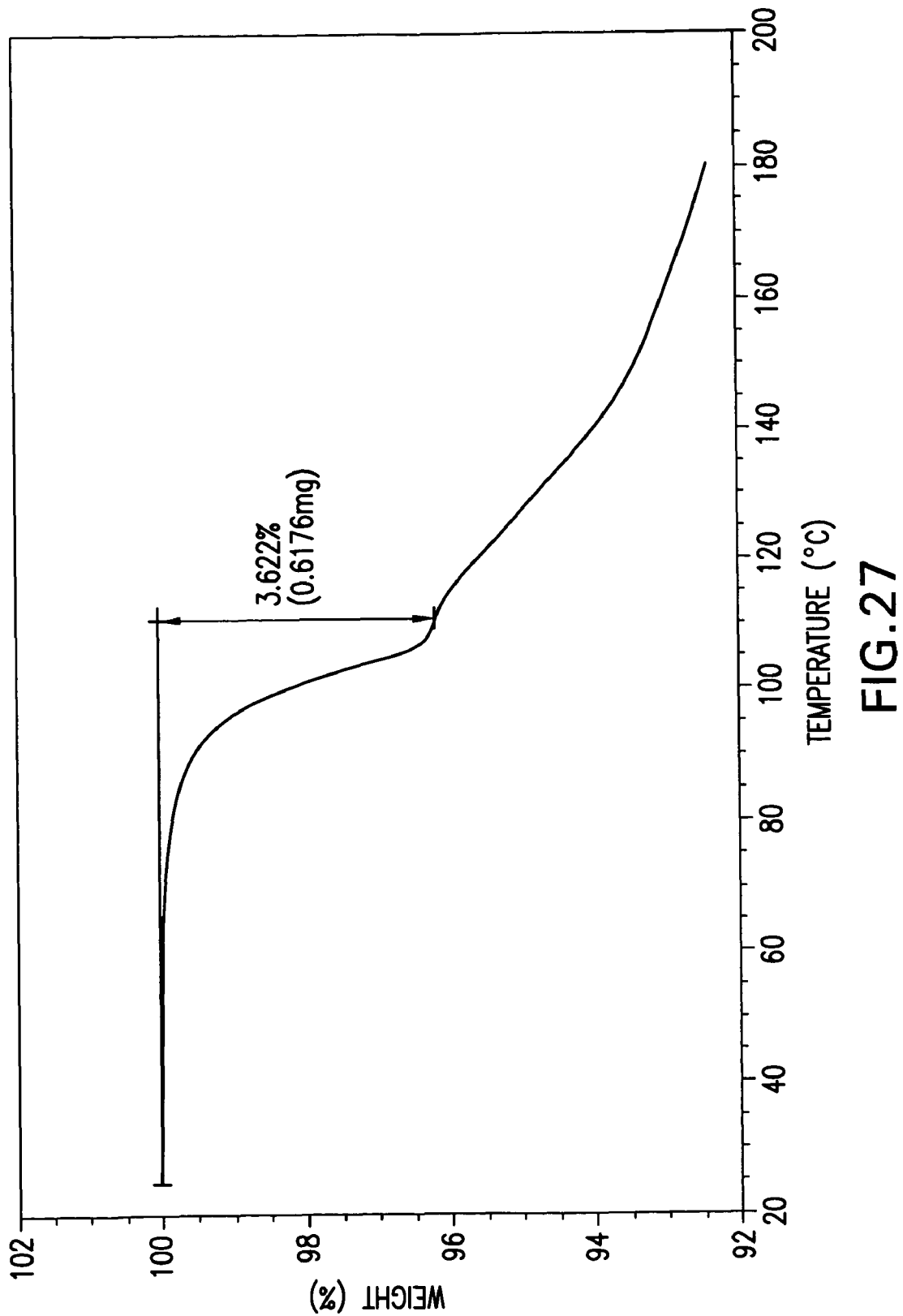

In certain embodiments, Form G of Compound A may be characterized by thermal analysis. A representative DSC plot for Form G of Compound A is shown in FIG. 26. In certain embodiments, Form G is characterized by a DSC plot comprising an endothermic event with an onset temperature of about 109° C. A representative TGA plot for Form G of Compound A is shown in FIG. 27. In certain embodiments, Form G is characterized by a TGA plot comprising a mass loss of less than about 8%, e.g., about 3.8%, of the total mass of the sample upon heating from about 25° C. to about 110° C. In certain embodiments, the TGA mass loss event comprises the loss of the solvent ethyl acetate, as indicated, e.g., by TG-IR analysis. In certain embodiments, Form G of Compound A is solvated. In certain embodiments, Form G is an ethyl acetate solvate. In certain embodiments, the crystal lattice of Form G comprises about three molar equivalents of ethyl acetate per mole of Compound A.

Figure 28:
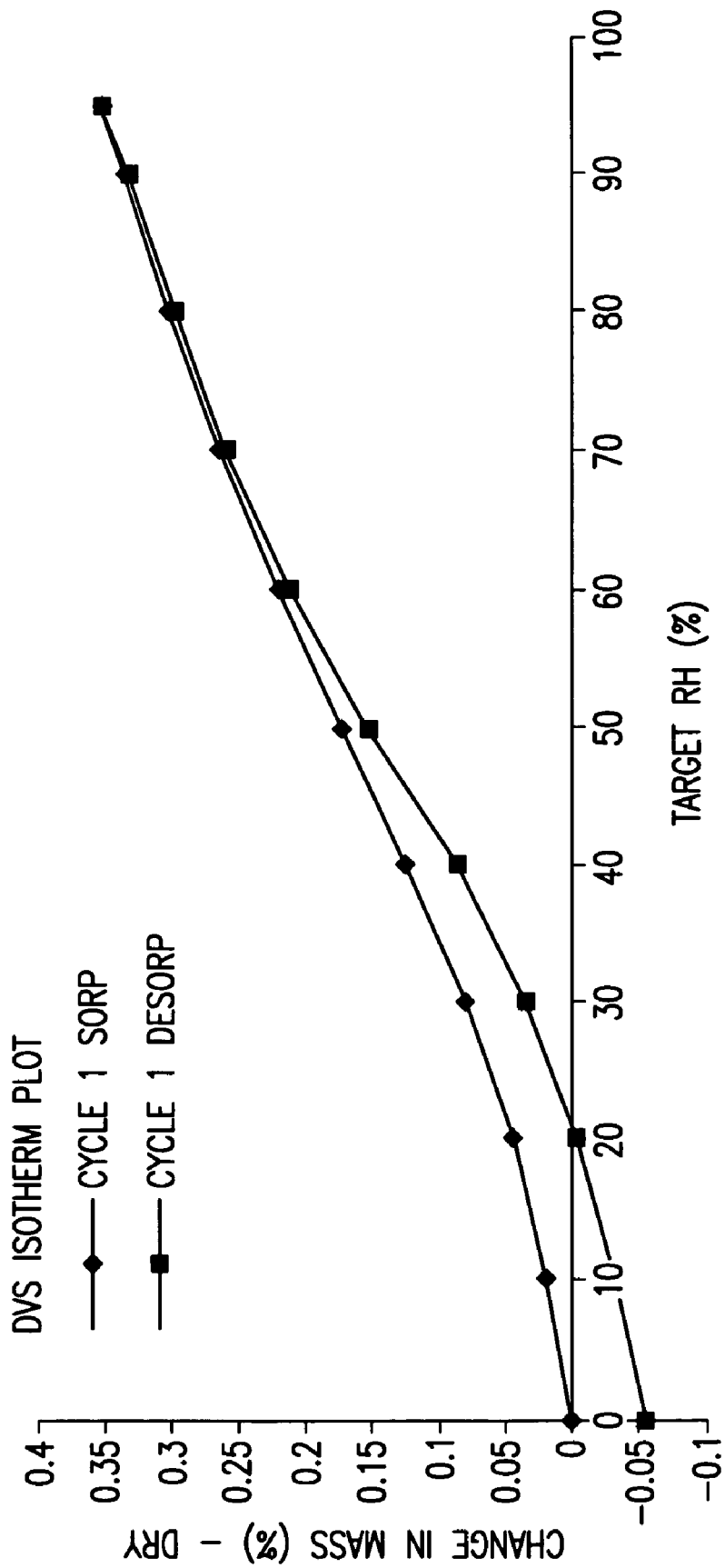

In certain embodiments, Form G of Compound A may be characterized by moisture sorption analysis. A representative moisture sorption isotherm plot is shown in FIG. 28. In certain embodiments, when the RH is increased from about 0% to about 95% RH, Form G exhibits a mass change of less than about 1%, e.g., about 0.4%, of the starting mass of the sample. In certain embodiments, mass gained upon adsorption is lost when the RH is decreased back to about 0% RH. In certain embodiments, Form G is substantially nonhygroscopic. In certain embodiments, the XRPD pattern of Form G material is substantially unchanged following the adsorption/desorption analysis. In certain embodiments, Form G is stable with respect to humidity.

In certain embodiments, Form G of Compound A may be characterized by its stability profile. In certain embodiments, Form G material is stable, e.g., its XRPD pattern remains substantially unchanged, upon compression. For example, in certain embodiments, Form F is stable following compression at about 2000 psi pressure for about one minute. In certain embodiments, Form G converts to Form B upon exposure to a solvent system comprising, e.g., ethanol, acetone or mixtures thereof, for about two days at about 25° C.

In certain embodiments, Form G of Compound A may be characterized by particle analysis. In certain embodiments, Form G is characterized as a white powder. In certain embodiments, a sample of Form G comprises particles having a flake-like morphology. In certain embodiments, a sample of Form G comprises particles with a $D_{90}$ of less than about 18 μm.

Certain embodiments herein provide Form G of Compound A which is substantially pure. Certain embodiments herein provide Form G of Compound A which is substantially free of other solid forms comprising Compound A including, e.g., Forms A, B, C, D, E, F and/or an amorphous solid form comprising Compound A as provided herein. Certain embodiments herein provide Form G as a mixture of solid forms comprising Compound A, including, e.g., a mixture comprising one or more of the following: Forms A, B, C, D, E, F and an amorphous solid form comprising Compound A as provided herein.

4.2. METHODS OF TREATMENT

The invention encompasses methods of treating, preventing and managing diseases or disorders ameliorated by the reduction of levels of TNF-α in a patient which comprise administering to a patient in need of such treatment, prevention or management a therapeutically or prophylactically effective amount of one or more solid forms comprising Compound A, such as, e.g., Form A of Compound A, Form B of Compound A, Form C of Compound A, Form D of Compound A, Form E of Compound A, Form F of Compound A, Form G of Compound A, or an amorphous form of Compound A, as provided herein.

Disorders ameliorated by the inhibition of TNF-α include, but are not limited to: heart disease, such as congestive heart failure, cardiomyopathy, pulmonary edema, endotoxin-mediated septic shock, acute viral myocarditis, cardiac allograft rejection, and myocardial infarction; solid tumors, including but not limited to, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma; and blood-borne tumors including but not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, multiple myeloma and acute and chronic leukemias, for example, lymphoblastic, myelogenous, lymphocytic, and myelocytic leukemias.

Specific methods of the invention further comprise the administration of an additional therapeutic agent (i.e., a therapeutic agent other than Compound A). Examples of additional therapeutic agents include, but are not limited to, anticancer drugs such as, but are not limited to: alkylating agents, nitrogen mustards, ethylenimines, methylmelamines, alkyl sulfonates, nitrosoureas, triazenes, folic acid analogs, pyrimidine analogs, purine analogs, vinca alkaloids, epipodophyllotoxins, antibiotics, topoisomerase inhibitors and anticancer vaccines.

Specific additional therapeutic agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Embodiments herein further encompass a method of treating or preventing diseases or disorders ameliorated by the inhibition of PDE4 in a patient which comprise administering to a patient in need of such treatment or prevention one or more solid forms comprising Compound A. Disorders ameliorated by the inhibition of PDE4 include, but are not limited to, asthma, inflammation, chronic or acute obstructive pulmonary disease, chronic or acute pulmonary inflammatory disease, inflammatory bowel disease, Crohn's Disease, Behcet's Disease, colitis, ulcerative colitis and arthritis or inflammation due to reperfusion. In a preferred embodiment, the disease or disorder to be treated or prevented is chronic obstructive pulmonary disease.

Specific methods of the invention can comprise the administration of an additional therapeutic agent such as, but not limited to, anti-inflammatory drugs, antihistamines and decongestants. Examples of such additional therapeutic agents include, but are not limited to: antihistamines including, but not limited to, ethanolamines, ethylenediamines, piperazines, and phenothiazines; antiinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steroids including, but not limited to, cortical steroids and adrenocortical steroids.

Specific methods of the invention avoid or reduce drug-drug interactions and other adverse effects associated with agents used in the treatment of such disorders, including racemic substituted phenylethylsulfones. Without being limited by any theory, certain solid forms comprising Compound A may further provide an overall improved therapeutic effectiveness, or therapeutic index, over racemic 2-[1-(3-Ethoxy-4-methoxyphenyl)-2-methylsulfonylethyl]-4-acetylaminoisoindoline-1,3-dione, including solid forms thereof.

As stated above, certain solid forms comprising Compound A may be used in the treatment or prevention of a wide range of diseases and conditions. The magnitude of a prophylactic or therapeutic dose of a particular active ingredient of the invention in the acute or chronic management of a disease or condition may vary with the nature and severity of the disease or condition and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1,000 mg per day, given as a single once-a-day dose preferably as divided doses throughout a day. More specifically, the daily dose is administered twice daily in equally divided doses. Specifically, a daily dose range may be from about 5 mg to about 500 mg per day, more specifically, between about 10 mg and about 200 mg per day. Specifically, the daily dose may be administered in 5 mg, 10 mg, 15 mg, 20 mg, 25 mg, 50 mg, or 100 mg dosage forms. In managing the patient, the therapy should be initiated at a lower dose, perhaps about 1 mg to about 25 mg, and increased if necessary up to about 200 mg to about 1,000 mg per day as either a single dose or divided doses, depending on the patient's global response. Alternatively, the daily dose is from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause, or sufficient to reduce, adverse effects associated with racemic 2-[1-(3-ethoxy-4-methoxyphenyl)-2-methylsulfonylethyl]-4-acetylaminoisoindoline-1,3-dione are also encompassed by the above described dosage amounts and dose frequency schedules.

4.3. PHARMACEUTICAL COMPOSITIONS

Pharmaceutical compositions and single unit dosage forms comprising one or more solid forms comprising Compound A are provided herein. Also provided herein are methods for preparing pharmaceutical compositions and single unit dosage forms comprising one or more solid forms comprising Compound A. For example, in certain embodiments, individual dosage forms comprising a solid form provided herein or prepared using solid form provided herein may be suitable for oral, mucosal (including rectal, nasal, or vaginal), parenteral (including subcutaneous, intramuscular, bolus injection, intraarterial, or intravenous), sublingual, transdermal, buccal, or topical administration.

In certain embodiments, pharmaceutical compositions and dosage forms provided herein comprise one or more solid forms comprising Compound A. Certain embodiments herein provide pharmaceutical compositions and dosage forms comprising a solid form comprising Compound A, such as, e.g., Forms A, B, C, D, E, F, G or an amorphous solid form comprising Compound A as provided herein, wherein the solid form comprising Compound A substantially pure. Certain embodiments herein provide pharmaceutical compositions and dosage forms comprising a solid form comprising Compound A, such as, e.g., Forms A, B, C, D, E, F, G or an amorphous solid form comprising Compound A as provided herein, which is substantially free of other solid forms comprising Compound A including, e.g., Forms A, B, C, D, E, F, G and/or an amorphous solid form comprising Compound A as provided herein. Certain embodiments herein provide pharmaceutical compositions and dosage forms comprising a mixture of solid forms comprising Compound A, including, e.g., a mixture comprising one or more of the following: Forms A, B, C, D, E, F and an amorphous solid form comprising Compound A as provided herein. Pharmaceutical compositions and dosage forms provided herein typically also comprise one or more pharmaceutically acceptable excipient, diluent or carrier.

A particular pharmaceutical composition encompassed by this embodiment comprises one or more solid forms comprising Compound A and at least one additional therapeutic agent. Examples of additional therapeutic agents include, but are not limited to: anti-cancer drugs and anti-inflammation therapies including, but not limited to, those provided herein.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein lie within the range of from about 1 mg to about 1,000 mg per day, given as a single once-a-day dose in the morning but preferably as divided doses throughout the day. More specifically, the daily dose is administered twice daily in equally divided doses. Specifically, a daily dose range may be from about 5 mg to about 500 mg per day, more specifically, between about 10 mg and about 200 mg per day. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

4.3.1. Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101™, AVICEL-PH-103™, AVICEL RC-581™, AVICEL-PH-105™ (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581 ™. Suitable anhydrous or low moisture excipients or additives include AVICEL-PH-103™ and Starch 1500 LM™.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

4.3.2. Delayed Release Dosage Forms

Solid forms comprising Compound A as provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.3.3. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.3.4. Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80™ (polysorbate 80) and Span 60™ (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different solid forms comprising the active ingredients can be used to further adjust the properties of the resulting composition.

4.3.5. Kits

This invention encompasses kits which, when used by the medical practitioner, can simplify the administration of appropriate amounts of active ingredients to a patient.

A typical kit of the invention comprises a unit dosage form of compound A, or a pharmaceutically acceptable solid form or prodrug thereof, and a unit dosage form of a second active ingredient. Examples of second active ingredients include, but are not limited to, those listed herein.

Kits of the invention can further comprise devices that are used to administer the active ingredient(s). Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

The present application incorporates by reference the entirety of U.S. Pat. No. 6,962,940 (issued Nov. 8, 2005), including the Examples provided therein.

5.1. Example 1

Synthesis of 2-[1-(3-Ethoxy-4-Methoxyphenyl)-2-Methylsulfonylethyl]-4-Acetylaminoisoindoline-1,3-Dione A stirred solution of 1-(3-ethoxy-4-methoxyphenyl)-2-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ: 1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CH), 3.85 (s, 3H, CH3), 4.11 (q, J=7 Hz, 2H, CH$_2$), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ: 14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for C$_{22}$H$_{24}$NO$_7$S: C, 57.38; H, 5.25; N, 6.08. Found: C, 57.31; H, 5.34; N, 5.83.

5.2. Example 2

Synthesis of (+)$_2$-[1-(3-Ethoxy-4-Methoxyphenyl)-2-Methylsulfonylethyl]-4-Acetylaminoisoindoline-1,3-Dione Preparation of 3-aminopthalic acid 10% Pd/C (2.5 g), 3-nitrophthalic acid (75.0 g, 355 mmol) and ethanol (1.5 L) were charged to a 2.5 L Parr hydrogenator under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (br, s, 2H); $^{13}$C-NMR (DMSO-d6) δ: 112.00, 115.32, 118.20, 131.28, 135.86, 148.82, 169.15, 170.09.

Preparation of 3-acetamidophthalic anhydride

A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to about 25° C. and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

Resolution of 2-(3-ethoxy-4-methoxyphenyl-1-(methylsulphonyl)-eth-2-ylamine

A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$ @ pH 7.0, Ultron Chiral ES-OVS from Agilent Technologies, 150 mm×4.6 mm, 0.5 mL/min., @ 240 nm): 18.4 min (S-isomer, 99.2%), 25.5 min (R-isomer, 0.8%).

Preparation of Compound A

A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-ylamine N-acetyl-L-leucine salt (25 g, 56 mmol, 98% ee), 3-acetamidophthalic anhydride (12.1 g, 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of S-{2-[1-(3-ethoxy-4-methoxyphenyl)-2-methylsulfonylethyl]-4-acetamidoisoindoline-1,3-dione} with 98% ee. Chiral HPLC (15/85 EtOH/20 mM KH$_2$PO$_4$ @ pH 5, Ultron Chiral ES-OVS from Agilent Technology, 150 mm×4.6 mm, 0.4 mL/min, @ 240 nm): 25.4 min (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H); $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Figure 29:
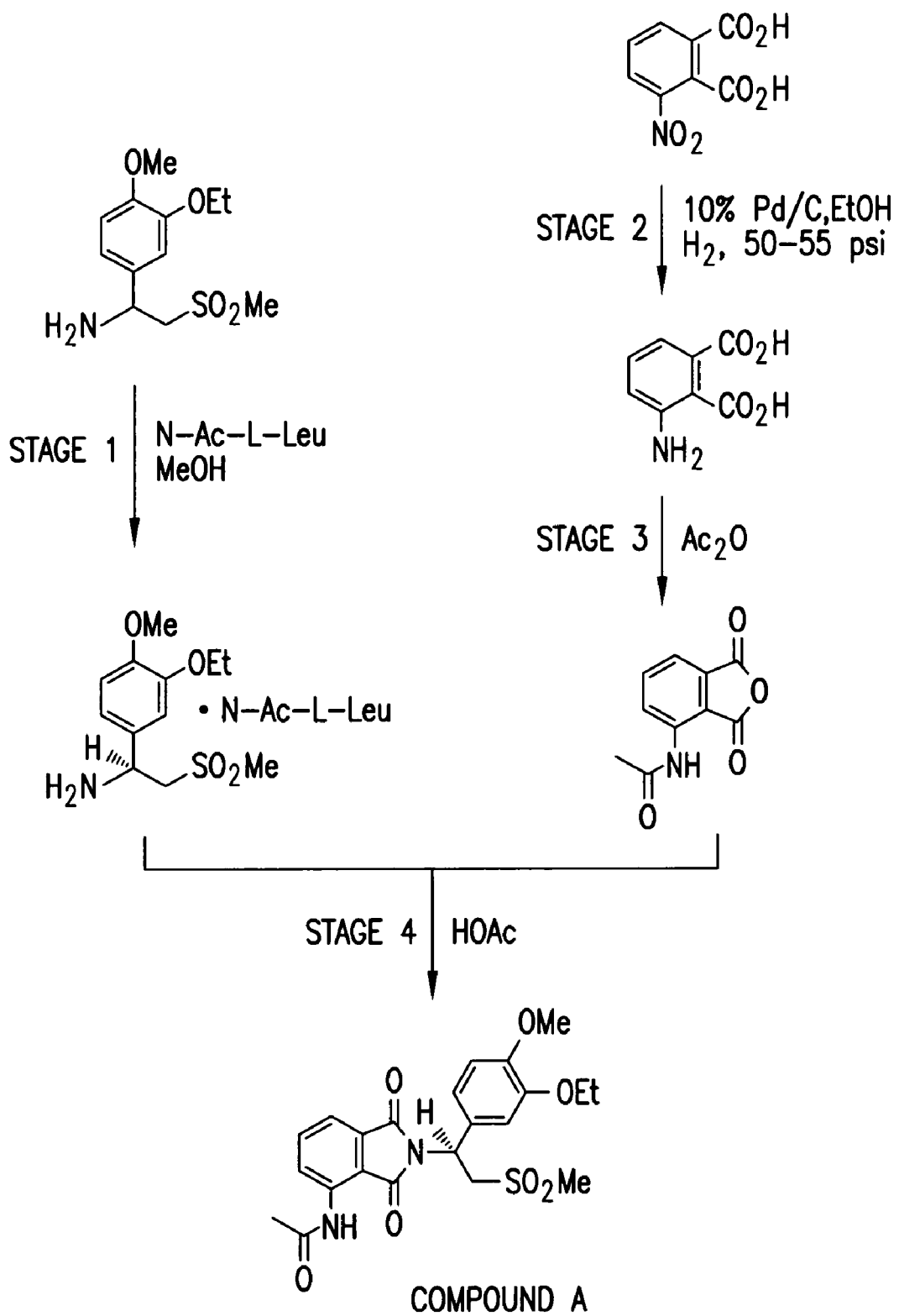
FIG. 29 illustrates a preparation of the (+) enantiomer of 2-[1-(3-Ethoxy-4-methoxyphenyl)-2-methylsulfonylethyl]-4-acetylaminoisoindoline-1,3-dione.

A reaction scheme illustrating a preparation of the (+) enantiomer of Compound A is provided as FIG. 29.

5.3. Example 3

TNF-α Inhibition

Human Whole Blood LPS-induced TNF-α Assay

The ability of compounds to inhibit LPS-induced TNF-α production by human whole blood was measured essentially as described below for the LPS-induced TNF-α assay in human PBMC, except that freshly drawn whole blood was used instead of PBMC. (Muller et al., 1999, *Bioorg. & Med. Chem. Lett.*, 9:1625-1630.) Human whole blood LPS-induced TNF-α $IC_{50}$=294 nM for Compound A.

Mouse LPS-induced Serum TNF-α Inhibition

Compounds were tested in this animal model according to previously described methods (Corral et al., 1996, *Mol. Med.*, 2:506-515). Mouse LPS-induced serum TNF-α inhibition ($ED_{50}$, mg/kg, p.o.)=0.05 for Compound A.

LPS-induced TNF-α Production

Lipopolysaccharide (LPS) is an endotoxin produced by gram-negative bacteria such as *E. coli* which induces production of many pro-inflammatory cytokines, including TNF-α. In peripheral blood mononuclear cells (PBMC), the TNF-α produced in response to LPS is derived from monocytes, which comprise approximately 5-20% of the total PBMC. Compounds were tested for the ability to inhibit LPS-induced TNF-α production from human PBMC as previously described (Muller et al., 1996, *J. Med. Chem.*, 39:3238). PBMC from normal donors were obtained by Ficoll Hypaque (Pharmacia, Piscataway, N.J., USA) density centrifugation. Cells were cultured in RPMI (Life Technologies, Grand Island, N.Y., USA) supplemented with 10% AB±human serum (Gemini Bio-products, Woodland, Calif., USA), 2 mM L-glutamine, 100 U/ml penicillin, and 100 µg/ml streptomycin (Life Technologies).

PBMC ($2\times10^5$ cells) were plated in 96-well flat-bottom Costar tissue culture plates (Corning, N.Y., USA) in triplicate. Cells were stimulated with LPS (Sigma, St. Louis, Mo., USA) at 100 ng/ml in the absence or presence of compounds. Compounds (Celgene Corp., Warren, N.J., USA) were dissolved in DMSO (Sigma) and further dilutions were done in culture medium immediately before use. The final DMSO concentration in all samples was 0.25%. Compounds were added to cells one hour before LPS stimulation. Cells were incubated for 18-20 hours at 37° C. in 5% $CO_2$ and supernatants were then collected, diluted with culture medium and assayed for TNF-α levels by ELISA (Endogen, Boston, Mass., USA). LPS-induced TNF-α $IC_{50}$=77 nM for Compound A.

IL-1β-induced TNF-α Production

During the course of inflammatory diseases, TNF-α production is often stimulated by the cytokine IL-1β, rather than by bacterially derived LPS. Compounds were tested for the ability to inhibit IL-1β-induced TNF-α production from human PBMC as described above for LPS-induced TNF-α production, except that the PBMC were isolated from source leukocyte units (Sera-Tec Biologicals, North Brunswick, N.J., USA) by centrifugation on Ficoll-Paque Plus (Amersham Pharmacia, Piscataway, N.J., USA), plated in 96-well tissue culture plates at $3\times10^5$ cells/well in RPMI-1640 medium (BioWhittaker, Walkersville, Md., USA) containing 10% heat-inactivated fetal bovine serum (Hyclone), 2 mM L-glutamine, 100 U/ml penicillin, and 100 mg/ml streptomycin (complete medium), pretreated with compounds at 10, 2, 0.4, 0.08, 0.016, 0.0032, 0.00064, and 0 µM in duplicate at a final DMSO concentration of 0.1% at 37° C. in a humidified incubator at 5% $CO_2$ for one hour, then stimulated with 50 ng/ml recombinant human IL-1β (Endogen) for 18 hours. IL-β-induced TNF-α $IC_{50}$=83 nM for Compound A.

5.4. Example 4

PDE Selectivity

PDE1, 2, 3, 5, and 6 Enzyme Assays

The specificity of compounds for PDE4 was assessed by testing at a single concentration (10 µM) against bovine PDE1, human PDE2, PDE3, and PDE5 from human platelets (Hidaka and Asano, 1976, *Biochem. Biophys. Acta*, 429:485, and Nicholsen et al., 1991, *Trends Pharmaco. Sci.*, 12:19), and PDE6 from bovine retinal rod outer segments (Baehr et al., 1979, *J. Biol. Chem.*, 254:11669, and Gillespie et al. 1989, *Mol. Pharm.*, 36:773). Results are listed in Table 1.

PDE7 Enzyme Assay

PDE7 is a cAMP-selective PDE expressed mainly in T cells and in skeletal muscle. T cell-derived cytokines such as IL-2 and IFN-γ are potentially regulatable via PDE7 inhibition. PDE7 was purified from Hut78 human T cells by anion exchange chromatography as previously described (Bloom and Beavo, 1996, *Proc. Natl. Acad. Sci. USA*, 93:14188-14192). Compounds were tested against the PDE7 preparation in the presence of 10 nM cAMP as described for PDE4 in Table 1.

5.5. Example 5

PDE4 Inhibition

PDE4 (U937 Cell-derived) Enzyme Assay

PDE4 enzyme was purified from U937 human monocytic cells by gel filtration chromatography as previously described (Muller et al., 1998, *Bioorg. & Med. Chem. Lett.* 8:2669-2674). Phosphodiesterase reactions were carried out in 50 mM Tris HCl pH 7.5, 5 mM $MgCl_2$, 1 µM cAMP, 10 nM [$^3$H]-cAMP for 30 min at 30° C., terminated by boiling, treated with 1 mg/ml snake venom, and separated using AG-1XS ion exchange resin (BioRad) as described (Muller et al., 1998, *Bioorg. & Med. Chem. Lett.* 8:2669-2674). Reactions consumed less than 15% of available substrate. Results are listed in Table 1.

TABLE 1

| PDE Specificity | | | |
|---|---|---|---|
| | Racemic Compound | Compound A | Compound B* |
| PDE Inhibition | | | |
| PDE4 $IC_{50}$ (from U937 cells) (nM) | 81.8 | 73.5 | 611 |
| PDE1 (% inhib at 10 µM) | 9% | 23% | 27% |
| PDE2 (% inhib at 10 µM) | 19% | 6% | 10% |
| PDE3 (% inhib at 10 µM) | 21% | 20% | 31% |
| PDE5 (% inhib at µM) | 3% | 3% | −9% |
| PDE6 (% inhib at 10 µM) | ND | −6% | 10% |
| PDE7 $IC_{50}$ (nM) | 22110 | 20500 | ND |
| PDE Specificity Ratios from above data (*fold) | | | |
| PDE4/PDE1 | >2700 | >500 | >50 |
| PDE4/PDE2 | >800 | >10000 | >260 |
| PDE4/PDE3 | >670 | >1200 | >45 |
| PDE4/PDE5 | >12000 | >30000 | >39000 |
| PDE4/PDE6 | ND | >40000 | >250 |
| PDE7 $IC_{50}$/PDE4 $IC_{50}$ | 270 | 279 | ND |

*Compound B is the (−) enantiomer of Compound A.

5.6. Example 6

Human T Cell Assays

SEB-induced IL-2 and IFN-γ Production

Staphylococcal Enterotoxin B (SEB) is a superantigen derived from gram-positive bacteria *Staphylococcus aureus*. SEB provides a convenient physiological stimulus specific for T cells expressing particular T cell receptor Vβ chains. Human PBMC (consisting of approximately 50% T cells) were isolated from source leukocyte units as described above and plated in 96-well tissue culture plates at $3\times10^5$ cells/well in complete medium, pretreated with compounds at 10, 2, 0.4, 0.08, 0.016, 0.0032, 0.00064, and 0 μM in duplicate at a final DMSO concentration of 0.1% at 37° C. in a humidified incubator at 5% $CO_2$ for 1 hour, then stimulated with 100 ng/ml SEB (Sigma Chemical Co., St. Louis, Mo., USA) for 18 hours. IL-2 and IFN-γ levels were measured by ELISA (R&D Systems, Minneapolis, Minn., USA). IL-2 $IC_{50}$=291 nM for Compound A. IFN-γ $IC_{50}$=46 nM for Compound A.

5.7. Example 7 cAMP Elevation Assays

PGE$_2$-induced cAMP Elevation

Prostaglandin E$_2$ (PGE$_2$) binds to prostanoid receptors on monocytes, T cells and other leukocytes and consequently elevates intracellular cAMP levels, resulting in inhibition of cellular responses. The combination of PGE$_2$ and a PDE4 inhibitor synergistically elevates cAMP levels in these cell types, and the elevation of cAMP in PBMC caused by PDE4 inhibitors in the presence of PGE$_2$ is proportional to the inhibitory activity of that PDE4 inhibitor. Intracellular cAMP was measured in human PBMC as follows. PBMC were isolated as described above and plated in 96-well plates at $1\times10^6$ cells per well in RPMI-1640. The cells were pretreated with compounds at 100, 10, 1, 0.1, 0.01, and 0 μM in a final concentration of 2% DMSO in duplicate at 37° C. in a humidified incubator at 5% $CO_2$ for one hour. The cells were then stimulated with PGE$_2$ (10 μM) (Sigma) for 1 h. The cells were lysed with HCl, 0.1 N final concentration to inhibit phosphodiesterase activity and the plates were frozen at −20° C. The cAMP produced was measured using cAMP (low pH) Immunoassay kit (R&D Systems). PBMC cAMP $EC_{50}$ for racemate is 3.09 μM. PBMC cAMP $EC_{50}$ for Compound A is 1.58 μM.

Elevation of cAMP in human neutrophils was measured as follows. PBMC were removed from source leukocytes (Sera-Tec Biologicals) by centrifugation on Ficoll-Paque Plus (Amersham Pharmacia). The resulting erythrocyte/polymorphonuclear cell (PMN) pellet was resuspended in Hank's Balanced Salt Solution (BioWhittaker) and mixed with an equal volume of 3% Dextran T-500 (Amersham Pharmacia) in 0.9% saline. Erythrocytes were allowed to sediment for 20 minutes, and the PMN were removed and centrifuged at 120 rpm for 8 minutes at 4° C. The remaining erythrocytes were lysed in cold 0.2% saline for 30 seconds, and the cells restored to isotonicity by the addition of an equal volume of 1.6% saline. The PMN were centrifuged at 1200 rpm for 8 minutes at 4° C., then resuspended in RPMI-1640 and assayed for cAMP elevation as described for PBMC above. PMN were found to be approximately 74% CD 18/CD11b$^+$, 71% CD16$^+$ CD9$^+$ neutrophils by flow cytometry on a FACSCalibur (Becton Dickinson, San Jose, Calif., USA). Results are shown in Table 2.

fMLF-induced LTB4 Production

N-formyl-methionine-leucine-phenylalanine (fMLF) is a bacterially derived peptide that activates neutrophils to rapidly degranulate, migrate, adhere to endothelial cells, and release leukotriene LTB4, a product of arachidonic acid metabolism and itself a neutrophil chemoattractant. Compounds were tested for the ability to block fMLF-induced neutrophil LTB4 production as previously described (Hatzelmann and Schudt, 2001, *J. Pharm. Exp. Ther.*, 297:267-279), with the following modifications. Neutrophils were isolated as described above and resuspended in phosphate-buffered saline without calcium or magnesium (BioWhittaker) containing 10 mM HEPES pH 7.2 and plated in 96-well tissue culture plates at a concentration of $1.7\times10^6$ cells/well. Cells were treated with 50 μM thimerosal (Sigma)/1 mM CaCl$_2$/1 mM MgCl$_2$ for 15 minutes at 37° C. 5% $CO_2$, then treated with compounds at 1000, 200, 40, 8, 1.6, 0.32, 0.064, and 0 nM in a final DMSO concentration of 0.01% in duplicate for 10 minutes. Neutrophils were stimulated with 1 μM fMLF for 30 minutes, then lysed by the addition of methanol (20% final concentration) and frozen in a dry ice/isopropanol bath for 10 minutes. Lysates were stored at −70° C. until the LTB4 content was measured by competitive LTB4 ELISA (R&D Systems). Results are shown in Table 2.

Zymosan-induced IL-8 Production

Zymosan A, or the heat-killed yeast *Saccharomyces cerevisiae*, binds to the adhesion molecule Mac-1 on the neutrophil surface and triggers phagocytosis, cell activation and IL-8 production. Zymosan-induced IL-8 production was measured as previously described (Au et al., 1998, *Brit. J. Pharm.*, 123:1260-1266) with the following modifications. Human neutrophils were purified as described above, plated in 96-well tissue culture plates at $3\times10^5$ cells/well in complete medium, treated with compounds at 10, 2, 0.4, 0.08, 0.016, 0.0032, 0.00064, and 0 μM in duplicate in a final DMSO concentration of 0.1% for 1 hour at 37° C. 5% $CO_2$. Neutrophils were then stimulated with unopsonized, boiled Zymosan A (Sigma) at $2.5\times10^5$ particles/well for 18 hours. Supernatants were harvested and tested for IL-8 by ELISA (R&D Systems). Results are shown in Table 2.

fMLF-induced CD18/CD11b Expression

CD18/CD11b (Mac-1) expression on neutrophils was measured as previously described (Derian et al., 1995, *J. Immunol.*, 154:308-3 17) with the following modifications. Neutrophils were isolated as described above, then resuspended in complete medium at $1\times10^6$ cells/ml, pretreated with compounds at 10, 1, 0.1, 0.01, and 0 μM in duplicate at a final DMSO concentration of 0.1% for 10 minutes at 37° C. 5% $CO_2$. Cells were then stimulated with 30 nM fMLF for 30 minutes and then chilled to 4° C. Cells were treated with rabbit IgG (Jackson ImmunoResearch Labs, West Grove, Pa., USA) (10 μg/$1\times10^6$ cells) to block Fc receptors, stained with CD18-FITC and CD11b-PE (Becton Dickinson), and analyzed by flow cytometry on a FACSCalibur. CD18/CD11b expression (mean fluorescence) in the absence of stimulation was subtracted from all samples to obtain inhibition curves and calculate $IC_{50}$ values. Results are shown in Table 2.

fMLF-induced Adhesion to HUVEC

Human umbilical vein endothelial cells (HUVEC) were used as a substrate for neutrophil adhesion as previously described (Derian et al., 1995, *J. Immunol.*, 154:308-317) with the following modifications. HUVEC cells were obtained from Anthrogenesis (Cedar Knolls, N.J., USA), and neutrophils were not treated with cytochalasin B. Cells were treated with compounds at 10, 1, 0.1, 0.01, 0.001, and 0 μM in a final DMSO concentration of 0.1% in duplicate for 10 minutes, stimulated with 500 nM fMLF for 30 minutes, and washed twice with PBS before measuring fluorescence on an FLX800 plate reader (Bio-Tek Instruments, Winooski, Vt., USA). Results are shown in Table 2.

TABLE 2

Assay results

| Human Neutrophil Assays (all values in nM) | Racemic Compound | Compound A |
|---|---|---|
| $PGE_2$-induced cAMP $EC_{50}$ | 12589 | 4570 |
| fMLF-induced LTB4 $IC_{50}$ | 20.1 | 2.48 |
| Zymosan-induced IL-8 $IC_{50}$ | ND | 94 |
| fMLF-induced CD18 expression $IC_{50}$ | ND | 390 |
| fMLF-induced CD11b expression $IC_{50}$ | ND | 74 |
| fMLF-induced adhesion to HUVEC $IC_{50}$ | ND | 150 |

5.8. Example 8

Aqueous Solubility

Equilibrium solubilities were measured in pH 7.4 aqueous buffer. The pH 7.4 buffer was prepared by adjusting the pH of a 0.07 M $NaH_2PO_4$ solution to 7.4 with 10 N NaOH. The ionic strength of the solution was 0.15. At least 1 mg of powder was combined with 1 ml of buffer to make >1 mg/ml mixture. These samples were shaken for >2 hours and left to stand overnight at room temperature. The samples were then filtered through a 0.45-μm Nylon syringe filter that was first saturated with the sample. The filtrate was sampled twice, consecutively. The filtrate was assayed by HPLC against standards prepared in 50% methanol. Compound A has 3.5-fold greater aqueous solubility than the racemic mixture. Measured solubility Compound A=0.012 mg/mL; racemic mixture=0.0034 mg/mL.

5.9. Example 9

LPS-Induced Lung Neutrophilia Ferret Model

The conscious ferret model has been used to investigate anti-inflammatory, emetic and behavioral effects of PDE4 inhibitors when administered by the oral (p.o.) route. From these experiments, a therapeutic index (TI) for each PDE4 inhibitor may be determined. The TI has been calculated by dividing the threshold dose for causing emetic episodes and behavioral changes by the anti-inflammatory dose (dose that causes 50% inhibition of the LPS-induced neutrophilia).

Animal Husbandry

Male ferrets (*Mustela Putorius* Euro, weighing 1-2 kg). Ferrets were supplied either by Bury Green Farm or Misay Consultancy. Following transport, the animals were allowed to acclimatize in the holding rooms for a period of not less than seven days. The diet comprised SDS diet C pelleted food given ad lib with Whiskers™ cat food given three times per week. Water was pasteurized animal grade drinking water and was changed daily.

Dosing with PDE4 Inhibitor

PDE4 inhibitors were administered orally (p.o.), at doses initially of 1-10 g/kg, but subsequently up to 30 mg/kg in order to establish whether the TI was 10 or higher, and/or at lower doses to establish the minimum dose to cause 50% inhibition of neutrophilia. Ferrets were fasted overnight but allowed free access to water. The animals were orally dosed with vehicle or PDE4 inhibitor using a 15 cm dosing needle that was passed down the back of the throat into the oesophagus. After dosing, the animals were returned to holding cages fitted with Perspex doors to allow observation, and given free access to water. After dosing, the animals were constantly observed and any emesis or behavioral changes were recorded. The animals were allowed access to food 60 to 90 minutes after p.o. dosing.

Exposure to LPS

Thirty minutes after p.o. dosing with compound or vehicle control, the ferrets were placed into sealed Perspex containers and exposed to an aerosol of LPS (100 μg/ml) for 10 minutes. Aerosols of LPS were generated by a nebulizer (DeVilbiss, USA) and this was directed into the Perspex exposure chamber. Following a 10 minute exposure period, the animals were returned to the holding cages and allowed free access to water, and at a later stage, food. Observation continued for a period of at least 2.5 hours post p.o. dosing and emetic episodes and behavioral changes were recorded.

Bronchoalveolar Lavage

Six hours after LPS exposure the animals were killed by overdose of sodium pentobarbitone administered intraperitoneally. The trachea was then cannulated with polypropylene tubing and the lungs lavaged twice with 20 ml heparinized (10 units/ml) phosphate buffered saline (PBS).

Blood Sampling/Tissue Removal

A terminal blood sample (10 ml) was removed by transthoracic cardiac puncture. The blood was spun at 2,500 rpm for 15 minutes and the plasma was removed and stored at −20° C. The brain also removed and frozen at −20° C. for analysis of compound content.

Cell Counts

The bronchoalveolar lavage (BAL) samples were centrifuged at 1,500 rpm for 5 minutes. The supernatant was removed and the resulting cell pellet re-suspended in 1 ml PBS. A cell smear of the re-suspended fluid was prepared and stained with Leishmans stain to allow differential cell counting. A total cell count was made using the remaining re-suspended sample. From this, the total number of neutrophils in the BAL was determined.

Parameters Measured

1. % Inhibition of LPS-induced pulmonary neutrophilia.
2. Emetic episodes—the number of vomits and retches were counted.
3. Behavioral changes—the following behavioral effects were noted: salivation, panting, mouth clawing, flattened posture, ataxia, arched back and backward walking. Any behavioral changes were semi-quantified by applying a severity rating (mild, moderate or severe).
4. The TI was calculated as the highest dose found to not cause emetic episodes divided by the lowest dose found to inhibit pulmonary neutrophilia by 50% or more.

Figure 30:
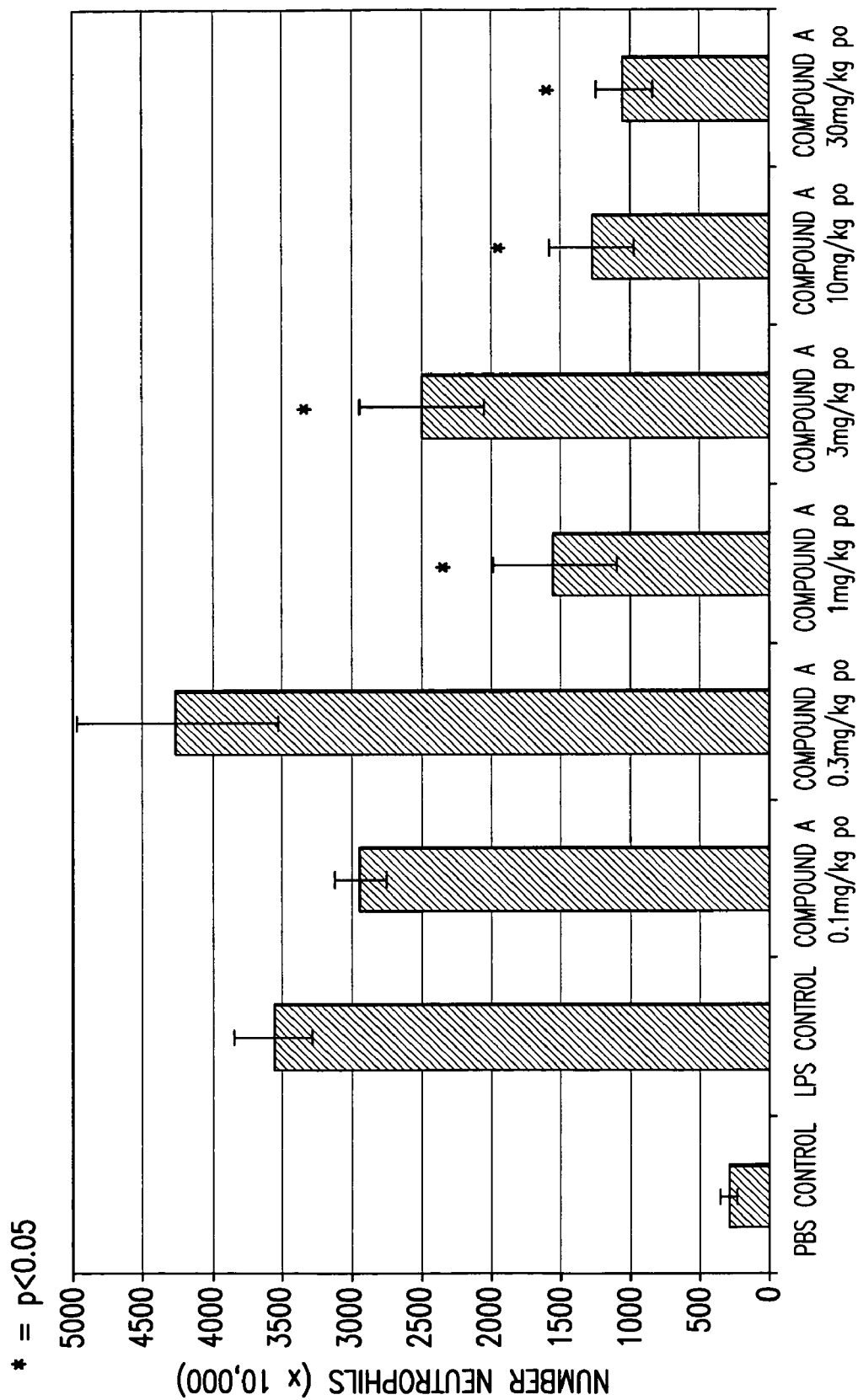
FIG. 30 illustrates the effect of Compound A on LPS-induced neutrophilia in the lungs of conscious ferrets.

The effect of Compound A on LPS-induced neutrophilia in the lungs of conscious ferrets is demonstrated in FIG. 30.

Emesis and Behavioral Changes

Following p.o. dosing of the PDE4, the ferrets were observed for at least two hours and emetic episodes (vomits and retches) and behavioral changes were recorded.

No emetic episodes (retching or vomiting) were observed in the ferrets pre-treated p.o. with the relevant vehicle (acetone/cremophor/distilled water). In a small proportion of the control-treated animals (7/22), mild behavioral changes (lip licking and backward walking) were seen.

Compound A (0.1-3 mg/kg, p.o.), caused no emetic episodes (retching and vomiting). Some behavioral changes (flattened posture, lip licking and backward walking) were observed and classified as mild. At 10 mg/kg in 2/6 ferrets, some retching but no frank emesis was observed along with salivation and behavioral changes (scored as mild or moderate). At the highest dose tested (30 mg/kg) moderate to marked emesis was observed in 3/4 animals along with pronounced behavioral changes. These data are summarized in Table 3.

TABLE 3

Conscious ferret: Emetic episodes and behavioral changes following oral administration of Compound A

| Treatment/dose (mg/kg) | Vomits | Retches | Salivation | Panting | Mouth clawing | Flattened posture | Ataxia | Lip licking | Backward walking |
|---|---|---|---|---|---|---|---|---|---|
| Vehicle (acetone/ cremophor/ dist. H₂O) | None | None | None | None | None | None | None | Mild (6/22) | Mild (7/22) |
| Compound A (0.1 mg/kg) | None | None | None | None | None | Mild (2/5) | None | Mild (4/5) | Mild (3/5) |
| Compound A (0.3 mg/kg) | None | None | None | None | None | Mild (2/6) | None | Mild (3/6) | Mild (4/6) |
| Compound A (1.0 mg/kg) | None | None | None | None | None | Mild (2/6) | None | Mild (6/6) | Mild (4/6) |
| Compound A (3.0 mg/kg) | None | None | None | None | Mild (1/8) | Marked (7/8) | None | Mild (2/8) | Moderate (5/8) |
| Compound A (10 mg/kg) | None | Mild (2/6) | Mild (1/6) | None | Mild (1/6) | Marked (6/6) | None | Moderate (5/6) | Marked (6/6) |
| Compound A (30 mg/kg) | Moderate (3/4) | Marked (3/4) | Moderate (3/4) | Mild (1/4) | Marked (4/4) | Marked (4/4) | Mild (3/4) | Moderate (4/4) | Mild (2/4) |

Animals were observed for up to three hours following dosing. Numbers in parentheses refer to the number of animals that responded. The numbers of animals in each group range from 4 to 22.

Therapeutic Index Calculation

From these experiments, a therapeutic index (TI) was determined for each compound by dividing the threshold dose for inducing emetic episodes by the $ED_{50}$ value for inhibiting the pulmonary neutrophilia. The TI calculation is summarized in Table 4. Compound A had a TI of 12, causing no emetic episodes at an anti-inflammatory dose of 1 mg/kg.

TABLE 4

Summary of the effective doses ($ED_{50}$) for inhibition of LPS-induced pulmonary neutrophilia and induction of emesis and the therapeutic index derived from these values

| Compound | Inhibition of LPS-induced neutrophilia ($ED_{50}$ mg/kg) | Threshold emetic dose (mg/kg) | Therapeutic index |
|---|---|---|---|
| Compound A | 0.8 | 10 | 12 |

5.10. Example 10

Biological Activity of Compound A in Patients with Severe Plaque-Type Psoriasis

Compound A is a novel oral agent that downregulates pro-inflammatory cytokine production in human cellular models. Compound A has been shown to decrease TNF-α, IL-12 and IFN-γ production as well as elevate production of IL-10. Psoriasis is strongly associated with dysregulation of cytokines and chemokines allowing for potential therapies with immunomodulatory compounds. This Phase 2, open-label, single arm, pilot study was designed to assess the biological activity of Compound A in patients with severe plaque-type psoriasis. Additional assessments for clinical outcomes were performed to evaluate the potential efficacy of Compound A in treating severe plaque-type psoriasis.

Compound A was administered 20 mg orally daily for 29 days with an additional 28-day observational follow-up period for patient safety. Skin punch biopsy specimens (6 mm) from target plaques were obtained at baseline, Day 15 and Day 29. A nonlesional skin biopsy was also taken at baseline. The primary pharmacodynamic endpoint was the percent change from baseline in epidermal thickness at Day 29. Epidermal skin thickness measurements and immunohistochemical analysis were carried out by a blinded reviewer to evaluate CD11c, CD83, K16, ICAM-1, HLA-DR, and fillagrin. Biopsy specimens were analyzed by RT-PCR for: TNF-α, p40-IL12/IL23, IL-10, IFN-γ, IP10, IL-2, IL-8, iNOS, p19-IL23, K16, CD 83, and hARP. PASI, PGA, and BSA measurements were performed to explore clinical efficacy during the 29-day treatment phase of the study. Adverse event reporting, clinical laboratory evaluations, physical examinations, ECG and vital sign measurements assessed safety. A total of 19 patients were enrolled: 15 patients had complete sets of evaluable biopsies and 17 patients had complete efficacy assessments.

Figure 31:
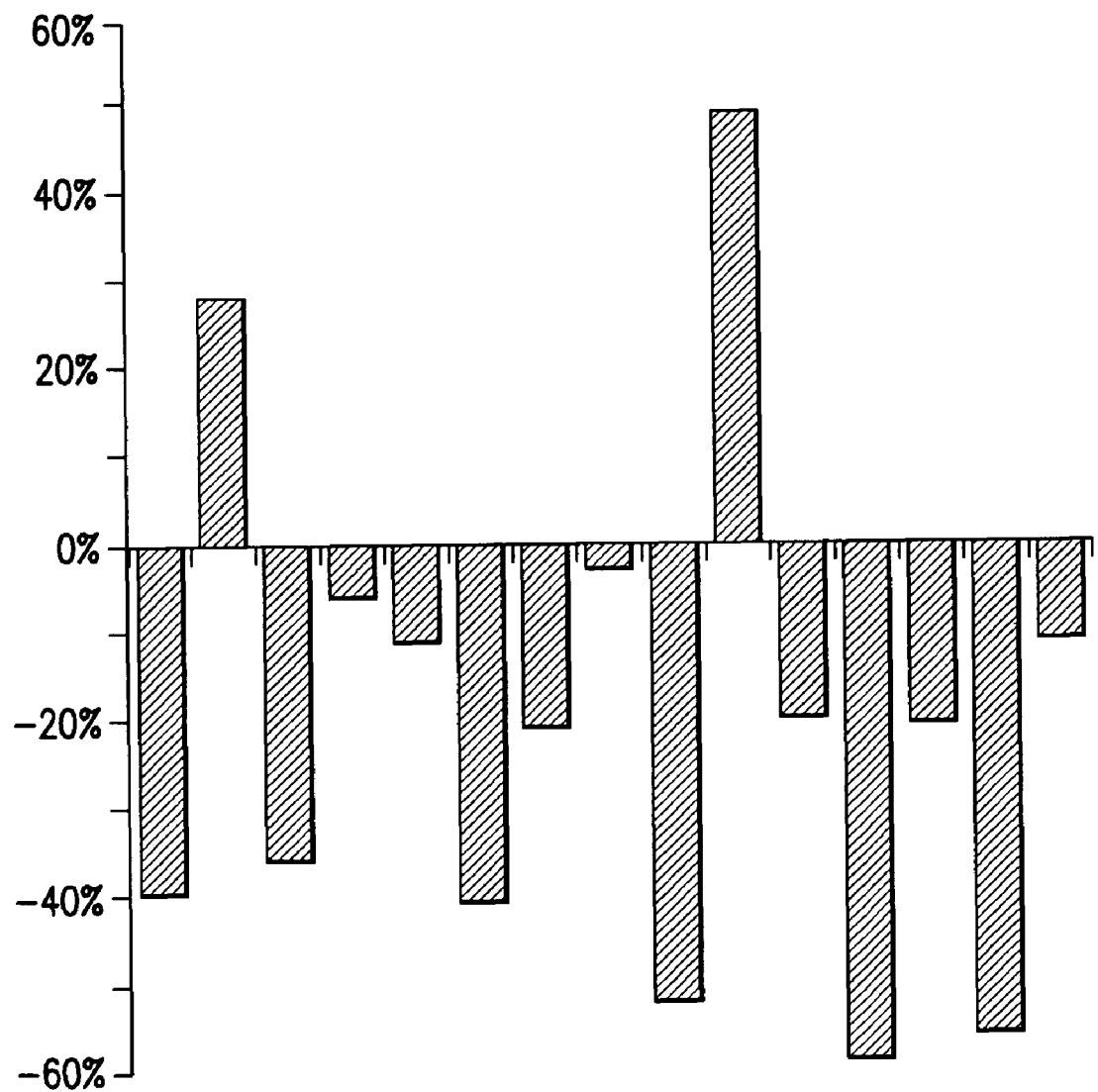
FIG. 31 illustrates the percent change in epidermal thickness among all 15 subjects at Day 29 in a clinical study evaluating Compound A in patients with severe plaque-type psoriasis.

Assessment of the change in epidermal thickness was the primary endpoint in this study. Nineteen patients were enrolled in the study, of which 15 had complete sets of evaluable biopsies at baseline and Day 29. Seventeen of the 19 subjects had clinical efficacy parameters measured at Baseline and Day 29. Eight (53.3%) of the patients with evaluable biopsies at baseline and Day 29 demonstrated a 20% reduction in epidermal skin thickness. The mean reduction of epidermal thickness among all 15 subjects with evaluable biopsies at baseline and Day 29 was 20.5% (p=0.015). FIG. 31 displays the change in epidermal thickness from baseline to Day 29 among subjects with evaluable biopsies.

Key inflammatory markers including epidermal and dermal T-cells, CD83+ and CD11c cells were evaluated in biopsy specimens. Results for 8 patients who responded showed a decrease of epidermal and dermal T-cells by 42.56% and 28.79% respectively in responders (≧20% epidermal thickness reduction). Mean reductions from baseline in epidermal and dermal CD83+ cells were 32.50% and 25.86% respectively in responders. CD11c cells were reduced by 40.16% in the epidermis and 18.50% in the dermis in responders. Table 5 lists reductions in key skin biopsy inflammatory markers in responders and nonresponders. In addition, one patient with abnormal K16 at baseline had normal K16 at Day 29. Three patients with abnormal ICAM-1 at baseline had normal ICAM-1 at Day 29. Two patients with abnormal HLA-DR had normal HLA-DR at Day 29 and three patients with abnormal fillagrin at baseline had normal fillagrin at Day 29.

TABLE 5

Percentage Reduction of Key Inflammatory Markers at Day 29

| Cell | | Epidermis | Dermis |
| --- | --- | --- | --- |
| T-cells | Responder | −42.56% | −28.79% |
| | Nonresponder | +8.74% | −17.34% |
| CD83+ | Responder | −32.50% | −25.86% |
| | Nonresponder | −16.31% | +0.46% |
| CD11c | Responder | −40.16% | −18.50% |
| | Nonresponder | −2.54% | −21.19% |

Figure 32:
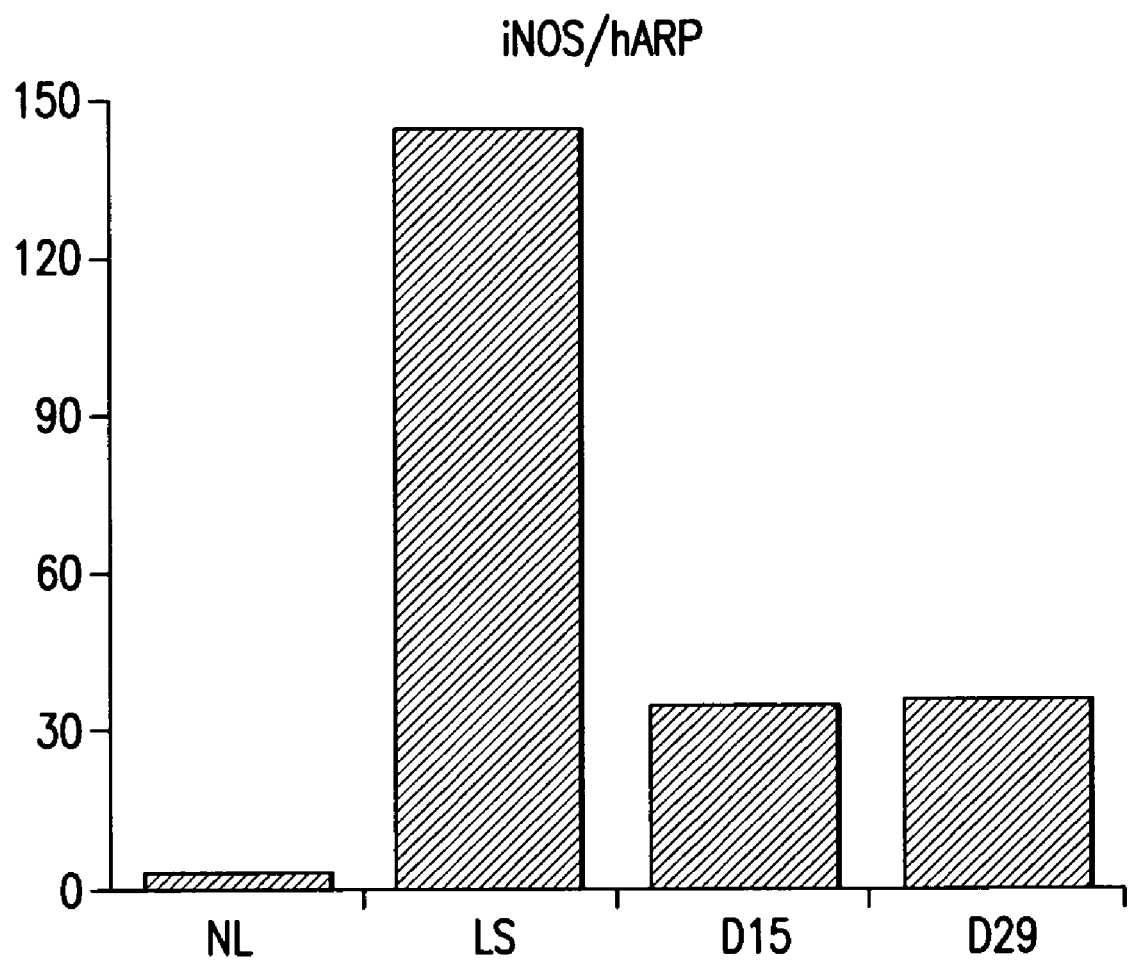
FIG. 32 illustrates the change in mean iNOS (normalized to hARP) in biopsy specimens of lesional skin at Day 29 in a clinical study evaluating Compound A in patients with severe plaque-type psoriasis.

Biopsy specimens were evaluated for mRNA gene expression of key inflammatory markers by RT-PCR including: TNFα, p40-IL12/IL23, IL-10, IFNγ, IP10, IL-2, IL-8, iNOS, p19-IL23, K16 and CD83. The mRNA expression of iNOS was reduced 66.5% (p=0.025) in lesional skin after 29 days of treatment with Compound A. Reductions and increases in mRNA expression of other inflammatory markers showed overall trends of improvement. FIG. 32 graphically displays the change in iNOS expression during the study.

Figure 33:
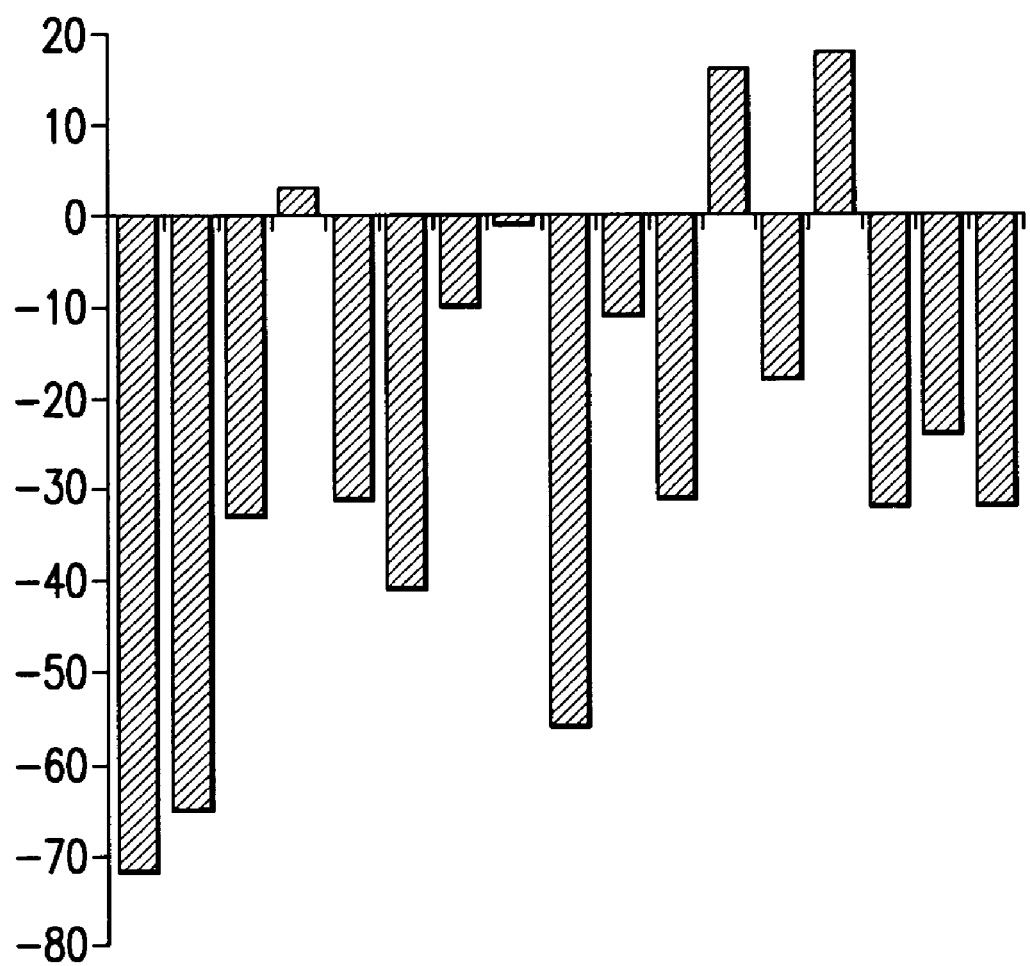
FIG. 33 illustrates the percentage change in total Psoriasis Area and Severity Index (PASI) score among evaluable patients from baseline at Day 29 in a clinical study evaluating Compound A in patients with severe plaque-type psoriasis.

A total of 17 of the 19 subjects enrolled completed the 29-day treatment phase and had complete clinical efficacy assessments. Fourteen (73.7%) of the 19 subjects enrolled demonstrated improvement in their PASI with 3 (15.8%) of these patients showing a >50% reduction from baseline in their total Psoriasis Area and Severity Index (PASI) score at Day 29. FIG. 33 displays the percentage change in PASI scores among evaluable patients from baseline at Day 29. Additionally, 9 (52.9%) of the 17 evaluable patients demonstrated improvement in the static Physician's Global Assessment (sPGA) and 10 (58.8%) of the 17 evaluable patients showed a reduction from baseline in their psoriasis body surface area (BSA) after 29 days of treatment with Compound A. Safety was evaluated during treatment and follow-up phases through monitoring of adverse events, ECGs, laboratory tests, physical exams and vital signs. No deaths were reported nor did any patient prematurely discontinue due to an adverse event. Most common treatment-related adverse events included headache (26.3%), and nausea (15.8%).

In this clinical study, Compound A 20 mg p.o. QD for 29 days was safe in subjects with severe plaque type psoriasis. The primary endpoint was reached with 8 (53.3%) of 15 subjects achieving a 20% reduction in epidermal thickness at Day 29. Reductions of key inflammatory markers in skin biopsies were noted including dermal and epidermal T-cells, CD83+ and CD11c cells. RT-PCR analysis revealed a statistically significant reduction of 66.5% in iNOS mRNA in skin biopsies at Day 29. A positive clinical efficacy signal was noted after 29 days of treatment with Compound A. 73.7% of enrolled patients demonstrated improvement in their psoriasis symptoms with 15.8% of these patients showing >50% reduction from baseline in their PASI score at Day 29. 47.4% of enrolled patients showed an improvement in their sPGA and 52.6% of enrolled patients showed a reduction from baseline in their psoriasis body surface area (BSA) at Day 29.

5.11. Example 11

A Phase 2 Study Demonstrating the Efficacy and Safety of Compound A in Subjects with Moderate-to-Severe Psoriasis This phase 2, multicenter, randomized, double-blind, placebo-controlled, parallel-group, dose-comparison study evaluated the efficacy and safety of Compound A in subjects with moderate to severe plaque-type psoriasis who were candidates for systemic therapy.

This study included a 12-week treatment phase followed by a 4-week observational follow-up phase. A total of 260 subjects were randomized to receive Compound A 20 mg BID, Compound A 20 mg QD, or placebo for 12 weeks. The primary endpoint for this study was the proportion of subjects treated with Compound A who achieved a 75% reduction in Psoriasis Area and Severity Index score ("PASI-75") at week 12/last treatment in reference to the baseline visit. Last treatment is defined as the last PASI assessment completed during the 12-week treatment phase.

At week 12/last treatment, a significantly higher proportion of subjects treated with 20 mg BID (24%) achieved a PASI-75 compared with the placebo group (10%; P=0.023). Of the subjects receiving 20 mg BID or placebo, 57% versus 23% achieved PASI-50 at week 12/last treatment, respectively; whereas 14% versus 6% achieved PASI-90, respectively. At week 12/last treatment, subjects achieved a mean decrease of 52% versus 17% in PASI from baseline in the 20 mg BID versus placebo groups, respectively. Subjects receiving Compound A continued to improve over time, showing the greatest mean percent reduction in PASI score at week 12. Overall, the adverse event profiles were similar across all three treatment groups. The majority of adverse events reported were mild. No study drug-related serious adverse events were reported in this study. No subjects in the 20 mg BID group experienced psoriasis flare during the observational follow-up period.

In this clinical study, Compound A was shown to be well tolerated and safe in subjects with moderate to severe plaque-type psoriasis. The proportions of subjects that achieved 50%, 75%, and 90% improvement in PASI demonstrate the clinical activity of Compound A after 12 weeks of treatment.

5.12. Example 12

Solid Form Screening Studies 5.12.1. Experimental Methodology

Solubility Studies. A weighed sample of Compound A (about 100 mg) was treated with about 2 mL of the test solvent. The solvents used were either reagent or HPLC grade. The resulting mixture was agitated for at least 24 hours at about 25° C. When all of the solids were dissolved by visual inspection, the estimated solubilities were calculated. The solubilities were estimated from these experiments based on the total volume of solvent used to give a solution. The actual solubilities may be greater than those calculated due to the use of large amount of solvent or to a slow rate of dissolution. If dissolution did not occur during the experiment, the solubility was measured gravimetrically. A known volume of filtrate was evaporated to dryness and the weight of the residue was measured.

Solution Evaporation Studies. Solution evaporation was performed for solvents in which the solubility of Compound A was more than about 50 mg/mL, such as acetone, acetonitrile, methylene chloride and tetrahydrofuran. Solid samples were obtained by slowly evaporating the solvents at about 25° C. or about 50° C. in an open vial under nitrogen.

Equilibration Studies. Equilibration experiments were carried out by adding an excess of Compound A to about 2 mL of a test solvent. The resulting mixture was agitated for at least 24 hours at about 25° C. or about 50° C. Upon reaching equilibrium, the saturated solution was removed and allowed to evaporate slowly in an open vial under nitrogen at about 25° C. or about 50° C., respectively. The slurry resulting from the equilibration was filtered and dried in the air.

Cooling Crystallization Studies. Cooling crystallization studies were performed. The solid was dissolved in a solvent at an elevated temperature, about 65° C., and allowed to cool to about 25° C. Samples that did not crystallize at about 25° C. were placed in a refrigerator (about 0-5° C.). Solids were isolated by decantation and allowed to dry in the air.

Solvent/Anti-Solvent Precipitation Studies. Precipitations were carried out by solvent/anti-solvent combinations. The solid was dissolved in a solvent in which Compound A had a relatively high solubility, and then a selected solvent in which Compound A had a relatively low solubility (i.e., an anti-solvent) was added to the solution. A precipitate formed immediately in some solvent/anti-solvent systems. If the precipitation did not occur immediately, the resulting mixture was allowed to cool in a refrigerator (about 0-5° C.) until a precipitate formed. The precipitate was then isolated by decantation and allowed to dry in the air.

Interconversion Studies. Interconversion experiments were performed by making slurries of a solid form in a saturated solvent. The slurries were agitated for at least 2 days at about 25° C. The saturated solution was removed by filtration and the solid was dried in the air.

Compression Studies. Compression tests were performed by pressing the sample under 2000 psi force for at least one minute with Carver Mini C presser. The sample was then analyzed by XRPD.

Hygroscopicity studies. The hygroscopicity of various solid forms was studied using a Surface Measurement Systems DVS instrument. Typically a sample size of between about 10-50 mg was loaded into the DVS instrument sample pan and the sample was analyzed on a DVS automated sorption analyzer at about 25° C. The relative humidity was increased in increments of about 10% from about 0% to about 95% RH. The relative humidity was then decreased in a similar manner to accomplish a full adsorption/desorption cycle. The mass was recorded at periodic intervals throughout the experiment.

5.12.2. Characterization Methodology

Samples generated as described in the solid form screen were typically analyzed by X-Ray Powder Diffraction (XRPD). XRPD was conducted on a Thermo ARL X'TRA™ X-ray powder diffractometer using Cu Kα radiation at 1.54 Å. The instrument was equipped with a fine focus X-ray tube. The voltage and amperage of X-ray generator were set at 45 kV and 40 mA, respectively. The divergence slices were set at 4 mm and 2 mm and the measuring slices were set at 0.5 mm and 0.2 mm. The diffracted radiation was detected by a peltier-cooled Si(Li) solid-state detector. Typically, a theta-two theta continuous scan at 2.40°/min (0.5 sec/0.02° step) from 1.5 °2θ to 40° 2θ was used. A sintered alumina standard was used to check the peak position. In general, positions of XRPD peaks are expected to individually vary on a measurement-by-measurement basis by about ±0.2°2θ. In general, as understood in the art, two XRPD patterns match one another if the characteristic peaks of the first pattern are located at approximately the same positions as the characteristic peaks of the second pattern. As understood in the art, determining whether two XRPD patterns match or whether individual peaks in two XRPD patterns match may require consideration of individual variables and parameters such as, but not limited to, preferred orientation, phase impurities, degree of crystallinity, particle size, variation in diffractometer instrument setup, variation in XRPD data collection parameters, and/or variation in XRPD data processing, among others. The determination of whether two patterns match may be performed by eye and/or by computer analysis. Examples of XRPD patterns collected and analyzed using these methods and parameters are provided herein, e.g., as FIG. 1, FIG. 5, FIG. 9, FIG. 13, FIG. 17, FIG. 21 and FIG. 25.

Differential Scanning Calorimetry (DSC) analyses were performed on a TA Instruments Q1000™. About 5 mg of sample was placed into a tared DSC pan and the weight of the sample was accurately recorded. Typically, the sample was heated under nitrogen at a rate of about 10° C./min from about 25° C. up to a final temperature of about 200° C. Typically, thermal events were reported as extrapolated onset temperatures. Examples of DSC thermograms collected and analyzed using these methods and parameters are provided herein, e.g., as FIG. 2, FIG. 6, FIG. 10, FIG. 14, FIG. 18, FIG. 22 and FIG. 26.

Thermal Gravimetric Analyses (TGA) were performed on a TA Instruments Q500™. Calcium oxalate was used for calibration. About 10 mg of sample was placed on a pan, accurately weighed and loaded into the TGA furnace. The sample was heated under nitrogen at a rate of about 10° C./min from about 25° C. up to a final temperature of about 200° C. Examples of TGA thermograms collected and analyzed using these methods and parameters are provided herein, e.g., as FIG. 3, FIG. 7, FIG. 11, FIG. 15, FIG. 19, FIG. 23 and FIG. 27.

Solvation solvents were identified and quantified by TG-IR experiments using a TA Instruments Q500™ TGA interfaced with a Thermo Nicolet AEM Fourier transform IR spectrophotometer. Typically a sample size of about 20-50 mg was weighed into an aluminum pan and heated to about 200° C. During the TGA run, the vapor was transferred to the cell through a heated transfer line. The temperature of both transfer line and the cell were set at about 225° C. IR spectra were collected every 10-second repeat time. Volatiles were identified from a search of the Aldrich vapor phase spectral library and the library match results are presented to show the identified vapor.

Morphology and particle size analysis of the samples were carried out using an Olympus microscope. The instrument was calibrated with USP standards. $D_{90}$ values were determined using the software Image Plus—Material Plus. The $D_{90}$ value represents the 90th percentile of the particle size distribution as measured by length; i.e., 90% of the particles have a length of this value or less.

5.12.3. Solid Form Screening Study Results

Solid forms comprising Compound A which were prepared during the solid form screening studies included Forms A, B, C, D, E, F, G and an amorphous form. Representative XRPD patterns, DSC plots, TGA plots and DVS plots for each of Forms A, B, C, D, E, F and G are provided herein as FIG. 1-FIG. 28.

Solubility Studies. The approximate solubility of Form B of Compound A in various solvents at about 25° C. was determined. Results are shown in Table 6. Form B was found to be most soluble in acetone, acetonitrile, methylene chloride, methyl ethyl ketone and tetrahydrofuran (greater than about 50 mg/mL) followed by ethyl acetate (about 30.15 mg/mL). Form B was also found to have low solubility in several solvents including n-butanol, heptane, 2-propanol, toluene and water (less than about 1 mg/mL).

Solution Evaporation Studies. Results from solution evaporation studies performed at about 25° C. and about 50° C. are summarized in Table 7.

Equilibration Studies. Results from equilibration studies performed at about 25° C. and about 50° C. are summarized in Table 8.

Cooling Crystallization Studies. Results from cooling crystallization studies are summarized in Table 9. Cooling crystallization studies yielded crystalline material from numerous solvents, including acetone, acetonitrile, n-butyl acetate, ethyl acetate, methanol, methylene chloride, methyl ethyl ketone (MEK) and tetrahydrofuran (THF). The crystalline materials obtained were typically characterized by XRPD, DSC and TGA.

Solvent/Anti-Solvent Precipitation Studies. Results from solvent/anti-solvent precipitation studies are summarized in Table 10. When heptane, water and toluene were added to Form B in THF solution at about 40° C., precipitates formed immediately. When heptane, methyl t-butyl ether (MTBE), toluene and water were added to Form B in acetonitrile solution separately at about 25° C., either a clear solution or a mixture formed. Crystalline material from MTBE/acetonitrile, water/acetonitrile and toluene/acetonitrile was obtained after stirring overnight. However, no crystallization occurred for heptane/acetonitrile mixture. When water was added to Form B in methanol solution at about 50° C., precipitates formed immediately and when heptane and toluene were added to Form B in methanol solution separately at about 50° C., either a clear solution or a mixture formed. Crystalline material from toluene/methanol and heptane/methanol was obtained after stirring overnight. When toluene was added to Form B in methylene chloride solution at about 25° C., precipitates formed immediately and when MTBE was added to Form B in methylene chloride solution at about 25° C., a clear solution was obtained. Crystalline material from MTBE/methylene chloride was obtained after stirred overnight. However, no crystallization occurred when heptane was added to Form B in methylene chloride solution. When heptane was added to Form B in MEK solution at about 50° C., precipitates formed immediately and when MTBE and toluene were added to Form B in MEK solution separately at about 50° C., clear solutions were obtained. Crystalline material from MTBE/MEK and toluene/MEK was obtained after stirring overnight. When heptane was added to Form B in n-butyl acetate solution at about 50° C., precipitates formed immediately and when MTBE and toluene were added to Form B in MEK solution separately at about 50° C., clear solutions were obtained. Crystalline material from MTBE/n-butyl acetate and toluene/n-butyl acetate was obtained after stirring overnight. When water and toluene were added to Form B in acetone solution separately at about 40° C., precipitates formed immediately and when ethanol and 2-propanol were added to Form B in acetone solution separately at about 40° C., clear solutions were obtained. Crystalline material from ethanol/acetone and 2-propanol/acetone were obtained after stirring overnight. Crystalline materials obtained were identified by XRPD, DSC, TGA.

Stability Studies. Stability study results are summarized in Table 11. The stabilities of Forms A, B, C and D were studied by exposing the solid samples to the stress condition of 40° C./75% RH for four weeks. Moreover, the stabilities of Forms A, B, C and D in different solvents were studied by equilibration in different solvents at 40° C. for four weeks. The slurries then were filtered and dried in the air. Solid samples obtained from the stability experiments were analyzed by XRPD and DSC.

Interconversion Studies. Results from interconversion studies are summarized in Table 12.

Compression Studies. Compression tests were performed on Forms A, B, C, D, E, F and G of Compound A. Each form studied was found to be substantially physically stable as observed by XRPD analysis.

Hygroscopicity Studies. Hygroscopicity (moisture sorption/desorption) studies were performed on Forms A, B, C, D, E, F and G. Each of the solid samples were analyzed by XRPD after undergoing a full adsorption/desorption cycle in the DVS system. XRPD results indicated that none of the forms analyzed underwent substantial solid-state transformation as a result of DVS analysis.

TABLE 6

Solubility Study on Form B

| Solvent System | Approximate Solubility (mg/ml) |
| --- | --- |
| Acetone | >50 |
| Acetonitrile | >50 |
| n-Butanol | >0.72 |
| n-Butyl acetate | 9.75 |
| Absolute ethanol | 1.38 |
| Ethyl acetate | 30.15 |
| Heptane | 0.41 |
| Methylene chloride | >50 |
| Methyl ethyl ketone | >50 |
| Methanol | 4.05 |
| Methyl t-butyl ether | 1.17 |
| 2-Propanol | 0.81 |
| Tetrahydrofuran | >50 |
| Toluene | 0.90 |
| Water | 0.69 |
| Ethanol:Water (1:1) | 2.86 |

TABLE 7

Solution Evaporation Studies

| Starting Form | Solvent System | Evaporation Temp. (° C.) | XRPD Analysis | DSC thermal events |
| --- | --- | --- | --- | --- |
| B | Acetone | 25 | Form B | |
| B | Acetonitrile | 25 | Form B + Form E | 77.28° C.; 151.84° C. |
| B | n-Butyl acetate | 25 | Form B | |
| B | Ethyl acetate | 25 | Form B | |
| B | Methylene chloride | 25 | Form D | 93.11° C. |
| B | Methyl ethyl ketone | 25 | Form B | |
| B | Tetrahydrofuran | 25 | Form B | |
| B | Ethanol:Water (1:1) | 25 | Form B | |
| A | Acetonitrile | 25 | Form E | 95.42° C. (TGA wt. loss = 3.56%) |
| A | Methylene chloride | 25 | Form D | 97.23° C. |
| A | Acetone | 50 | Form B | |
| A | Acetonitrile | 50 | Form B | |
| A | n-Butyl acetate | 50 | Form B | |
| A | Ethyl acetate | 50 | Form B | |
| A | Methyl ethyl ketone | 50 | Form B | |
| A | Tetrahydrofuran | 50 | Form B | |
| A | Ethanol:Water (1:1) | 50 | Form B | |

TABLE 8

Equilibration Studies

| Starting Form | Solvent System | Equilib. Temp. °C. | XRPD Analysis | DSC Thermal Events |
|---|---|---|---|---|
| B | n-Butanol | 25 | Form B | |
| B | n-Butyl acetate | 25 | Form B | |
| B | Ethanol | 25 | Form B | |
| B | Ethyl acetate | 25 | Form B | |
| B | Heptane | 25 | Form B | |
| B | Methanol | 25 | Form B | |
| B | Methyl t-butyl ether | 25 | Form B | |
| B | 2-Propanol | 25 | Form B | |
| B | Toluene | 25 | Form C | 159.31° C. |
| B | Toluene (evap. at 60° C.) | 25 | Form C | Broad multiplet |
| B | Toluene:Acetone (9:1) (evap. at 100° C.) | 25 | Form C | Broad multiplet (TGA wt. loss = 5.90%) |
| B | Water | 25 | Form B | |
| B | Water (50 days) | 25 | Form B | |
| A | Ethanol | 25 | Form F | 145.06° C. (multiplet) |
| A | Heptane | 25 | Form A | |
| A | Ethyl acetate | 25 | Form G | 108.96° C. |
| A | Water | 25 | Form A | |
| A | Toluene | 25 | Form C | 170.18° C. (TGA wt. loss = 5.86%) |
| A | Toluene (evap. at 60° C.) | 25 | Form C | 167.84° C. |
| A | Toluene:Acetone (9:1) (evap. at 100° C.) | 25 | Form C | Broad multiplet |
| A | Acetone:Ethanol (1:1) | 25 | Form B | 154.00° C. (main) |
| A | Ethanol:Water (1:1) | 25 | Form F | 145.22° C. |
| A | n-Butanol | 50 | Form B | |
| A | n-Butyl acetate | 50 | Form B | |
| A | Ethanol | 50 | Form B | |
| A | Heptane | 50 | Form B | |
| A | Methanol | 50 | Form B | |
| A | Methyl t-butyl ether | 50 | Form B | |
| A | 2-Propanol | 50 | Form B | |
| A | Toluene | 50 | Form C | 165.30° C. (multiplet) |
| A | Water | 50 | Form B | |
| A | Ethanol:Water (1:1) | 50 | Form B | |

TABLE 9

Cooling Crystallization Studies

| Starting Form | Solvent System | Analysis by XRPD | DSC Thermal Events |
|---|---|---|---|
| B | Acetone | Form E | |
| B | Acetonitrile | Form E | 95.42° C. |
| B | n-Butyl acetate | Form B | |
| B | Ethyl acetate | Form B | |
| B | Methylene Chloride | Form D | 100.90° C. |
| B | Methanol | Form B | |
| B | Methyl ethyl ketone | Form B | |
| B | THF | Form H | |

TABLE 10

Solvent/Anti-Solvent Precipitation Studies

| Starting Form | Solvent* | Anti-Solvent* | Ratio (Solvent:Antisolvent) & Temp. | Analysis by XRPD | DSC Thermal Events |
|---|---|---|---|---|---|
| B | Acetone | Ethanol | 1:8 at 40° C. | Form B | |
| B | Acetone | 2-Propanol | 1:10 at 40° C. | Form B | |
| B | Acetone | Water | 1:4 at 40° C. | Form B | |
| B | Acetone | Toluene | 1:10 at 40° C. | Form C | 167.57° C. (broad) |
| B | Acetonitrile | Heptane | 1:8 at 25° C. | Form B | |
| B | Acetonitrile | MtBE | 1:8 at 25° C. | Form B | |
| B | Acetonitrile | Water | 1:6 at 25° C. | Form B | |
| B | Acetonitrile | Toluene | 1:8 at 50° C. | Form C | 167.97° C. |
| B | Methyl ethyl ketone | Heptane | 1:3 at 50° C. | Form B | |
| B | MEK | MtBE | 1:4 at 50° C. | Form B | |
| B | MEK | Toluene | 1:3 at 50° C. | Form C | 168.22° C. |
| B | n-Butyl acetate | Heptane | 1:4 at 50° C. | Form B | |
| B | n-Butyl acetate | MtBE | 1:4 at 50° C. | Form B | |
| B | n-Butyl acetate | Toluene | 1:4 at 50° C. | Form B | |
| B | DCM | Heptane | 1:8 at 25° C. | Form E + B | 89.65° C.; 149.81° C. |
| B | DCM | MtBE | 1:15 at 25° C. | Form B | |
| B | DCM | Toluene | 1:15 at 25° C. | Form B | 167.99° C. (multiplet) |
| B | Methanol | Heptane | 1:3 at 50° C. | Form B | |
| B | Methanol | Water | 1:3 at 50° C. | Form B | |
| B | Methanol | Toluene | 1:3 at 50° C. | Form C | 168.37° C. (multiplet) |
| B | Tetrahydrofuran | Heptane | 1:6 at 40° C. | Form B | |
| B | Tetrahydrofuran | Water | 1:6 at 40° C. | Form B | |
| B | Tetrahydrofuran | Toluene | 1:6 at 40° C. | Form C | 168.64° C. (multiplet) |

*Abbreviations:
MEK = methyl ethyl ketone;
DCM = dichloromethane (i.e., methylene chloride);
MtBE = methyl t-butyl ether

TABLE 11

Stability Studies

| Starting Form | Test Conditions ("EQ" = equilibrate; "RH" = relative humidity) | Appearance | Analysis by XRPD |
|---|---|---|---|
| Form A | 40° C./75% RH; 4 weeks | White solid | Form A |
| Form B | 40° C./75% RH; 4 weeks | White solid | Form B |
| Form C | 40° C./75% RH; 4 weeks | Yellow solid | Form C |
| Form D | 40° C./75% RH; 4 weeks | White solid | Form D |
| Form A | EQ in ethanol at 40° C. for 4 weeks | | Form F |
| Form A | EQ in heptane at 40° C. for 4 weeks | | Form A |
| Form A | EQ in water at 40° C. for 4 weeks | | Form A |
| Form A | EQ in toluene at 40° C. for 4 weeks | | Form C |
| Form B | EQ in ethanol at 40° C. for 4 weeks | | Form B |
| Form B | EQ in heptane at 40° C. for 4 weeks | | Form B |
| Form B | EQ in water at 40° C. for 4 weeks | | Form B |
| Form B | EQ in toluene at 40° C. for 4 weeks | | Form B |
| Form C | EQ in ethanol at 40° C. for 4 weeks | | Form C |
| Form C | EQ in heptane at 40° C. for 4 weeks | | Form C |
| Form C | EQ in water at 40° C. for 4 weeks | | Form C |
| Form C | EQ in toluene at 40° C. for 4 weeks | | Form C |
| Form D | EQ in ethanol at 40° C. for 4 weeks | | Form B |
| Form D | EQ in heptane at 40° C. for 4 weeks | | Form B |
| Form D | EQ in water at 40° C. for 4 weeks | | Form B |
| Form D | EQ in toluene at 40° C. for 4 weeks | | Form C |

TABLE 12

Interconversion Studies

| Starting Form | Test Conditions ("EQ" = equilibrate) | Analysis by XRPD |
|---|---|---|
| Mixture of Forms A, B, C, D, E, F and G | EQ in acetone:ethanol (1:1) at 25° C. | Form B + C + F |
| Form A | EQ in acetone:ethanol (1:1) at 25° C. | Form B |
| Form C | EQ in acetone:ethanol (1:1) at 25° C. | Form C |
| Form D | EQ in acetone:ethanol (1:1) at 25° C. | Form B |
| Form E | EQ in acetone:ethanol (1:1) at 25° C. | Form B |
| Form F | EQ in acetone:ethanol (1:1) at 25° C. | Form F |
| Form G | EQ in acetone:ethanol (1:1) at 25° C. | Form B |

5.13. Example 13

200 Mg Dosage Capsule

Table 13 illustrates a batch formulation and single dosage formulation for a single dose unit containing 200 mg of a solid form comprising Compound A, i.e., about 40 percent by weight, in a size #0 capsule.

TABLE 13

Formulation for 200 mg capsule

| Material | Percent By Weight | Quantity (mg/tablet) | Quantity (kg/batch) |
|---|---|---|---|
| Compound A | 40.0% | 200 mg | 16.80 kg |
| Pregelatinized Corn Starch, NF5 | 9.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS™ B-820) and Compound A components are passed through a 710 μm screen and then are loaded into a Diffusion Mixer with a baffle insert and blended for 15 minutes. The magnesium stearate is passed through a 210 μm screen and is added to the Diffusion Mixer. The blend is then encapsulated in a size #0 capsule, 500 mg per capsule (8400 capsule batch size) using a Dosator type capsule filling machine.

5.14. Example 14

100 Mg Oral Dosage Form

Table 14 illustrates a batch formulation and a single dose unit formulation containing 100 mg of a solid form comprising Compound A.

TABLE 14

Formulation for 100 mg tablet

| Material | Percent by Weight | Quantity (mg/tablet) | Quantity (kg/batch) |
|---|---|---|---|
| Compound A | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and Compound A components are passed through a #30 mesh screen (about 430μ to about 655μ). The Pluronic F-68® (manufactured by JRH Biosciences, Inc. of Lenexa, Kans.) surfactant is passed through a #20 mesh screen (about 457% to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The solid form comprising Compound A is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A Form B crystal form of the compound of Formula (I):

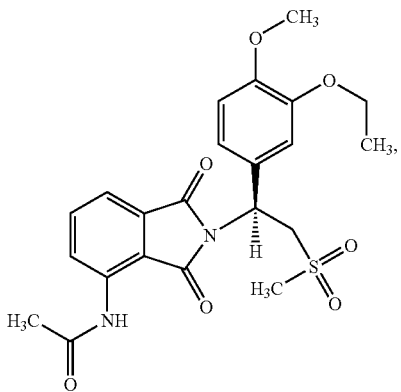

which is enantiomerically pure, and which has an X-ray powder diffraction pattern comprising peaks at about 10.1, 13.5, 20.7, and 26.9 degrees 2θ.

2. The crystal form of claim 1, which has an X-ray powder diffraction pattern further comprising peaks at about 12.4, 15.7, 18.1, and 24.7 degrees 2θ.

3. The crystal form of claim 2, which has an X-ray powder diffraction pattern further comprising peaks at about 16.3, 22.5, 26.2, and 29.1 degrees 2θ.

4. The crystal form of claim 1, which has an X-ray powder diffraction pattern matching the pattern depicted in FIG. 5.

5. The crystal form of claim 1, which has a differential scanning calorimetry plot comprising an endothermic event with an onset temperature of about 154° C.

6. The crystal form of claim 1, which has a differential scanning calorimetry plot matching the plot depicted in FIG. 6.

7. The crystal form of claim 1, which has a thermal gravimetric analysis plot comprising a mass loss of less than about 1% when heated from about 25° C. to about 140° C.

8. The crystal form of claim 7, wherein the mass loss is about 0.25%.

9. The crystal form of claim 1, which has a thermal gravimetric analysis plot matching the plot depicted in FIG. 7.

10. The crystal form of claim 1, which exhibits a mass increase of less than about 1% when subjected to an increase in relative humidity from about 0% to about 95% relative humidity.

11. The crystal form of claim 10, wherein the mass increase is about 0.6%.

12. The crystal form of claim 1, which has a moisture sorption isotherm plot matching the plot depicted in FIG. 8.

13. The crystal form of claim 1, which is stable upon exposure to about 40° C. and about 75% relative humidity for about 4 weeks.

14. The crystal form of any one of claims 1 and 2 to 13, which is substantially pure.

15. A solid pharmaceutical composition comprising the crystal form of any one of claims 1 and 2 to 13.

* * * * *